United States Patent
Wantanabe et al.

(10) Patent No.: US 6,441,021 B1
(45) Date of Patent: Aug. 27, 2002

(54) SULFONATED AMINO ACID DERIVATIVES AND METALLOPROTEINASE INHIBITORS CONTAINING THE SAME

(75) Inventors: Fumihiko Wantanabe, Nara; Hiroshige Tsuzuki, Kyoto; Mitsuaki Ohtani, Nara, all of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/710,904

(22) Filed: Nov. 14, 2000

Related U.S. Application Data

(62) Division of application No. 09/120,197, filed on Jul. 22, 1998, now Pat. No. 6,207,698, which is a continuation of application No. PCT/JP97/00126, filed on Jan. 22, 1997.

(30) Foreign Application Priority Data

Jan. 23, 1996 (JP) .............................................. 8-30082
Aug. 13, 1996 (JP) ............................................. 8-213555

(51) Int. Cl.$^7$ ...................... A61K 31/404; C07D 209/20
(52) U.S. Cl. ......................................... 514/419; 548/496
(58) Field of Search ........................... 548/496; 514/419

(56) References Cited

U.S. PATENT DOCUMENTS

| | | | |
|---|---|---|---|
| 4,666,931 A | 5/1987 | Ohishi et al. ................ | 514/389 |
| 5,455,258 A | 10/1995 | MacPherson et al. ........ | 514/357 |
| 5,650,428 A | 7/1997 | Ohmori et al. .............. | 514/419 |
| 5,756,545 A | 5/1998 | O'Brien et al. .............. | 514/562 |
| 5,900,427 A | 5/1999 | Vedejs et al. ................ | 514/367 |
| 6,150,394 A | * 11/2000 | Watanabe et al. ........... | 514/415 |

FOREIGN PATENT DOCUMENTS

| | | |
|---|---|---|
| EP | 0 468 231 | 1/1992 |
| EP | 0 757 037 | 2/1997 |
| EP | 0 757 984 | 2/1997 |
| JP | 57-59969 | 4/1982 |
| JP | 2508444 | 12/1982 |
| WO | 93/14069 | 7/1993 |
| WO | 95/35276 | 12/1995 |
| WO | 96/00214 | 1/1996 |
| WO | 97/45402 | 12/1997 |

OTHER PUBLICATIONS

Ksander, J. Med. Chem., 38 1689–1700 (1995).
Shin–zikkenkagakukoza, vol. 14 1787 (1978).
Hamada, Synthesis, 852–854 (1986).
Sonogashira, Tetrahedron Lett. No. 50, 4467–4470 (1975).
Sharp, Tetrahedron Lett., vol. 26, No. 49, 5997–6000 (1985).
Chem. Berr., 87, 1318–1330 (1954).
Wilhelm, Journal Biol. Chem., vol. 264, No. 29, 17213–17221 (1989).
Okada, Journal Biol. Chem., vol. 267, 21712–21719 (1992).
Ward, Biochemical Journal, vol. 278, 179–187 (1991).

Tanaka, Biochemical Biophysical Research Communications., vol. 190, No. 3, 732–740 (1993).

Kocsis et al., chemical Abstracts, 100: 209513, 1984.

Ibrahim et al., Chemical Abstracts, 121: 109633, 1994.

A.K. Debnath et al., "4–(4'–Substituted benzoyl) aminobenzenesulphonyl–L(+)–glutamic acids and 5–N–substituted–2–[4'–(4" substituted benzoyl) aminobenzenesulphonyl]–L–glutamines as potential antineoplastic agents: Syntheses biological evaluation and quantitative structure–activity relationship studies.", Indian J. of chem., vol. 28B, pp. 843–847, (1989).

B. Galli et al., "Enantiomeric separation of dansyl and dabsylamino acids by ligand–exchange chromatography with (S) and (R)–phenylalaninamide–modified silica gel.", J. of Chroma., A. 666, pp. 77–89, 1994.

J. Hansel et al., "Oxazoline Formation via a Palladium–catalyzed Cyclization: A Direct, Stereoselective to cis–5–Amino–2–cyclopenten–1–ol Derivatives.", Tetrahedron Letters, vol. 36, No. 17, pp. 2913–2916, 1995.

J. Hlavacek et al., "An Alternative Route to $N^\alpha$–Methylamino Acid Derivatives: Synthesis and Conformation of Some $N^\alpha$–Acetyl-$N^\alpha$–Methylamino Acid Methylamides.", Collect. Czechoslovak Chem. Commun., vol. 53, 1988.

C. Kaiser et al., "2–Substitiuted Derivatives of 3,4–Dihydrophenylalanine.", vol. 79, pp. 4365–4370, 1957.

S. H. Lee et al., "Systematic study on the resolution of derivatized amino acids enantiomers on different cyclodextrin–bonded stationary phases.", J. of Chroma., vol. 603, pp. 83–93, 1992.

J. Lin et al., "Debsyl Chloride: Its Synthesis, Characterization and Application in Amino Acid and Amine Microanalysis." J. of the Chinese Biochem. Soc., vol. 14, No. 1, pp. 10–19, 1985.

(List continued on next page.)

*Primary Examiner*—Fiona T. Powers
(74) *Attorney, Agent, or Firm*—Foley & Lardner

(57) ABSTRACT

Compounds having a metalloproteinase inhibitory activity, represented by the formula (I), its optically active isomers, their pharmaceutically acceptable salts, or hydrates thereof

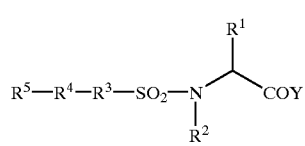

I

18 Claims, No Drawings

OTHER PUBLICATIONS

S. Natelson et al., "Preparation of D–, DL–, and L–Homoserine Lactone from Methionine.", Microchem. Journ., vol. 40, pp. 226–232, 1989.

P. Nickel et al., "Carboxylic acid analogues of suramin, potential filaricides.", Indian Journ. Of Chem., vol. 30B, pp. 182–187, 1991.

V. Stocchi et al., "Reversed–Phase High–Performance Liquid Chromatography Separation of Dimethylaminoazobenzene Sulfonyl and Dimethylaminoazobenzene Thiohydantoin–Amino Acid Derivatives for Amino Acid Analysis and Microsequencing Studies at the Picomole Level.", Analyt. Biochem., vol. 178, pp. 107–117, 1989.

M. Verderame et al., "Sulfide Derivatives of Cysteine II.", J. of Pharma. Sci., vol. 51, No. 6, pp. 576–579, 1962.

N. Yoneda et al., "Reactions of L–a–Tosylamido–β–propiolactone. I. Synthesis, Reactions with Amines and Derivation to L–Serine.", UDC, vol. 89, No. 1, pp. 98–103, 1969.

* cited by examiner

SULFONATED AMINO ACID DERIVATIVES AND METALLOPROTEINASE INHIBITORS CONTAINING THE SAME

This application is a divisional application of 09/120,197, filed Jul. 22, 1998, now U.S. Pat. No. 6,207,698, which is in turn a continuation of PCT/JP97/00126, filed on Jan. 22, 1997.

TECHNICAL FIELD

This application relates to sulfonated amino acid derivatives and metalloproteinase inhibitors containing the same.

1. Background Art

An extracellular matrix consists of collagen, proteoglycan, etc., has a function to support tissues, and plays a role in a maintaining of a cell functions, for example propagation, differentiation, adhesion, or the like. Matrix metalloproteinases (MMP) such as gelatinase, stromelysin, collagenase, and the like have an important role in degradation of an extracellular matrix, and these enzymes work for growth, tissue remodeling, etc. under physiological conditions. Therefore, it is considered that these enzymes participate in progression of various kind of diseases involving breakdown and fibrosis of tissues, such as osteoarthritis, rheumatoid arthritis, corneal ulceration, periodontitis, metastasis and invasion of tumor, and virus infection (for example, HIV infection). At the present time, it is not clear which enzyme participates in the above diseases seriously, but it is considered that these enzymes at least participate in tissue breakdown. As metalloproteinase inhibitors of amino acid derivatives, for example hydroxamic acid derivatives of amino acids (JP-A-6-2562939), carboxylic acid derivatives of amino acid and/or their hydroxamic acid derivatives (WO95/35276), etc. are disclosed.

2. Disclosure of Invention

If it is able to inhibit the activity of MMP, it is considered that MMP inhibitors contribute to an improvement and prevention of the above diseases caused by or related to its activity. Therefore, development of MMP inhibitors has long been desired.

In the above situation, the inventors of the present invention found that a kind of sulfonamide derivatives have strong activity to inhibit MMP.

The present invention relates to a composition for inhibiting metalloproteinase which contains a compound of the formula I:

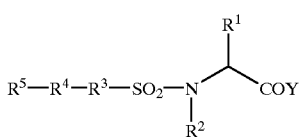

wherein $R^1$ is optionally substituted lower alkyl, optionally substituted aryl, optionally substituted aralkyl, optionally substituted heteroaryl, or optionally substituted heteroarylalkyl; $R^2$ is hydrogen atom, optionally substituted lower alkyl, optionally substituted aryl, optionally substituted aralkyl, optionally substituted heteroaryl, or optionally substituted heteroarylalkyl; $R^3$ is a bond, optionally substituted arylene, or optionally substituted heteroarylene; $R^4$ is a bond, —(CH$_2$)m—, —CH=CH—, —C≡C—, —CO—, —CO—NH—, —N=N—, —N(R$^A$)—, —NH—CO—NH—, —NH—CO—, —O—, —S—, —SO$_2$NH—, —SO$_2$—NH—N=CH—, or tetrazol-diyl; $R^5$ is optionally substituted lower alkyl, optionally substituted $C_3$–$C_8$ cycloalkyl, optionally substituted aryl, optionally substituted heteroaryl, or an optionally substituted non-aromatic heterocyclic group; $R^A$ is hydrogen atom or lower alkyl; Y is —NHOH or —OH; and m is 1 or 2; provided $R^2$ is hydrogen atom when Y is —NHOH, its optically active substance, their pharmaceutically acceptable salt, or hydrate thereof.

Mentioned in more detail, the invention relates to the following a)–b), 1)–16), and A)–C).

a) A composition for inhibiting metalloproteinase which contains a compound of the formula I:

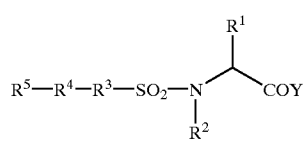

wherein $R^1$ is optionally substituted lower alkyl, optionally substituted aryl, optionally substituted aralkyl, optionally substituted heteroaryl, or optionally substituted heteroarylalkyl; $R^2$ is hydrogen atom, optionally substituted lower alkyl, optionally substituted aryl, optionally substituted aralkyl, optionally substituted heteroaryl, or optionally substituted heteroarylalkyl; $R^3$ is a bond, optionally substituted arylene, or optionally substituted heteroarylene; $R^4$ is a bond, —(CH$_2$)m—, —CH=CH—, —C≡C—, —CO—, —CO—NH—, —N=N—, —N(R$^A$)—, —NH—CO—NH—, —NH—CO—, —O—, —S—, —SO$_2$NH—, —SO$_2$—NH—N=CH—, or tetrazol-diyl; $R^5$ is optionally substituted lower alkyl, optionally substituted $C_3$–$C_8$ cycloalkyl, optionally substituted aryl, optionally substituted heteroaryl, or an optionally substituted non-aromatic heterocyclic group; $R^A$ is hydrogen atom or lower alkyl; Y is —NHOH or —OH; and m is 1 or 2; provided $R^2$ is hydrogen atom when Y is —NHOH, $R^5$ is optionally substituted aryl or optionally substituted heteroaryl when $R^3$ is optionally substituted arylene or optionally substituted heteroarylene and $R^4$ is CO—NH— or —NH—CO—, $R^5$ is optionally substituted aryl or optionally substituted heteroaryl when $R^3$ is optionally substituted arylene or optionally substituted heteroarylene and $R^4$ is tetrazol-diyl, $R^5$ is lower alkyl, aryl substituted by lower alkyl or optionally substituted aryl, or heteroaryl substituted by lower alkyl or optionally substituted aryl when $R^3$ is optionally substituted arylene and $R^4$ is a bond, both of $R^3$ and $R^4$ are not a bond at the same time, and $R^4$ is not —O— when $R^3$ is optionally substituted arylene or optionally substituted heteroarylene, its optically active substance, their pharmaceutically acceptable salt, or hydrate thereof b) A composition for inhibiting metalloproteinase as mentioned above, which is a composition for inhibiting type-IV collagenase.

Preferred embodiment of the present invention are as follows.

1) A compound of the formula I:

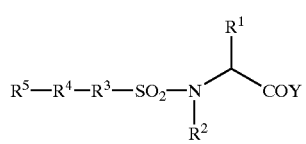

wherein $R^1$ is optionally substituted lower alkyl, optionally substituted aryl, optionally substituted aralkyl, optionally substituted heteroaryl, or optionally substituted heteroarylalkyl; $R^2$ is hydrogen atom, optionally substituted lower alkyl optionally substituted aryl, optionally substituted aralkyl, optionally substituted heteroaryl, or optionally substituted heteroarylalkyl; $R^3$ is a bond, optionally substituted arylene, or optionally substituted heteroarylene; $R^4$ is a bond, —(CH$_2$)m—, —CH=CH—, —C≡C—, —CO—, —CO—NH—, —N=N—, N(R$^A$)—, —NH—CO—NH—, —NH—CO—, —O—, —S—, —SO$_2$NH—, —SO$_2$—NH—N=CH—, or tetrazol-diyl; $R^5$ is optionally substituted lower alkyl, optionally substituted $C_3$–$C_8$ cycloalkyl, optionally substituted aryl, optionally substituted heteroaryl, or an optionally substituted non-aromatic heterocyclic group; $R^A$ is hydrogen atom or lower alkyl; Y is —NHOH or —OH; and m is 1 or 2; provided $R^2$ is hydrogen atom when Y is —NHOH, $R^5$ is optionally substituted aryl or optionally substituted heteroaryl when $R^3$ is optionally substituted arylene or optionally substituted heterolene and $R^4$ is —CO—NH— or —NH—CO— (when $R^3$ is phenylene and $R^4$ is —CO—NH—, $R^1$ is not methyl or phenyl and $R^5$ is not 2-chlorophenyl, 4-chlorophenyl, or 2,4-dichlorophenyl), $R^5$ is lower alkyl, optionally substituted aryl, or optionally substituted heteroaryl when $R^3$ is alkyl, optionally substituted arylene or optionally substituted heteroarylene and $R^4$ is tetrazol-diyl, $R^5$ is lower alkyl, aryl substituted with lower alkyl or optionally substituted aryl, or heteroaryl substituted with lower alkyl or optionally substituted aryl when $R^3$ is optionally substituted arylene and $R^4$ is a bond, both of $R^3$ and $R^4$ are not a bond at the same time, and $R^4$ is not —O— when $R^3$ is optionally substituted arylene or optionally substituted heteroarylene, its optically active substance, their pharmaceutically acceptable salt, or hydrate thereof.

2) A compound of the formula II:

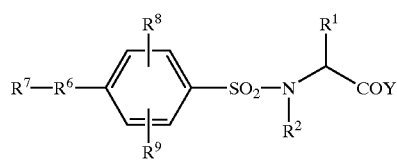

wherein $R^6$ is —CH=CH—, —C≡C—, —N=N—, —NH—CO—NH—, —S—, —SO$_2$NH—, or —SO$_2$—NH—N=CH—; $R^7$ is optionally substituted aryl or optionally substituted heteroaryl; $R^8$ and $R^9$ are each independently hydrogen atom, lower alkoxy, or nitro; $R^1$, $R^2$, and Y are as defined above, its optically active substance, their pharmaceutically acceptable salt, or hydrate thereof 3) A compound of the formula III:

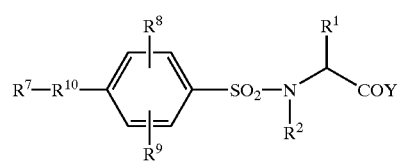

wherein $R^{10}$ is —(CH$_2$)m—, —CO—, —CO—NH—, —N(R$^A$)—, —NHCO—, or tetrazol-diyl; m is 1 or 2; $R^1$, $R^2$, $R^7$, $R^8$, $R^9$, $R^A$, and Y are as defined above, provided $R^1$ is not methyl or phenyl and $R^7$ is not 2-chlorophenyl, 4-chlorophenyl, or 2,4-dichlorophenyl when $R^{10}$ is —NH—CO—, its optically active substance, their pharmaceutically acceptable salt, or hydrate thereof.

4) A compound of the formula IV:

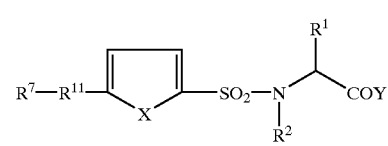

wherein $R^{11}$ is a bond, —CH=CH—, or —C≡C—; X is oxygen atom or sulfur atom, $R^1$, $R^2$, $R^7$, and Y are as defined above, its optically active substance, their pharmaceutically acceptable salt, or hydrate thereof.

5) A compound of the formula I':

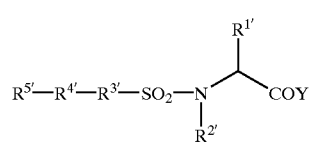

wherein $R^{1'}$ is benzyl, (indol-3-yl)methyl, (1-methylindol-3-yl)methyl, (5-methylindol-3-yl)methyl, (1-acetylindol-3-yl)methyl, (1-methylsulfonylindol-3-yl)methyl, (1-alkoxycarbonyl-3-yl)methyl (for example ethoxycarbonylmethyl), or i-propyl; $R^{2'}$ is hydrogen atom, methyl, 4-aminobutyl, or benzyl; $R^{3'}$ is 1,4-phenylene; $R^{4'}$ is —O—; $R^{5'}$ is phenyl or 4-hydroxyphenyl; and Y is as defined above, its optically active substance, their pharmaceutically acceptable salt, or hydrate thereof.

6) A compound of the formula I":

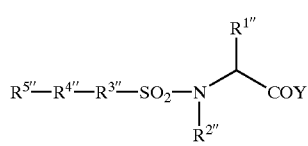

wherein $R^{1''}$ is 4-thiazolylmethyl, (indol-3-yl)methyl, (5-methoxyindol-3-yl)methyl, 1-naphthylmethyl, 2-naphthylmethyl, 4-biphenylylmethyl, 2,2,2-trifluoroethyl, 2-phenylethyl, benzyl, i-propyl, 4-nitrobenzyl, 4-fluorobenzyl, cyclohexylmethyl, (1-methylindol-3-yl)methyl, (5-methylindol-3-yl)

methyl, (5-fluoroindol-3-yl)methyl, (pyridin-4-yl)methyl, (benzothiazol-2-yl)methyl, (phenyl)(hydroxy)methyl, phenyl, carboxymethyl, 2-carboxyethyl, hydroxymethyl, phenylmethoxymethyl, 4-carboxybenzyl, (benzimidazol-2-yl)methyl, (1-methylsulfonylindol-3-yl)methyl, or (1-ethoxycarbonylindol-3-yl)methyl; $R^{2''}$ is hydrogen atom; $R^{3''}$ is 1,4-phenylene; $R^{4''}$ is a bond; $R^{5''}$ is phenyl, 3-methoxyphenyl, 4-methoxyphenyl, 4-methylphenyl, 4-tert-butylphenyl, 4-trifluoromethylphenyl, 4-fluorophenyl, 4-methylthiophenyl, 4-biphenylyl, 2-thienyl, benzoxazol-2-yl, benzothiazol-2-yl, or tetrazol-2-yl; and Y is as defined above, its optically active substance, their pharmaceutically acceptable salt, or hydrate thereof 7) A compound of the formula V:

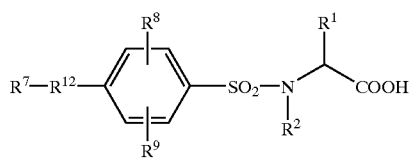

wherein $R^{12}$ is —CH=CH— or —C≡C—; $R^1$, $R^2$, $R^7$, $R^8$, and $R^9$ are as defined above, its optically active substance, their pharmaceutically acceptable salt, or hydrate thereof.

8) A compound of the formula VI:

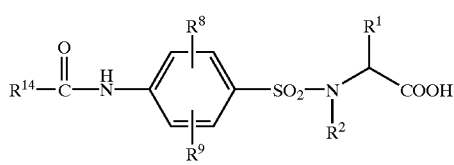

wherein $R^2$, $R^8$, and $R^9$ are as defined above, $R^{13}$ is optionally substituted lower alkyl, optionally substituted aryl, optionally substituted aralkyl, optionally substituted heteroaryl, or optionally substituted heteroarylalkyl; and $R^{14}$ is optionally substituted aryl, or optionally substituted heteroaryl; provided $R^{13}$ is not methyl or phenyl and $R^{14}$ is not 2-chlorophenyl, 4-chlorophenyl, or 2,4-dichlorophenyl, its optically active substance, their pharmaceutically acceptable salt, or hydrate thereof 9) A compound of the formula VII:

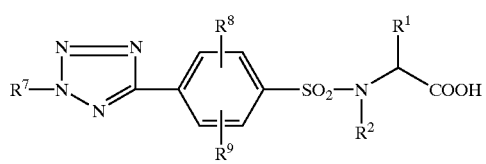

wherein $R^1$, $R^2$, $R^7$, $R^8$, and $R^9$ are as defined above, its optically active substance, their pharmaceutically acceptable salt, or hydrate thereof.

10) A compound of the formula VIII:

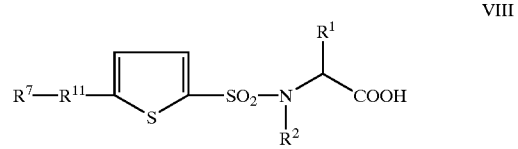

wherein $R^1$, $R^2$, $R^7$, and $R^{11}$ are as defined above, its optically active substance, their pharmaceutically acceptable salt, or hydrate thereof.

11) A compound of the formula VIII:

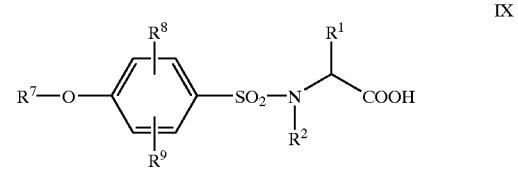

wherein $R^1$, $R^2$, $R^7$, $R^8$, and $R^9$ are as defined above, its optically active substance, their pharmaceutically acceptable salt, or hydrate thereof.

12) A compound of the formula X:

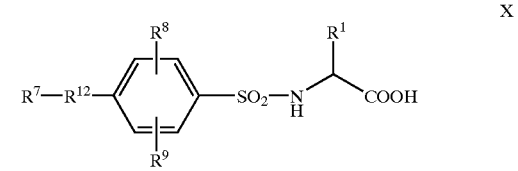

wherein $R^{12}$ is —CH=CH— or —C≡C—; $R^1$, $R^7$, $R^8$, and $R^9$ are as defined above, its optically active substance, their pharmaceutically acceptable salt, or hydrate thereof.

13) A compound of the formula XI:

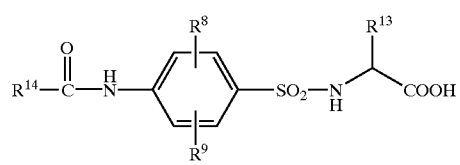

wherein $R^8$, $R^9$, $R^{13}$, and $R^{14}$ are as defined above, provided $R^{13}$ is not methyl or phenyl and $R^{14}$ is not 2-chlorophenyl, 4-chlorophenyl, or 2,4-dichlorophenyl, its optically active substance, their pharmaceutically acceptable salt, or hydrate thereof.

14) A compound of the formula XII:

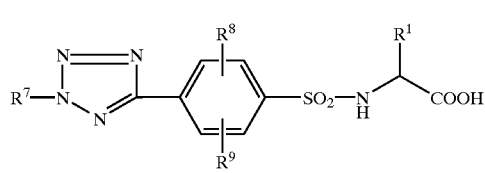

wherein $R^1$, $R^7$, $R^8$, and $R^9$ are as defined above, its optically active substance, their pharmaceutically acceptable salt, or hydrate thereof.

15) A compound of the formula XIII:

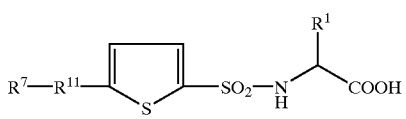

XIII wherein $R^1$, $R^7$, and $R^{11}$ are as defined above, its optically active substance, their pharmaceutically acceptable salt, or hydrate thereof.

16) A compound of the formula XIV:

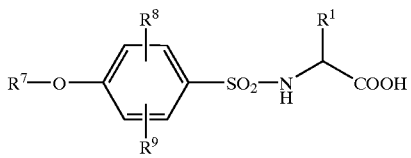

XIV wherein $R^1$, $R^7$, $R^8$, and $R^9$ are as defined above, its optically active substance, their pharmaceutically acceptable salt, or hydrate thereof.

A compound of the invention is more specifically illustrated below:

A) The compound of any one of above 1) to 16), wherein $R^1$, $R^{1'}$, $R^{1''}$, and $R^{13}$ are i-propyl, benzyl, or (indol-3-yl) methyl.

B) The compound of any one of above 1) to 4) and 7) to 16), wherein $R^5$, $R^7$, and $R^{14}$ are phenyl optionally substituted with one or more substituents selected from the group consisting of alkoxy, alkylthio, and alkyl.

C) The compound of any one of above 1) to 16), wherein a configuration of asymmetric carbon atoms bonding with $R^1$, $R^{1'}$, $R^{1''}$, and $R^{13}$ is R configuration.

Further, this invention relates to a pharmaceutical composition, a composition for inhibiting metalloproteinase, and a composition for inhibiting type IV collagenase which contain the compound above 1) to 16) and A) to C)

All of compounds of above 1) to 16) and A) to C) have strong metalloproteinase inhibitory activity, and the following compound is more preferable:

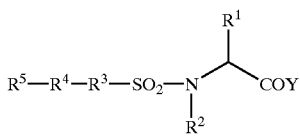

I

1) A compound wherein $R^1$ is i-propyl, benzyl, or (indol-3-yl) methyl, $R^2$ is hydrogen atom, $R^3$ is 1,4-phenylene, $R^4$ is —C≡C—, and $R^5$ is optionally substituted phenyl.

2) A compound wherein $R^1$ is i-propyl, benzyl, or (indol-3-yl) methyl, $R^2$ is hydrogen atom, $R^3$ is optionally substituted 2,5-thiophen-diyl, $R^4$ is —C≡C—, and $R^5$ is optionally substituted phenyl.

3) A compound wherein $R^1$ is i-propyl, benzyl, or (indol-3-yl)methyl, $R^2$ is hydrogen atom, $R^3$ is 1,4-phenylene, $R^4$ is tetrazol-diyl, and $R^5$ is optionally substituted phenyl.

The term "alkyl" herein used means $C_1$–$C_{10}$ straight or branched chain alkyl, example, methyl, ethyl, n-propyl, i-propyl, n-butyl, i-butyl, sec-butyl, tert-butyl, n-pentyl, i-pentyl, neo-pentyl, tert-pentyl, and the like.

The term "lower alkyl" herein used means $C_1$–$C_6$ straight or branched chain alkyl, for example, methyl, ethyl, n-propyl, i-propyl, n-butyl, i-butyl, sec-butyl, tert-butyl, and the like.

The term "$C_3$—$C_8$ cycloalkyl" herein used is exemplified by cyclopropyl, cyclobutyl, cyclopentyl, cyclohexyl, cycloheptyl, and the like.

The term "aryl" herein used means monocyclic or condensed ring aromatic hydrocarbons. Examples of the aryl are phenyl, naphthyl, and the like.

The term "aralkyl" herein used means the above mentioned alkyl substituted by the above mentioned aryl at any possible position. Examples of the aralkyl are benzyl, phenethyl, phenylpropyl (e.g., 3-phenylpropyl), naphthylmethyl (α-naphthylmethyl), anthrylmethyl (9-anthrylmethyl), and the like. Benzyl is preferred. The aryl part may optionally be substituted.

The term "heteroaryl" herein used means a 5 to 6 membered aromatic heterocyclic group which contains one or more hetero atoms selected from the group consisting of nitrogen, oxygen and sulfur atoms in the ring and may be fused with a carbocyclic ring or other heterocyclic ring at any possible position. Examples of the heteroaryl are pyrrolyl (e.g., 1-pyrrolyl), indolyl (e.g., 2-indolyl), carbazolyl (e.g., 3-carbazolyl), imidazolyl (e.g., 4-imidazolyl), pyrazolyl (e.g., 1-pyrazolyl), benzimidazolyl (e.g., 2-benzimidazolyl), indazolyl (e.g., 3-indazolyl), indolizinyl (e.g., 6-indolizinyl), pyridyl (e.g., 4-pyridyl), quinolyl (e.g., 5-quinolyl), isoquinolyl (e.g., 3-isoquinolyl), acridinyl (e.g., 1-acridinyl), phenanthridinyl (e.g., 2-phenanthridinyl), pyridazinyl (e.g., 3-pyridazinyl), pyrimidinyl (e.g., 4-pyrimidinyl), pyrazinyl (e.g., 2-pyrazinyl), cinnolinyl (e.g., 3-cinnolinyl), phthalazinyl (e.g., 2-phthalazinyl), quinazolinyl (e.g., 2-quinazolinyl), isoxazolyl (e.g., 3-isoxazolyl), benzisoxazolyl (e.g., 3-benzisoxazolyl), oxazolyl (e.g., 2-oxazolyl), benzoxazolyl (e.g., 2-benzoxazolyl), benzoxadiazolyl (e.g., 4-benzoxadiazolyl), isothiazolyl (e.g., 3-isothiazolyl), benzisothiazolyl (e.g., 2-benzisothiazolyl), thiazolyl (e.g., 2-thiazolyl), benzothiazolyl (e.g., 2-benzothiazolyl), furyl (e.g., 3-furyl), benzofuryl (e.g., 3-benzofuryl), thienyl (e.g., 2-thienyl), benzothienyl (e.g., 2-benzothienyl), tetrazolyl, and the like. The aryl part of the above heteroaryl is optionally substituted.

The term "heteroarylalkyl" herein used means the above mentioned alkyl substituted with the above mentioned heteroaryl at any possible position. Examples of the heteroarylalkyl are thiazolylmethyl (e.g., 4-thiazolylmethyl), thiazolylethyl (e.g., 5-thiazolyl-2-ethyl), indolylmethyl (e.g., 2-indolylmethyl), imidazolylmethyl (e.g., 4-imidazolylmethyl), benzothiazolylmethyl (e.g., 2-benzothiazolylmethyl), benzopyrazolylmethyl (e.g., 1-benzopyrazolylmethyl), benzotriazolylmethyl (e.g., 4-benzotriazolylmethyl), benzoquinolylmethyl (e.g., 2-benzoquinolylmethyl), benzimidazolylmethyl (e.g., 2-benzimidazolylmethyl), pyridylmethyl (e.g., 2-pyridylmethyl), and the like. The aryl part of the above heteroaryl is optionally substituted.

The term "arylene" herein used is exemplified by phenylene, naphthylene, and the like. Mentioned in more detail, it is exemplified by 1,2-phenylene, 1,3-phenylene,1,4-phenylene, and the like.

The term "heteroarylene" herein used is exemplified by thiophen-diyl,furan-diyl, pyridin-diyl, and the like, in more detail, by 2,5-thiophen-diyl, 2,5-furan-diyl, and the like.

The term "non-aromatic heterocyclic group" herein used means 5 to 6 membered non-aromatic heterocyclic group which contains one or more hetero atoms selected from the group consisting of nitrogen, oxygen and sulfur atoms in the ring, and may bind at any possible position. Examples of the non-aromatic heterocyclic group are morpholino, piperidino, pyrrolidino, and the like.

The term "alkoxy" herein used means alkoxy of which alkyl part is the above mentioned alkyl. Examples of the alkoxy are methoxy, ethoxy, propoxy, butoxy, pentyloxy, and the like.

The term "lower alkoxy" herein used means alkoxy of which alkyl part is the above mentioned lower alkyl. Examples of the lower alkoxy are methoxy, ethoxy, n-propoxy, i-propoxy, n-butoxy, i-butoxy, sec-butoxy, tert-butoxy, and the like.

The term "halogen" herein used means fluoro, chloro, bromo, and iodo.

The term "alkylthio" herein used means alkylthio whose alkyl part is the above mentioned lower alkyl. Examples of the alkylthio are methylthio, ethylthio, and the like.

Substituents for "optionally substituted alkyl", "optionally substituted $C_3-C_8$ cycloalkyl", and "optionally substituted non-aromatic heterocyclic group" are hydroxy, alkoxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkoxycarbonyl (e.g., methoxy-carbonyl and ethoxycarbony), nitro, cyano, haloalkyl (e.g., trifluoromethyl), substituted or unsubstituted amino (e.g., methylamino, dimethylamino, and carbamoylamino), guanidino, phenyl, benzyloxy, and the like. These substituents are able to bind them at one or more of any possible positions.

Substituents for the aromatic ring of "optionally substituted aryr", "optionally substituted aralkyl", "optionally substituted heteroaryl", "optionally substituted heteroarylalkyl", "optionally substituted arylene", and "optionally substituted heteroarylene" are, for example, hydroxy, alkoxy (e.g., methoxy and ethoxy), mercapto, alkylthio (e.g., methylthio), cycloalkyl (e.g., cyclopropyl, cyclobutyl, cyclopentyl), halogen (e.g., fluoro, chloro, bromo, and iodo), carboxy, alkoxycarbonyl (e.g., methoxy-carbonyl and ethoxycarbonyl), nitro, cyano, haloalkyl (e.g., trifluoromethyl), aryloxy (e.g., phenyloxy) substituted or unsubstituted amino (e.g., methylamino, dimethylamino, diethylamino, and benzylidenamino), guanidino, alkyl (e.g., methyl, ethyl, n-propyl, i-propyl, n-butyl, i-butyl, sec-butyl, tert-butyl, n-pentyl, i-pentyl, neo-pentyl, and tert-pentyl), alkenyl (e.g., vinyl and propenyl), alkynyl (e.g., ethynyl and phenylethynyl), alkanoyl (e.g., formyl, acetyl, and propionyl), acyloxy (e.g., acetyloxy), acylamino, alkylsulfonyl (e.g., methylsulfonyl), phenyl, benzyl, an azo group (e.g., phenylazo), optionally substituted heteroaryl (e.g., 3-pyridyl), optionally substituted ureido (e.g., ureido and phenylureido), and the like. These substituents are able to bind to it at one or more of any possible position.

BEST MODE FOR CARRYING OUT THE INVENTION

Compounds (Ia) and (Ib) of the invention are able to be synthesized from the corresponding α-amino acids represented by the formula (XV) by means of the following 6 synthetic methods. Generally, it is possible to produce the compounds of the invention by means of the method A. Each classified type of the compounds is possible to be produced by means of methods the B to F. However, these methods are only examples to produce the compounds represented by the formula I. A compound represented by the formula I produced by any other method is included in this invention.

Method A: A general synthetic method of the compound represented by the formula I.

Method B: A synthetic method of the compound wherein and $R^3$ is optionally substituted arylene or optionally substituted heteroarylene, $R^4$ is —C≡C—, and $R^5$ is optionally substituted aryl or optionally substituted heteroaryl.

Method C: A synthetic method of the compound wherein $R^3$ is optionally substituted arylene or optionally substituted heteroarylene, $R^4$ is a bond, and $R^5$ is optionally substituted aryl or optionally substituted heteroaryl.

Method D: A synthetic method of the compound wherein $R^3$ is optionally substituted arylene or optionally substituted heteroarylene, $R^4$ is —CO—NH—, and $R^5$ is optionally substituted aryl or optionally substituted heteroaryl.

Method E: A synthetic method of the compound wherein $R^3$ is optionally substituted arylene or optionally substituted heteroarylene, $R^4$ is tetrazol-diyl, and $R^5$ is optionally substituted aryl or optionally substituted heteroaryl.

Method F: A synthetic method of the compound wherein $R^3$ is optionally substituted arylene or optionally substituted heteroarylene, $R^4$ is —CH=CH—, and $R^5$ is optionally substituted aryl or optionally substituted heteroaryl.

Details of these methods are explained as follows.

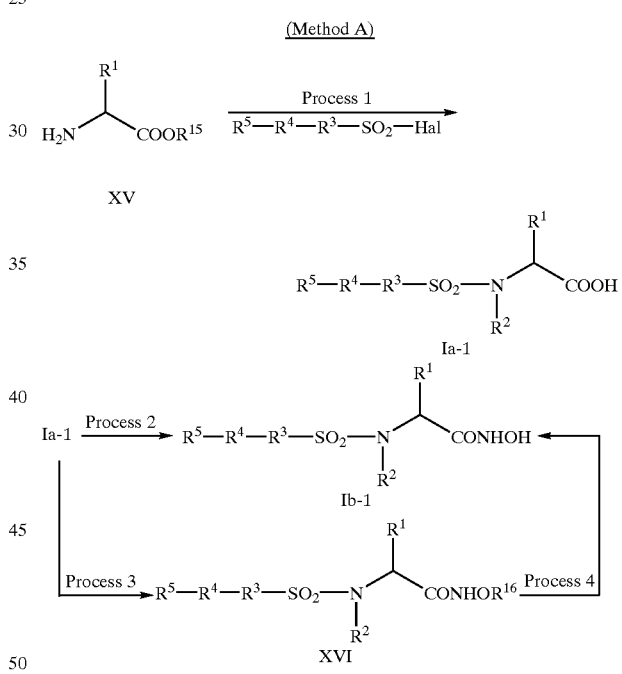

(Method A)

wherein $R^1$, $R^2$, $R^3$, $R^4$, and $R^5$ are as defined above, $R^{15}$ is hydrogen atom or a carboxy protective group, $R^{16}$ is a hydroxy protective group, and Hal is halogen.

Conversion of compound (XV) to compound (Ia-1) is sulfonation of an amino group of the compound (XV) (process 1). If necessary, after this reaction, N-alkylation, deprotection of a carboxyl protective group, etc. are carried out. Conversion of compound (Ia-1) to compound (Ib-1) is to obtain hydroxamic acid derivatives from carboxylic acid derivatives (process 2). To obtain compound (Ib-1) from compound (Ia-1), compound (Ia-1) may also be reacted with hydroxylamine having a hydroxyl protective group or its acidic salts to give compound (XVI) (process 3), followed by and deprotection (process 4). Conversion to sulfonyl derivatives and hydroxamic acid derivatives are able to be carried out according to an usual method. For example, an amino acid represented by the formula (XV) is reacted with a sulfonating agent such as sulfonyl halide represented by $R^5$—$R^4$—$R^3$—$SO_2Hal$ ($R^3$, $R^4$, and $R^5$ are as defined above; and Hal is halogen) and then hydroxylamine. Each process will hereinafter be described in more detail.

(Process 1)

Some of amino acids represented by the formula (XV) or its acidic salts (e.g., hydrochloride, p-toluenesulfonate, and trifluoroacetate) which are starting materials are commercially available. The other are able to be synthesized in accordance with a method described in Zikkenkagakukoza, vol. 22, IV (nihonkagakukai), J. Med. Chem. 38, 1689–1700, 1995, Gary M. sander et. al., etc. some of sulfonating agents are commercially available and the other are synthesized in accordance with a method described Shin-zikkenkagakukoza, vol. 14, 1787, 1978, Synthesis 852–854, 1986, etc. A carboxyl protective group is exemplified by esters (e.g., methyl ester, tert-butyl ester and benzyl ester). Deprotection of this protective group may be carried out by hydrolysis with acid (e.g., hydrochloride and trifluorbacetic acid) or base (e.g., sodium hydroxide) depending on the type of the group, or by catalytic reduction, e.g., under 10% palladium-carbon catalyst condition. To obtain a compound (Ib-1), the esters may directly be converted to hydroxamic acid by the method of process 2. When a compound (XV) is an amino acid wherein $R^{15}$ is hydrogen atom, preferable solvents for this sulfonylation are dimethylformamide, tetrahydrofuran, dioxane, dimethylsulfoxide, acetonitrile, water, or mixed solvents thereof. When a compound (XV) is an amino acid wherein $R^{15}$ is a protective group such as an ester, a solvent for this sulfonylation is exemplified by the above solvents and mixed solvents of water-insoluble solvents (e.g., benzene and dichloromethane) and the above solvents. A base to be used in this sulfonylation is exemplified by organic bases such as triethylamine, N-methylmorpholine, etc. and inorganic bases such as sodium hydroxide, potassium hydroxide, potassium carbonate, and the like. Usually this reaction can be carried out at ice-cooling to room temperature. When $R^1$, $R^3$, $R^4$, $R^5$, or $R^{15}$ of compound (Ia-1) contains a functional group(s) possibly interfering this sulfonylation (e.g., hydroxy, mercapto, amino, and guanidino), it can previously be protected in accordance with a method described in "Protective Groups in Organic Synthesis" (Theodora W. Green (John Wiley & Sons)) and then deprotected at an appropriate process. When $R^2$ is not hydrogen atom, compound (Ia-1) wherein $R^2$ is hydrogen atom is further reacted with haloalkyl (e.g., methyl iodide, and ethyl iodide) or haloaralkyl (e.g., benzyl chloride, and benzyl bromide) in dimethylformamide, tetrahydrofuran, dioxane, and the like at a temperature range of ice-cooling to 80 ° C., preferably ice-cooling to room temperature, for 3–10 hours, preferably 10–20 hours to give the desired N—$R^2$ derivative.

(Process 2)

A hydroxylamine is reacted with compound (Ia-1) or its reactive derivatives to give hydroxamic acid derivatives (Ib-1). A hydroxylamine is usually used as its acidic salts (e.g., hydrochloride, and phosphate, sulfate: commercially available) in the presence of a base. A base to be used in this reaction is exemplified by organic bases such as triethylamine, N, N-dimethylaniline, N-methylmorpholine, etc. and inorganic bases such as sodium hydroxide, potassium hydroxide, potassium carbonate, etc. When compound (Ia-1) is used as a starting material of conversion to hydroxamic acid, this reaction is carried out in the presence of a peptide condensing agent (e.g., dicyclohexylcarbodiimide, 1-ethyl-3-(3-dimethylaminopropyl)carbodiimide, N,N'-carbonyldiimidazole, or a mixture of one of the above agents with 1-hydroxybenzotriazole, N-hydroxy sucinicimide, etc.). A solvent for this reaction may be dimethylformamide, tetrahydrofuran, dioxane, dimethylsulfoxide, acetonitrile, water, and mixed solvent thereof This reaction is carried out at –20° C. to 40° C., preferably ice-cooling to room temperature, for 1 to 16 hours.

Acid anhydrides (especially, mixed acid anhydrides), acid halides, acid azides, and esters can be utilized in this reaction as a reactive derivative of compound (Ia-1). These reactive derivatives are produced by usual methods. For example, the acid anhydride derivatives can be produced by a reaction of compound (Ia-1) with acid halide derivatives (e.g., ethyl chlorocarbonate) in the presence of a base (e.g., triethylamine), and acid halide derivatives can be produced by a reaction of compound (Ia-1) with a halogenation agent (e.g., oxalylchloride, and thionylchloride). Ester derivatives may be inactive or active. Sulfonyl derivatives converted from a compound (XV) wherein $R^{15}$ is a carboxyl protective groups (e.g., methyl, tert-butyl, and benzyl) at process 1 can be used as inactive esters without deprotection. Active esters can be produced by a reaction of compound (Ia-1), carbodiimide reagents (e.g., dicyclohexylcarbodiimide, 1-ethyl-3-(3-dimethylaminopropyl)carbodiimide), and hydroxy derivatives corresponding to the active ester residue such as 1-hydroxybenzotriazole, N-hydroxysuccinimide, or the like. A reaction condition of conversion of the reactive derivatives of compound (Ia-1) to hydroxamic acid may be the same as that of conversion of compound (Ia-1) itself to hydroxamic acid. The reactions of processes 1 and 2 are able to continuously be carried out in one-pot reaction.

(Process 3)

A protected hydroxylamine to be used in this reaction includes O-benzylhydroxylamine, O-(p-methoxybenzyl)hydroxylamine, O-(tert-butyl)hydroxylamine, or the like. This reaction condition may be in the same manner as that of process 2.

(Process 4)

This process for deprotection is carried out by catalytic reduction, treatment with conc. hydrochloric acid, or treatment with trifluoroacetic acid to give the desired compound (Ib-1). The compounds of this invention (Ia-1) and (Ib-1) can be isolated and purified by usual separation methods and purification methods (e.g., chromatography, crystallization, etc.).

(Method B)

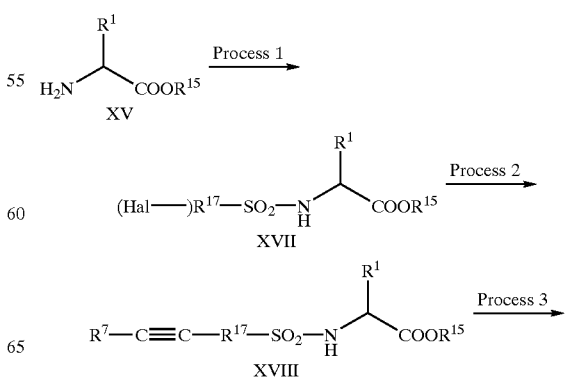

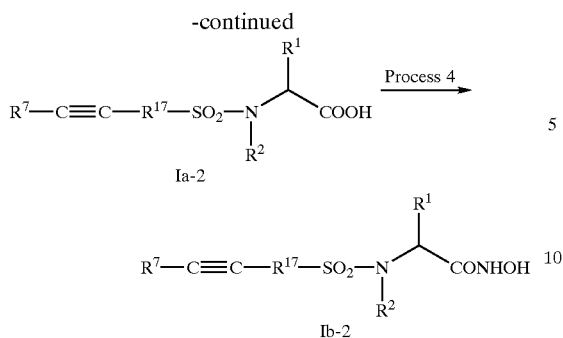

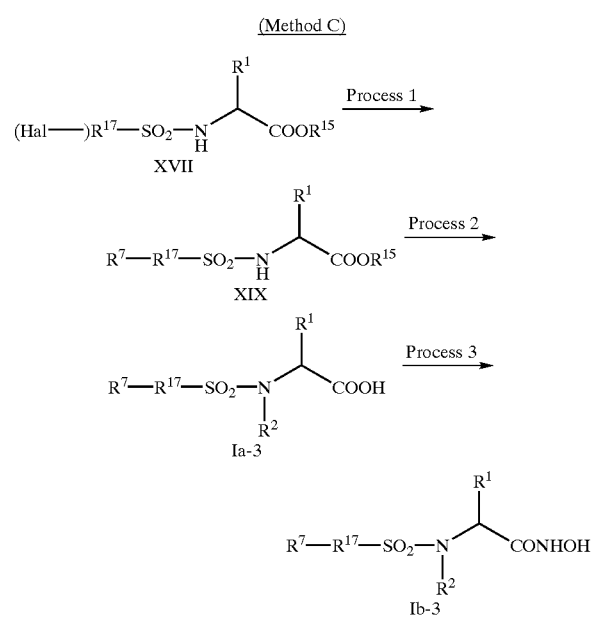

wherein $R^1$, $R^2$, $R^7$, $R^{15}$, and Hal are as defined above, $R^{17}$ is optionally substituted aryl or optionally substituted heteroaryl.

Conversion of compound (XV) to compound (XVII) is performed by sulfonation of an amino group of compound (XV) (process 1) in the same manner as that described in process 1 of method A. Conversion of compound (XVII) to compound (XVIII) is performed by Heck reaction (K. Sonogashira, Y. Tohda, and N. Hagihara, Tetrahedron Lett., 4467(1975) etc.) wherein halogen of $R^{17}$ is utilized to insert a triple bond (process 2). Conversion of compound (XVIII) to compound (Ia-2) is N-alkylation, deprotection of a carboxyl protective group, etc. (process 3), which can be carried out in the same manner as that described in process 1 of method A. Conversion of compound (Ia-2) to compound (Ib-2) is that of carboxylic acid derivatives to hydroxamic acid derivatives (process 4), which can be carried out in the same manner as those described in processes 2 to 4 of method A. Each process will hereinafter be described in more detail.

(Process 1)

This process may be carried out in the same manner as that described in process 1 of method A.

(Process 2).

Compound (XVII) is reacted with optionally substituted aryl or optionally substituted heteroaryl having an ethynyl group such as ethynylbenzene in a solvent such as dimethylformamide, toluene, xylene, benzene, tetrahydrofuran etc. in the presence of a palladium catalyst (e.g., $Pd(Ph_3P)_2Cl_2$), a divalent copper reagent (e.g., CuI), and an organic base (e.g., triethylamine, and diisopropylethylamine) to give a desired compound (XVIII) (Heck reaction). This reaction is carried out at room temperature to 100° C., preferably room temperature to 80° C. This reaction is completed for 3 to 30 hours, preferably 10 to 20 hours. When optionally substituted aryl or optionally substituted heteroaryl has a substituent(s) interfering this reaction, the substituent(s) can previously be protected in accordance with a method of "Protective Groups in Organic Synthesis" (Theodora W. Green (John Wiley & Sons)), and then deprotected at an appropriate step.

(Process 3)

This process may be carried out in the same manner as that described in process 1 of method A.

(Process 4)

This process may be carried out in the same manner as those described in processes 2 to 4 of method A.

wherein $R^1$, $R^2$, $R^7$, $R^{15}$, $R^{17}$, and Hal are as defined above.

Conversion of compound (XVII) to compound (XIX) is performed by Suzuki reaction (M. J. Sharp and V. Shieckus, Tetrahedron Lett., 26, 5997 (1985) etc.) wherein halogen of $R^{17}$ is utilized to introduce aryl or heteroaryl (process 1). Conversion of compound (XIX) to compound (Ia-3) is N-alkylation, deprotection of a carboxyl protective group, etc. (process 2) and this process can be carried out in the same manner as that described in process 1 of method A. Conversion of compound (Ia-3) to. compound (Ib-3) is that of carboxylic acid derivatives to hydroxamic acid derivatives (process 3), and this process can be carried out in the same manner as those described in processes 2 to 4 of method A. Each process will hereinafter be described in more detail.

(Process 1)

Compound (XVII) is reacted with optionally substituted aryl or optionally substituted heteroaryl having a $B(OH)_2$ (otherwise $B(Et)_2$) group such as phenylboronic acid in a solvent such as dimethylformamide, toluene, xylene, benzene, tetrahydrofuran etc. in the presence of a palladium catalyst (e.g., $Pd(Ph_3P)_4$) and a base (e.g., potassium carbonate, calcium carbonate, triethylamine, sodium methoxide etc.) to give the desired compound (XIX) (Suzuki reaction). This reaction is carried out at room temperature to 100° C., preferably room temperature to 80° C. This reaction is completed for 5 to 50 hours, preferably 15 to 30 hours. When optionally substituted aryl or optionally substituted heteroaryl has a substituent(s) interfering this reaction, the substituent(s) can previously be protected in accordance with a method of "Protective Groups in Organic Synthesis" (Theodora W. Green (John Wiley & Sons)) and then deprotected at an appropriate step.

(Process 2)

This process may be carried out in the same manner as that described in process 1 of method A.

(Process 3)

This process may be carried out in the same manner as those described in processes 2 to 4 of method A.

(Method D)

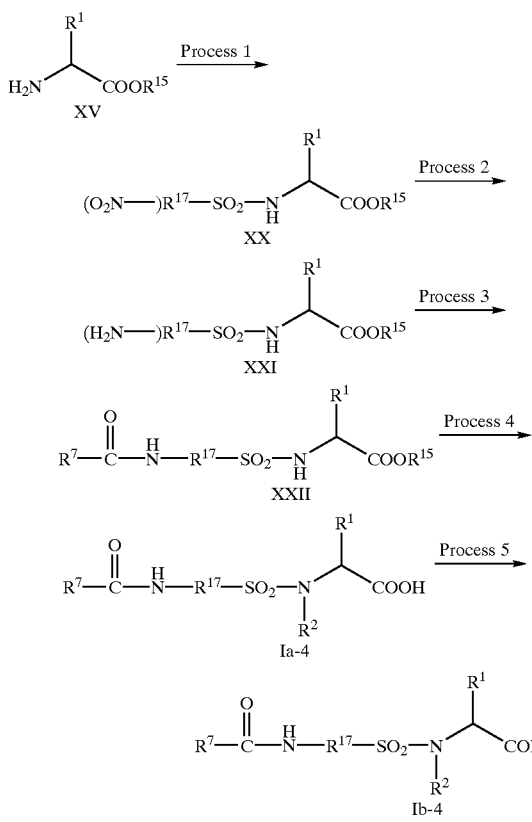

(Process 3)
Compound (XXI) is reacted with optionally substituted aryl or optionally substituted heteroaryl having an acid halide (otherwise an active ester) group such as benzoyl chloride in a solvent such as dimethylformamide, tetrahydrofuran, dioxane, dimethylsulfoxide, acetonitrile, xylene, toluene, benzene, dichloromethane, etc. in the presence of a base (e.g., triethylamine, N-methylmorpholine, potassium carbonate etc.) to give the desired compound (XXII). This reaction is carried out at a temperature under ice-cooling to 100° C., preferably room temperature to 60° C., and is completed for 3 to 30 hours, preferably 10 to 25 hours.
(Process 4)
This process may be carried out in the same manner as that described in process 1 of method A.
(Process 5)
This process may be carried out in the same manner as those described in processes 2 to 4 of method A.
(Method E)

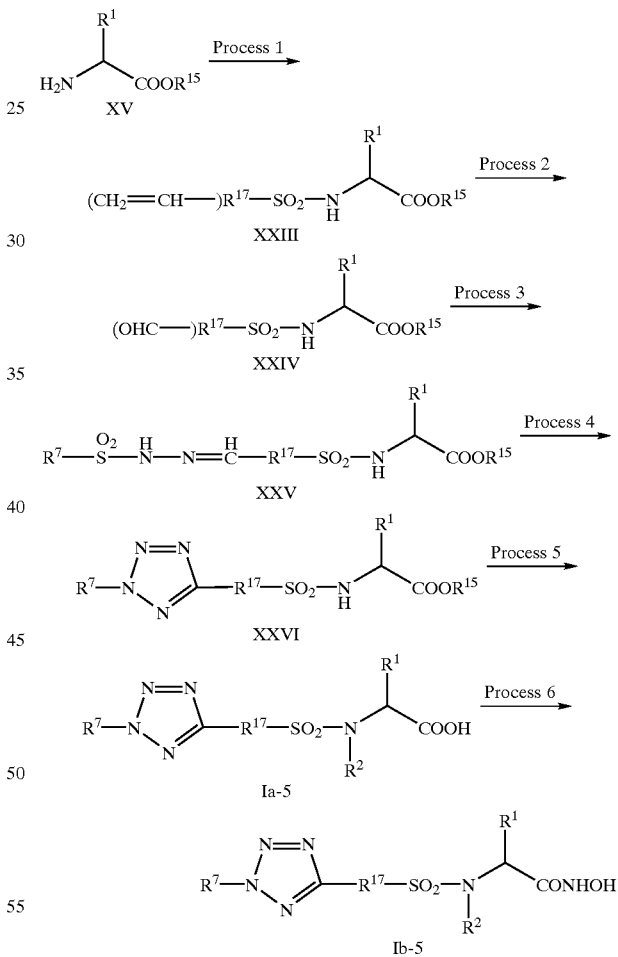

wherein $R^1$, $R^2$, $R^7$, $R^{15}$, $R^{17}$, and Hal are as defined above.

Conversion of compound (XV) to compound (XX) is sulfonation of an amino group of the compound (XV) (process 1) and this process may be carried out in the same manner as that described in process 1 of method A. Conversion of compound (XX) to compound (XXI) is reduction of a nitro group of $R^{17}$ to an amino group (process 2) and this process can be carried out by catalytic reduction or other reduction using hydrochloric chloride—Fe, hydrochloric chloride—Sn, etc. Conversion of compound (XXI) to compound (XXII) is performed by usual amide bond formation reaction wherein an amino group of $R^{17}$ is utilized (process 3). Conversion of compound (XXII) to compound (Ia-4) is N-alkylation, deprotection of a carboxyl protective group, etc. (process 4) of compound (XXII) and this process can be carried out in the same manner as that described in process 1 of method A. Conversion of compound (Ia-4) to compound (Ib-4) is that of carboxylic acid derivatives to hydroxamic acid derivatives (process 5) and this process can be carried out in the same manner as those described in processes 2 to 4 of method A. Each process will hereinafter be described in more detail.
(Process 1)
This process may be carried out in the same manner as that described in process 1 of method A.
(Process 2)
Compound (XX) is treated with hydrogen in a solvent such as methanol, ethanol, ethyl acetate, acetic acid, etc. in the presence of a catalyst (e.g., Pd—C, PtO$_2$, Raney Ni etc.), under a no-pressure or pressured condition to give the desired compound (XXI). This reaction is carried out at a temperature under ice-cooling to 80° C., preferably room temperature to 50° C., and is completed for 1 to 10 hours, preferably 2 to 5 hours.

wherein $R^1$, $R^2$, $R^7$, $R^{15}$, $R^{17}$, and Hal are as defined above.

Conversion of compound (XV) to compound (XXIII) is performed by sulfonating an amino group of the compound (XV) (process 1) in the same manner as that described in process 1 of method A. Conversion of compound (XXIII) to compound (XXIV) is done by the reduction wherein an ethenyl group of $R^{17}$ is converted into an aldehyde group (process 2). Conversion of compound (XXIV) to compound (XXVI) is performed by a tetrazole ring formation reaction (processes 3 and 4). Conversion of compound (XXVI) to compound (Ia-5) is N-alkylation, deprotection of a carboxyl protective group, etc. of compound (XXVI) (process 5), and this process can be carried out in the same manner as that described in process 1 of method A. Conversion of compound (Ia-5) to compound (Ib-5) is that of carboxylic acid derivatives to hydroxamic acid derivatives (process 6), which can be carried out in the same manner as those described in processes 2 to 4 of method A. Each process will hereinafter be described in more detail.

(Process 1)

This process may be carried out in the same manner as that described in process 1 of method A.

(Process 2)

A compound (XXIII) is treated with ozone in a solvent such as dichloromethane, ethyl acetate, methanol, etc. to form an ozonide, and then a reagent such as zinc-acetic acid, triethylphosphate, dimethylsulfide, etc. is added to this reaction mixture for reduction to give the desired aldehyde derivatives (XXIV) The reduction can also be carried out by catalytic hydrogenation. This reaction is carried out at $-100°$ C. to room temperature, preferably $-78°$ C. to a temperature under ice-cooling, and is completed for 0.5 to 10 hours, preferably 1 to 3 hours.

(Process 3)

A compound (XXIV) is reacted with benzensulfonylhydrazide in a solvent such as tetrahydrofuran, ether, etc. mixed with a solvent such as methanol, ethanol, etc. to give the desired compound (XXV). This reaction is carried out at a temperature under ice-cooling to 80° C., preferably room temperature to 50° C., and is completed for 3 to 30 hours, preferably 10 to 20 hours.

(Process 4)

Optionally substituted aryl or optionally substituted heteroaryl having amino group such as aniline is dissolved in a mixed solvent such as alcohol (e.g., ethanol) and water. To this mixture conc. hydrochloric acid and a diazotizing agent such as a sodium nitrite aqueous solution are added at $-20°$ C. to 10° C., preferably 0° C. to 5° C., to give a diazonium salt. The reaction time is 5 min to 1 hr, preferably 10 to 30 min. This reaction mixture is added to a pyridine solution of compound (XXV) and allowed react for 1 to 10 hr, preferably 2 to 5 hr, at $-30°$ C. to 50° C., preferably $-15°$ C. to room temperature to give the desired compound (XXVI). When optionally substituted aryl or optionally substituted heteroaryl has a substituent(s) interfering this reaction, the substituent(s) can previously be protected in accordance with a method of a "Protective Groups in Organic Synthesis" (Theodora W. Green (John Wiley & Sons)), and then deprotected at an appropriate step.

(Process 5)

This process may be carried out in the same manner as that described in process 1 of method A.

(Process 6)

This process may be carried out in the same manner as those described in processes 2 to 4 of method A.

(Method F)

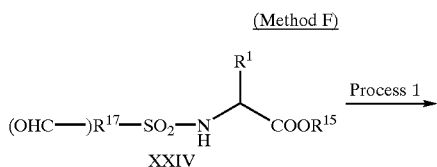

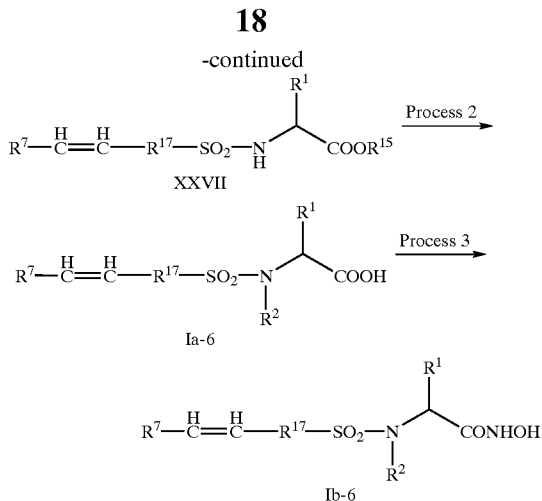

wherein $R^1$, $R^2$, $R^7$, R15, $R^{17}$, and Hal are as defined above.

Conversion of compound (XXIV) to compound (XXVII) is performed by Wittig reaction (G. Wittig et al., Chem. Berr. 87, 1318 (1954)) wherein an aldehyde group of $R^{17}$ is utilized to introduce aryl or heteroaryl through a double bond (process 1). Conversion of compound (XXVII) to compound (Ia-6) is N-alkylatibn, deprotection, etc. of compound (XXVII) process 2), and this process can be carried out the same similar as described in process 1 of method A. Conversion of compound (Ia-6) to compound (Ib-6) is that of carboxylic acid derivatives to hydroxamic acid derivatives (process 3), and this process can be carried out in the same manner as those described in processes 2 to 4 of method A. Each process will hereinafter be described in more detail.

(Process 1)

Compound (XXIV) is reacted with ylide derivatives of optionally substituted aryl or optionally substituted heteroaryl such as $Ph_3P=CHPh$, etc., which is produced by an usual method, in a solvent such as toluene, xylene, tetrahydrofuran, ether, dimethylformamide, etc. at $-100$ to room temperature, preferably $-78°$ C. to ice-cooling for 1 to 20 hours, preferably 1 to 5 hours, to give the desired compound (XXVII). When optionally substituted aryl or optionally substituted heteroaryl has a substituent(s) interfering this reaction, the substituent(s) can previously be protected in accordance with a method of "Protective Groups in Organic Synthesis" (Theodora W. Green (John Wiley & Sons)), and deprotected at an appropriate step.

(Process 2)

This process may be carried out in the same manner as that described in process 1 of method A.

(Process 3)

This process may be carried out in the same manner as those described in processes 2 to 4 of method A.

The term "compound of the present invention" herein used includes pharmaceutically acceptable salt or hydrate of the compound. The salt is exemplified by a salt with alkali metals (e.g., lithium, sodium, and potassium), alkaline earth metals (e.g., magnesium and calcium), ammonium, organic bases, amino acids, mineral acids (e.g., hydrochloric acid, hydrobromic acid, phosphoric acid, and sulfuric acid), or organic acids (e.g., acetic acid, citric acid, mallein acid, fumaric acid, benzenesulfonic acid, and p-toluenesulfonic acid). These salts can be formed by the usual method.

The compound of the present invention is not restricted to any particular isomers but includes all possible isomers and racemic modifications.

The compound of the present invention has an excellent activity for inhibiting metalloproteinase, especially activity for inhibiting MMP, and inhibits matrix dissolution, as described in the following test example. Therefore, the compound of the present invention is useful to treat or prevent diseases which are caused by MMP and relative enzymes such as TNF-α converting enzyme, etc.

Definitely, the compounds of the present invention are useful in the prevention or treatment of diseases such as osteoarthritis, rheumatoid arthritis, corneal ulceration, periodontal disease, metastasis and invasion of tumor, advanced virus infection (e.g., HIV), arteriosclerosis obliterans, arteriosclerotic aneurysm, atherosclerosis, restenosis, sepsis, septic shock, coronary thrombosis, aberrant angiogenesis, scleritis, multiple sclerosis, open angle glaucoma, retinopathies, proliferative retinopathy, neovascular glaucoma, pterygium, keratitis, epidermolysis bullosa, psoriasis, diabetes, nephritis, neurodegengerative disease, gingivitis, tumor growth, tumor angiogenesis, ocular tumor, angiofibroma, hemangioma, fever, hemorrhage, coagulation, cachexia, anorexia, acute infection, shock, autoimmune disease, malaria, Crohn disease, meningitis, and gastric ulcer.

When the compound of the present invention is administered to a person for treatment or prevention of the above diseases, they can be administered by oral administration such as powder, granules, tablets, capsules, pilulae, and liquid medicine, or by parenteral administration such as injections, suppository, percutaneous formulations, insufflation, or the like. An effective dose of the compound of the invention is formulated by being mixed with medicinal admixture such as excipient, penetrant, disintegrators, lubricant, and the like if necessary. When parenteral injection is prepared, the compound of the invention and an appropriate carrier are sterilized to prepare it.

An appropriate dosage varies with the conditions of the patients, an administration route, their age, their body weight and the like and should be determined by a physician in the end. In the case of oral administration, a daily dosage can generally be between 0.1–100 mg/kg/day, preferably 1–20 mg/kg/day. In the case of parenteral administration, the daily dosage can generally be between 0.01–10 mg/kg/day, preferably 0.1–1 mg/kg/day. The daily dosage can be administrated in one to several divisions.

The following examples are provided to further illustrate the present invention and are not to be constructed as limiting the scope thereof.

Abbreviations described below are used in the following examples.

p-TsOH: p-toluenesulfonic acid
DMSO dimethylsulfoxide
Me: methyl
$^t$Bu: tert-butyl Example 1 (Method A)

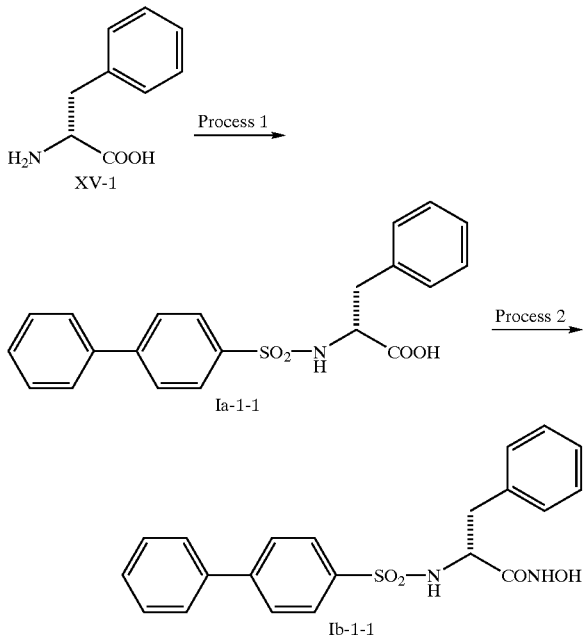

To a suspension of (R)-(+)-phenylalanine (compound XV-1, 1.65 g (10 mmol)) in 50 ml of dimethylformamide and 35 ml of water was stirred and treated with 2.78 ml (20 mmol) of triethylamine under ice-cooling. Then, 2.52 g (10 mmol) of 4-biphenylsulfonyl chloride in 10 ml of dimethylformamide was added dropwise to the mixture over 5 min. After the reaction mixture was stirred for 2 h at the same temperature, 1.35 g (10 mmol) of 1-hydroxybenzotriazole hydrate, 2.1 g (11 mmol) of 1-ethyl-3-(3-dimethylaminopropyl)carbodiimide hydrochloride, 3.47 g (50 mmol) of hydroxylamine hydrochloride, and 7 ml (50 mmol) of triethylamine were added to the mixture. After being stirred for 16 h at room temperature, the reaction mixture was poured into water and extracted with ethyl acetate. The organic layer was washed with 2N HCl, 5% NaHCO$_3$, and water, and concentrated in vacuo. The residue was subjected to silica gel column chromatography and the fractions eluting with CHCl$_3$/MeOH=40/1 to 20/1 were collected to yield 1.70 g of compound (Ib-1-1) as a foam.

Yield 43%. mp. 169–170° C. Elemental analysis (%) C$_{21}$H$_{20}$N$_2$O$_4$S; Calcd. : C;63.62, H;5.08, N;7.07, S;8.09; Found: C;63.61, H;5.12, N;6.98, S;8.06; IR ν max (cm$^{-1}$)

(Nujol): 3365, 3295, 3266, 1674, 1320, 1159. NMR (δ ppm)$d_6$-DMSO: 2.61 (dd, J=8.6, 13.4Hz, 1H), 2.80 (dd, J=6.0, 13.6Hz, 1H), 3.80 (m, 1H). $[\alpha]_D$: +18.5±1.2 (c=0.503%, 25° C., DMSO).

Example 1'

Another synthetic method of compound (Ib-1-1)

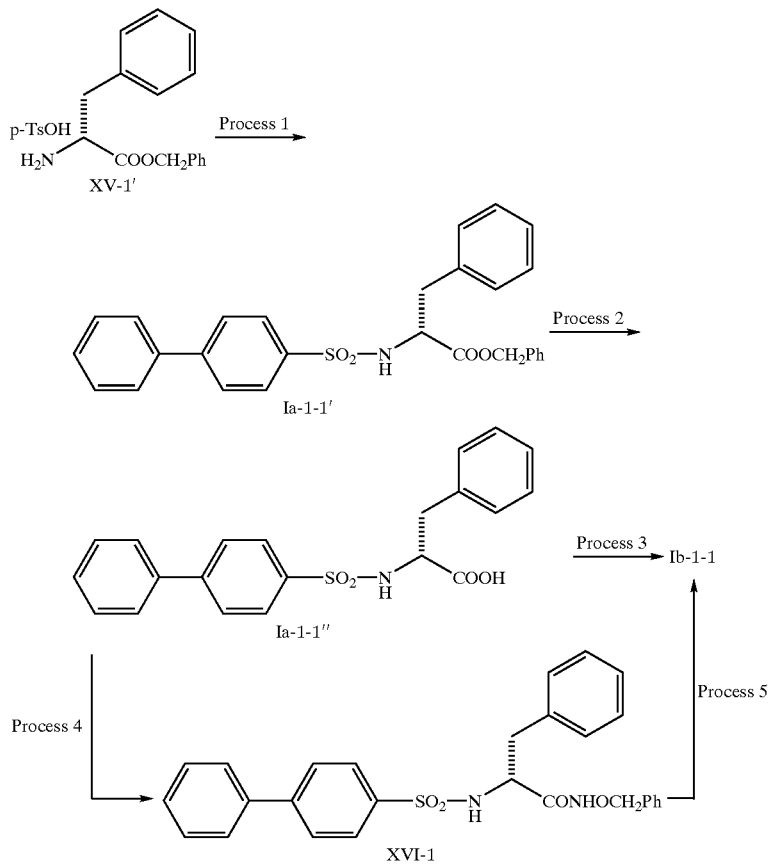

Process 1

To a solution of (R)-phenylalanine benzyl ester tosylate (compound XV-1', 2.5 g (5.85 mmol)) in 60 ml of dichloromethane was added triethylamine (1.8 ml, 12.87 mmol) and 4-biphenylsulfonyl chloride(1.63 g, 6.44 mmol) under ice-cooling. After being stirred for 2 h at room temperature, the reaction mixture was washed with 2N HCl, 5% $NaHCO_3$ and water, and concentrated in vacuo. The residue was subjected to silica gel column chromatography and the fractions eluting with $CHCl_3$/MeOH=40/1 to 20/1 were collected and crystallized from dichloromethane/hexane to give 2.32 g of compound (Ia-1-1'). Yield 84.1%. mp. 130–131° C.

Elemental analysis (%) $C_{28}H_{25}NO_4S$ Calcd.: C; 71.32, H; 5.34, N; 2.97, S; 6.80; Found: C; 71.05, H; 5.41, N; 3.00, S; 6.81; IR ν max ($cm^{-1}$) (Nujol): 3352, 1732, 1341, 1190, 1163. NMR (δ ppm) ($CDCl_3$): 3.06 (d, J=5.8Hz, 2H), 4.30 (dt, J=6.0, 9.0Hz, 1H), 4.89 (s, 2H), 5.12 (d, J=9.0Hz, 1H), 6.98–7.81 (m, 14H). $[\alpha]_D$: −16.4±1.1(c=0.506%, 25° C., MeOH).

Process 2

A solution of compound (Ia-1-1') (2.28 g) which was obtained process 1 in 50 ml of mixed solvents of methanol/ethyl acetate=1/1, was hydrogenated using 10% Pd/C (200 mg) for 25 min. The reaction mixture was filtered off, and the filtrate was concentrated in vacuo. The residue was recrystallized from dichloromethane/hexane to give 1.83 g of compound (Ia-1-1"). Yield 99.1%. mp. 146–147° C.

Elemental analysis (%) $C_{21}H_{19}NO_4S$ Calcd.: C; 66.12, H; 5.02, N; 3.67, S; 8.41; Found: C; 65.97, H; 5.06, N; 3.61, S; 8.48; IR ν max ($cm^{-1}$) (Nujol) : 3408, 3305, 1751, 1325, 1161, 1134. NMR (δ ppm) ($CDCl_3$): 2.97 (dd, J=7.0, 13.8Hz, 1H), 3.14 (dd, J=5.2, 14.0Hz,1H), 4.13 (m, 1H), 7.03–7.78 (m, 14H). $[\alpha]_D$: −4.0±0.4(c=1.000%, 25° C., MeOH).

Process 3

To a solution of compound (Ia-1-1", 1.0 g (2.62 mmol)) which was obtained process 2 in dichloromethane (20 ml) was added 0.33 ml (3.93 mmol) of oxalyl chloride and one drop of dimethylformamide. After being stirred for stirred for 1 h at room temperature, the reaction mixture was concentrated in vacuo. The residue was dissolved in 10 ml of tetrahydrofuran. A solution of hydroxylamine hydrochloride (911 mg (13.1 mmol)) and $NaHCO_3$ 1.54 g (18.34 mmol)) in 10ml of tetrahydrofuran and 10 ml of water was stirred for 5 min under ice-cooling. To the mixture was added the above solution of acid chloride in tetrahydrofuran and the resulting mixture was stirred for 30 min. The reaction mixture was poured into water, and extracted with ethyl acetate. The organic layer was washed with 5% $NaHCO_3$, and water, and concentrated in vacuo to give compound (Ia-1) (969 mg). Yield 93.3%.

Process 4

To a solution of compound (Ia-1-1", 2.0 g, 5.24 mmol) which was obtained process 2 in dimethylformamide (20 ml) was added 1-hydroxybenzotriazole hydrate (0.7 g, 5.24 mmol), N-methylmorpholine (2.9 ml, 26.2 mmol), 1-ethyl-3-(3-diisopropylamino) carbodiimide hydrochloride (8 mmol), and O-benzylhydroxylamine hydrochloride (1.67 g, 10.48 mmol), and the resulting mixture was stirred for 6 h at room temperature. The reaction mixture was poured into water and extracted with ethyl acetate. The organic layer was washed with 2N HCl, 5% NaHCO$_3$, and water, and concentrated in vacuo. The residue was subjected to silica gel column chromatography and the fractions eluting with CH$_2$Cl$_2$/hexane=1/1 were collected and recrystallized from dichloromethane/hexane to give 2.04 g of compound (XVI-1).

Yield 80%. mp. 171–173° C. Elemental analysis (%) C$_{28}$H$_{26}$N$_2$O$_4$S; Calcd.:C; 69.12, H; 5.39, N; 5.76, S; 6.59; Found :C; 68.85, H; 5.46, N; 5.76, S; 6.78; IR ν max (cm$^{-1}$) (Nujol) : 3248, 1661, 1594, 1333, 1163. NMR (δ ppm) (CDCl$_3$): 2.85–3.60 (m, 2H), 3.86 (m, 1H), 4.77 (ABq-Apart, J=11.4Hz, 1H), 4.82 (ABq-Bpart, J=11.4Hz, 1H), 5.00 (m, 1H), 6.95–7.70 (m, 19H). [α]$_D$: −40.2±1.6 (c=0.505%, 25° C., DMSO).

Process 5

A solution of compound (XVI-1) (1.97 g) which was obtained process 4 in a 60 ml of mixed solvents of methanol/ethyl acetate=1/1 was hydrogenated using 10% Pd-C (200 mg) for 3.5 h. The reaction mixture was filtered off, and the filtrate was concentrated in vacuo. The residue was recrystallized from dichloromethane/hexane to give 1.35 g of compound (Ib-1-1). Yield 84.4%.

Example 2–91

The compounds which were shown in Tables 1 to 22 were synthesized in a manner similar to those described in Example 1'

TABLE 1

(Ib)

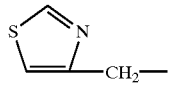

| Example No. | R$^1$ | R$^{18}$ | * | mp (decomp.) (° C.) | IR (ν cm$^{-1}$) (KBr) | $^1$H-NMR(δ ppm) d$_{6\text{-DMSO}}$ |
|---|---|---|---|---|---|---|
| 2 | 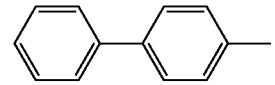 | 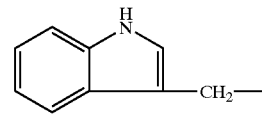 | RS | 173> | 3258,1650,1377, 1348,1163 (Nujol) | 2.87(dd, J=5.6, 14.2Hz, 1H), 2.98(dd, J=8.4, 14.2Hz, 1H), 4.02(dd, J=2.2, 8.6Hz, 1H), 7.24(d, J=2.0Hz, 1H), 8.83(d, J=2.2Hz, 1H) |
| 3 | 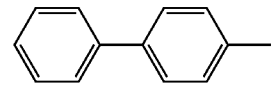 | 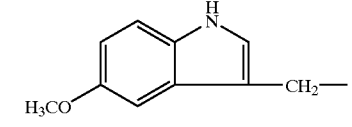 | R | 203–206 | 3403,3386,3265,1673, 1320,1162 (Nujol) | 2.72(dd, J=7.2, 13.8Hz, 1H), 2.97(dd, 7.0, 14.8Hz, 1H), 3.81(m, 1H), |
| 4 | 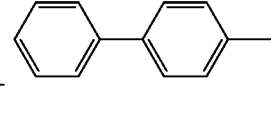 | 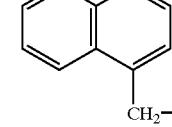 | RS | — | — | — |
| 5 | 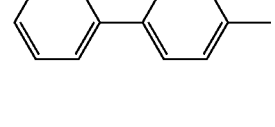 | 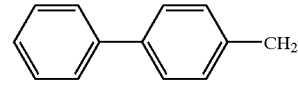 | RS | 124–128 | 3277,1669,1397, 1322,1159, | 3.12(dd, J=10.3, 14.3Hz, 1H), 3.89(dd, J=3.3, 13.5Hz, 1H), 4.20(m, 1H), 5.90 (brs, 1H) |
| 6 | 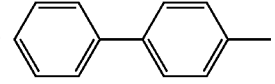 | 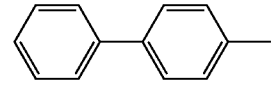 | R | 139–141 | 3262,1663,1322, 1157, | 2.67(dd, J=9.2, 13.1Hz, 1H), 2.84(dd, J=5.3, 13.5Hz, 1H), 3.82(m, 1H) |
| 7 | CF$_3$CH$_2$— | 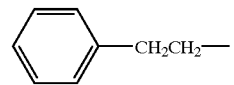 | R | 167–169 | 3265,1676,1642, 1337,1161 (Nujol) | 2.2–2.7(m, 2H),3.99(t, J=7.0Hz, 1H) |
| 8 | 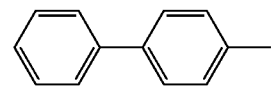 | | RS | 172–173 | 3403,3261,1669, 1321,1160 | 1.68(m, 2H), 2.37(m, 2H), 3.64(t, J=6.9Hz, 1H) |

TABLE 1-continued (Ib)
$$R^{18}SO_2NH-\overset{R^1}{\underset{*}{C}H}-CONHOH$$

| Example No. | R$^1$ | R$^{18}$ | * | mp (decomp.) (°C.) | IR ($\nu$ cm$^{-1}$) (KBr) | $^1$H-NMR($\delta$ ppm) d$_6$-DMSO |
|---|---|---|---|---|---|---|
| 9 | benzyl (C$_6$H$_5$–CH$_2$–) | 4-Br-C$_6$H$_4$– | R | 144–146 | 3700–2200br,3264, 1635,1342,1164, | 2.61(dd, J=9.4, 13.8Hz, 1H), 2.78(dd, J=6.0, 13.8Hz, 1H), 3.78(m, 1H), 7.43(d, J=8.2Hz, 2H), 7.60(d, J=8.2Hz, 2H), |

TABLE 2

(Ib)
$$R^{18}SO_2NH-\overset{R^1}{\underset{*}{C}H}-CONHOH$$

| Example No. | R$^1$ | R$^{18}$ | * | mp (decomp.) (°C.) | IR ($\nu$ cm$^{-1}$) (KBr) | $^1$H-NMR($\delta$ ppm) d$_6$-DMSO |
|---|---|---|---|---|---|---|
| 10 | benzyl (C$_6$H$_5$–CH$_2$–) | 4-F$_3$C-C$_6$H$_4$– | R | 116–118 | 3600–2400br,3257, 1743,1721,1323,1132, | 2.60–2.82(m, 2H), 3.84(m, 1H), 7.00–7.18(m, 5H), 7.62–7.80(m, 4H), |
| 11 | benzyl (C$_6$H$_5$–CH$_2$–) | 5-(CH$_3$)$_2$N-naphthalen-1-yl | R | 91–92 | 3700–2100br,3176, 1664,1320,1143 | 2.70–2.93(m, 2H), 2.82(s, 6H), 3.75(m, 1H), |
| 12 | (CH$_3$)$_2$CH– | 4-H$_3$CO-C$_6$H$_4$– | R | 178–179 | 3268,1632,1598, 1336,1162 | 0.71(d, J=8.8Hz,3H), 0.74(d, J=5.4Hz, 3H), 1.73(m, 1H), 1.73(m, 1H), 3.22(m, 1H), 3.82(s, 3H), 7.05(d, J=9.0Hz, 2H), 7.69(d, J=9.0Hz, 2H) |
| 13 | 4-O$_2$N-C$_6$H$_4$-CH$_2$– | 4-biphenylyl | RS | 184–185 | 3257,1662,1516, 1344,1322,1160 | 2.80(dd, J=10.0, 13.8Hz, 1H), 2.92(dd, J=5.0, 12.8Hz, 1H), 3.90(dd, J=5.4, 9.6Hz, 1H), |
| 14 | 4-F-C$_6$H$_4$-CH$_2$– | 4-biphenylyl | RS | 128–130 | 3258,1669,1509, 1322,1157 | 2.62(dd, J=9.9, 13.5Hz, 1H), 2.78(dd, J=5.8, 13.0Hz, 1H), 3.77(t, J=6.2Hz, 1H) |
| 15 | cyclohexyl-CH$_2$– | 4-biphenylyl | R | 165–166 | 3278,2920,1632, 1337,1161 | 0.50–1.62(m, 13H), 3.56(t, J=7.4Hz, 1H) |
| 16 | (1-methylindol-3-yl)-CH$_2$– | 4-biphenylyl | RS | 172–173 | 3272,1631,1332, 1161 | 2.71(dd, J=7.9, 14.2Hz, 1H), 2.94(dd, J=6.9, 14.2Hz, 1H), 3.57(s, 3H), 3.83(dd, J=7.0, 7.4Hz, 1H) |

TABLE 2-continued
(Ib)
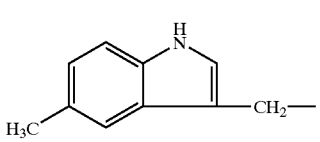
| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 17 | 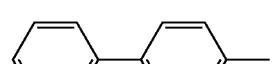 | 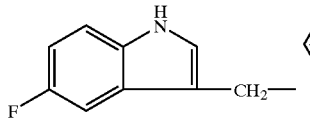 | RS | 144–146 | 3404,1670,1320, 1159 | 2.25(s, 3H), 2.67(dd, J=7.5, 14.2Hz, 1H), 2.95(dd, J= 7.7, 14.6Hz, 1H), 3.81(dd, J=6.2, 14.2Hz, 1H) |
TABLE 3
(Ib)
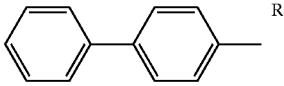
| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 18 | 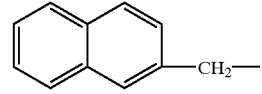 | 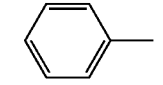 | RS | — | 3420,1870,1592, 1321,1159 | 2.72(dd, J=8.0, 14.0Hz, 1H), 2.90(dd, J=6.2, 14.2Hz, 1H), 3.82(m, 1H) |
| 19 | 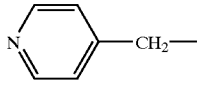 | 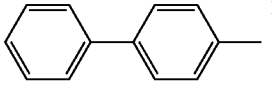 | RS | — | — | — |
| 20 | 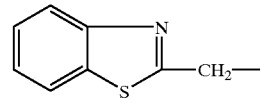 | 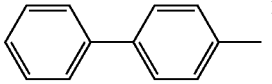 | RS | 154–158 | 3186,1593,1480,1379 | 2.68(dd, J=9.8, 13.7Hz, 1H), 2.79(dd, J=5.6, 12.8Hz, 1H), 3.85(t, J=7.0Hz, 1H), |
| 21 | 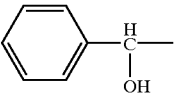 | 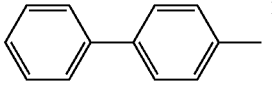 | RS | 111–115 | 3700–2400br,3252, 1668,1326,1160 | 3.22–3.38(m, 2H), 4.17– 4.24(m, 2H), 7.80(d, J=8.0Hz, 2H), 7.96(d, J=6.4Hz, 2H) |
| 22 | 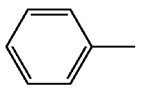 | 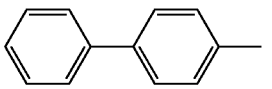 | RS | — | 3455,3362,1672, 1398,1162 | 3.86(d, J=3.6Hz, 1H), 4.91(d, J=3.6Hz, 1H) |
| 23 | 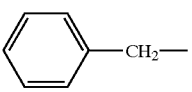 | 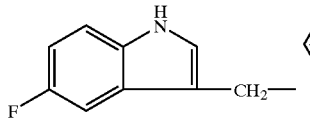 | R | 196–197 | 3404,3315,1669, 1594,1316,1162 | 4.88(d, J=9.4Hz, 1H), 8.74(d, J=9.4Hz, 1H), 8.98(s, 1H), 10.92(s, 1H) |
| 24 | 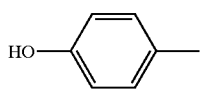 | 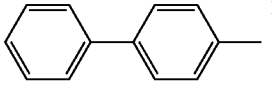 | R | 197–199 | 3700–2400(br),3473, 1675,1310,1152 | 2.69(dd, J=7.6, 13.5Hz, 1H), 2.93(dd, J=7.6, 13.5Hz, 1H), 3.77(t, J=7.6Hz, 1H), (CD₃OD) |

TABLE 3-continued (Ib)

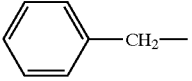

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 25 | 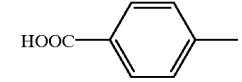 | 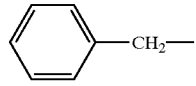 | R | 201–202 | 3700–2200(br),3278, 1706,1645,1322,1162 | 2.74(dd, J=8.3, 13.5Hz, 1H), 2.95(dd, J=6.5, 13.5Hz, 1H), 3.87(dd, J=6.5, 8.3Hz, 1H), (CD₃OD) |

TABLE 4

(Ib)

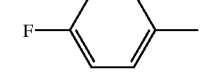

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 26 | 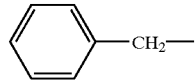 | 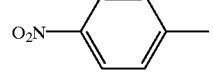 | R | 63–65 | 3700–2200(br),3362, 1670,1590,1336,1152 | 2.60(dd, J=9.0, 13.8Hz, 1H), 2.79(dd, J=9.3, 13.8Hz, 1H), 3.76(m, 1H) |
| 27 | 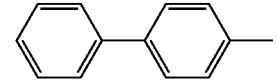 | 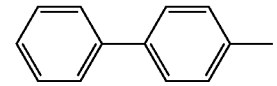 | R | 70–71 | 3700–2200br,3372, 1674,1531,1348,1310, 1161 | 2.66(dd, J=9.5, 13.6Hz, 1H), 2.79(dd, J=5.4, 13.6Hz, 1H), 3.84(m, 1H), 7.73(A₂B₂q, J=8.9Hz, 2H), 8.20(A₂B₂q, J=8.9Hz, 2H), 8.72(d, J=9.0Hz, 1H), 8.86(s, 1H), 10.7(s, 1H) |
| 28 | HOOC—CH₂— | 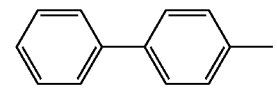 | R | — | — | — |
| 29 | HOOC—CH₂—CH₂— | 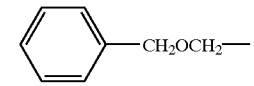 | R | — | — | — |
| 30 | HOCH₂— | 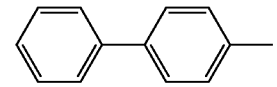 | R | 192–193 | 3700–2400(br),3392, 1667,1320,1161 | 3.29(dd, J=5.7, 10.7Hz, 1H), 3.43(dd, J=8.4, 10.7Hz, 1H), 3.62(m, 1H), 7.85(A₂B₂q, J=8.7Hz, 2H), 7.88(A₂B₂q, J=8.7Hz, 2H), 7.98(d, J=7.8Hz, 1H), 10.61(s, 1H) |
| 31 | 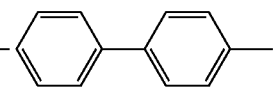 | 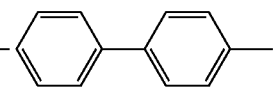 | R | 69–70 | 3700–2200(br),1671, 1329,1163 | 2.69(dd, J=7.6, 13.5Hz, 1H), 2.93(dd, J=7.6, 13.5Hz, 1H), 3.77(t, J=7.6Hz, 1H), (CD₃OD) |
| 32 | 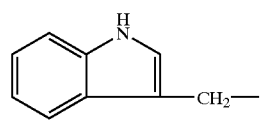 | | R | — | — | — |
| 33 | 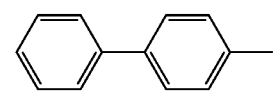 | | R | 160–162 | 3401,3260,1673, 1316,1165 | 2.66(dd, J=7.5, 13.4Hz, 1H), 2.96(dd, J=7.6, 14.2Hz, 1H), 3.81(m, 1H) |

TABLE 5

(Ib)

R[18]SO$_2$NH—*CH(R$^1$)—CONHOH

| Example No. | R$^1$ | R$^{18}$ | * | mp (decomp.) (° C.) | IR ($\nu$ cm$^{-1}$) (KBr) | $^1$H-NMR($\delta$ ppm) d$_6$-DMSO |
|---|---|---|---|---|---|---|
| 34 | 1H-indol-3-yl-CH$_2$— | 5-bromo-2-thienyl | R | — | — | — |
| 35 | 1H-benzimidazol-2-yl-CH$_2$— | 4-biphenylyl | RS | 141–145 | 3700–2400(br),1672, 1443,1327,1094 | 2.84–3.21(m, 2H), 4.29(m, 1H) |

TABLE 6

(Ia)

R[18]SO$_2$NH—*CH(R$^1$)—COOH

| Example No. | R$^1$ | R$^{18}$ | * | mp (decomp.) (° C.) | IR ($\nu$ cm$^{-1}$) (KBr) | $^1$H-NMR($\delta$ ppm) d$_6$-DMSO |
|---|---|---|---|---|---|---|
| 2 | thiazol-4-yl-CH$_2$— | 4-biphenylyl | RS | 159–161 | 3276,2503br, 1897br,1724, 1344,1170 (Nujol) | 2.95(dd, J=9.0, 14.0Hz, 1H), 3.12(dd, J=5.4, 14.0Hz, 1H), 4.13(m, 1H), 7.29(d, J=2.0Hz, 1H), 8.34(d, J=8.6Hz, 1H), 8.88 (d, J=2.0Hz, 1H), 12.79(br, 1H) |
| 3 | 1H-indol-3-yl-CH$_2$— | 4-biphenylyl | R | 227–229 | 3386,3305, 1747,1363, 1323,1161, 1135(Nujol) | 2.88(dd, J=8.0, 14.0Hz, 1H), 3.09(dd, J=6.0, 14.0Hz, 1H), 3.91(m, 1H), 8.23 (m, 1H), 10.79(s, 1H), 12.70(br, 1H) |
| 4 | 5-methoxy-1H-indol-3-yl-CH$_2$— | 4-biphenylyl | RS | 181–189 | 2400– 3700(br), 1734,1484, 1327,1160 | 2.75–3.06(m, 2H), 3.69(s, 3H), 3.90(m, 1H) |
| 5 | naphthalen-1-yl-CH$_2$— | 4-biphenylyl | RS | 198–200 | 3446,3065, 1594,1397, 1303,1154, 1094 | 3.17(dd, J=7.4, 13.8Hz, 1H), 3.57(dd, J=5.5, 13.9Hz, 1H), 3.80(t, J=5.6Hz, 1H), 8.11(d, J=7.4Hz, 1H) |
| 6 | 4-biphenylyl-CH$_2$— | 4-biphenylyl | R | 213–215 | 3184,1723, 1337,1317, 1156 | 2.77(dd, J=9.7, 13.7Hz, 1H), 3.03(dd, J=4.9, 13.3Hz, 1H), 3.93(m, 1H), 8.38 (d, J=8.8Hz, 1H) |
| 7 | CF$_3$CH$_2$— | 4-biphenylyl | R | 176–177 | 3276,1706, 1344,1260, 1165 | 2.40–2.90(m, 2H), 4.05(m, 1H), 8.51(d, J=9.0Hz, 1H), 13.2(br, 1H) |

TABLE 6-continued (Ia)

$$R^{18}SO_2NH-\overset{R^1}{\underset{*}{C}H}-COOH$$

| Example No. | R$^1$ | R$^{18}$ | * | mp (decomp.) (° C.) | IR ($\nu$ cm$^{-1}$) (KBr) | $^1$H-NMR($\delta$ ppm) d$_6$-DMSO |
|---|---|---|---|---|---|---|
| 8 | phenyl-CH$_2$CH$_2$— | 4-biphenyl- | RS | 153–156 | 3289,1739, 1326,1159, 1089 | 1.83(m, 2H), 2.52(m, 2H), 3.70(m, 1H), 8.32(d, J=9.0Hz, 1H) |
| 11 | phenyl-CH$_2$— | 5-(dimethylamino)naphthalen-1-yl- | R | 103–105 | 2200–3700br, 3439,3288, 1725,1329, 1143 | 2.86(m, 1H), 2.87(s, 6H), 2.98(dd, J=5.1, 13.8Hz, 1H), 4.15(m, 1H), 5.54(m, 1H) |

TABLE 7

(Ia)

$$R^{18}SO_2NH-\overset{R^1}{\underset{*}{C}H}-COOH$$

| Example No. | R$^1$ | R$^{18}$ | * | mp (decomp.) (° C.) | IR ($\nu$ cm$^{-1}$) (KBr) | $^1$H-NMR($\delta$ ppm) d$_6$-DMSO |
|---|---|---|---|---|---|---|
| 13 | 4-O$_2$N-C$_6$H$_4$-CH$_2$— | 4-biphenyl- | RS | 212–213 | 3113,1724,1520, 1345,1158 | 2.86(dd, J=10.2, 13.2Hz, 1H), 3.14(dd, J=4.5, 13.7Hz, 1H), 4.02(m, 1H), 8.42(d, J=8.4Hz, 1H) |
| 14 | 4-F-C$_6$H$_4$-CH$_2$— | 4-biphenyl- | RS | 164–165 | 3426,3114,1715, 1509,1224,1159 | 2.71(dd, J=9.9, 13.7Hz, 1H), 2.96(dd, J=5.3, 13.5Hz, 1H), 3.89(m, 1H), 8.34(d, J=9.0Hz, 1H) |
| 15 | cyclohexyl-CH$_2$— | 4-biphenyl- | R | 85–87 | 2919,1688,1448, 1335,1326,1169 | 0.52–1.72(m, 13H), 3.68(m, 1H), 8.20(br.s, 1H) |
| 16 | (1-methylindol-3-yl)-CH$_2$— | 4-biphenyl- | RS | 179–183 | 3432,3294,1713, 1482,1341,1159 | 2.80–3.12(m, 2H), 3.61(s, 3H), 3.94(m, 1H), 8.30(d, J=8.6Hz, 1H) |
| 17 | (5-methyl-1H-indol-3-yl)-CH$_2$— | 4-biphenyl- | RS | 115–120 | 3419,3397,3291, 1736,1482,1336, 1321,1165 | 2.28(s, 3H), 2.78–3.10(m, 2H), 3.91(m, 1H), 8.29(d, J=8.3Hz, 1H) |
| 18 | (5-fluoro-1H-indol-3-yl)-CH$_2$— | 4-biphenyl- | RS | 208–211 | 3407,3285,1751, 1735,1703,1486, 1321,1162 | 2.80–3.10(m, 2H), 3.92(m, 1H), 8.29(d, J=8.2Hz, 1H) |

TABLE 7-continued (Ia)

$$R^{18}SO_2NH-\overset{R^1}{\underset{*}{C}H}-COOH$$

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 20 | 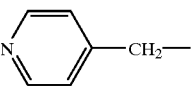 | 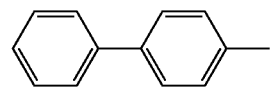 | RS | 197–205 | 2600–3700br, 1635,1594,1335, 1163,1095 | 2.80–3.04(m, 2H), 3.98(m, 1H) |
| 21 | 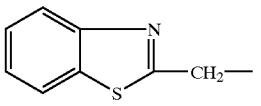 | 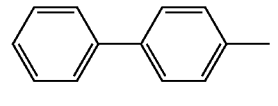 | RS | 196–199 | 2200–3100br, 1713br,1345,1125 | 3.24–3.56(m, 2H), 4.34(m, 1H) |

TABLE 8

(Ia)

$$R^{18}SO_2NH-\overset{R^1}{\underset{*}{C}H}-COOH$$

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 22 | 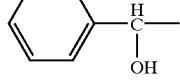 | 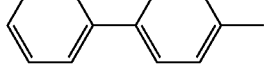 | RS | 141–143 | 3335,3246,1732, 1315,1152 | 4.10(d, J=3.2Hz, 1H), 5.13(d, J=3.2Hz, 1H) |
| 23 | 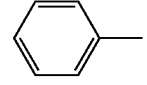 | 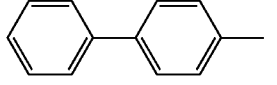 | R | 211–214 | 3316,1734,1325, 1159(Nujol) | 4.94(d, J=9.4Hz, 1H), 8.80(d, J=9.4Hz, 1H), 13.0(br.s, 1H) |
| 28 | HOOC—CH₂— | 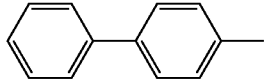 | R | 171–173 | 3353,1752,1326, 1155,1096 | 2.45(dd, J=6.2, 16.4Hz, 1H) 2.63(dd, J=6.6, 16.4Hz, 1H), |
| 29 | HOOC—CH₂—CH— | 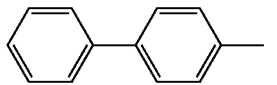 | R | 185–187 | 3270,1709,1336, 1159,1093 | 1.68(dd, J=7.9, 14.1Hz, 1H), 1.87(dd, J=6.0, 13.4Hz, 1H), 2.22(t, J=7.2Hz, 2H), 3.80(m, 1H), |
| 30 | HOCH₂— | 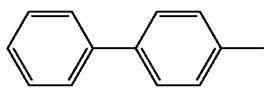 | R | 277–279 | 2200–3700br, 3430,3292,1728, 1324,1162 | 3.51(dd, J=6.0, 12.9Hz, 1H), 3.55(dd, J=5.4, 12.9Hz, 1H), 3.80(m, 1H), 8.06(d, J=8.7Hz, 1H) |
| 31 | 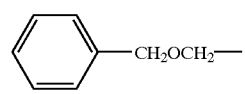 | 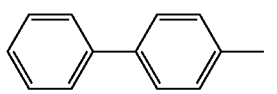 | R | 89–91 | 2200–3700br, 3432,3289,1733, 1330,1165 | 3.54(dd, J=4.8, 9.9Hz, 1H), 3.60(dd, J=5.7, 9.9Hz, 1H), 4.04(m, 1H), 4.39(s, 2H), 8.34(d, J=8.1Hz, 1H) |
| 32 |  | 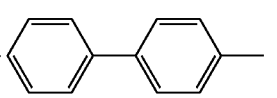 | R | >270 | 3319,3052,1701, 1317,1284,1162 | 2.81(dd, J=9.7, 13.7Hz, 1H), 3.05(dd, J=4.8, 13.4Hz, 1H), 3.96(m, 1H), 8.40(d, J=9.0Hz, 1H), 12.88(br.s, 1H) |

TABLE 9

(Ia)

$$R^{18}SO_2NH-\overset{R^1}{\underset{*}{C}H}-COOH$$

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 34 | indol-3-ylmethyl | 5-bromothien-2-yl | R | 243–246 | 3420,1588,1402, 1324,1151 | 3.06(dd, J=5.4, 14.4Hz, 1H), 3.14(dd, J=5.1, 14.4Hz, 1H), 3.65(t, J=5.4Hz, 1H), 6.92(m, 1H), 10.72(s, 1H) |
| 35 | benzimidazol-2-ylmethyl | 4-biphenylyl | RS | 151–156 | 2200–3700br, 1734,1334,1161 | 3.17–3.50(m, 2H), 4.51(m, 1H) |

TABLE 10

(Ia)

$$R^{18}SO_2NH-\overset{R^1}{\underset{*}{C}H}-COOH$$

| Example No. | R¹ | R¹⁸ | * | mp (decomp.) (° C.) | IR (ν cm⁻¹) (KBr) | Elemental analysis |
|---|---|---|---|---|---|---|
| 36 | N-(SO₂CH₃)-indol-3-ylmethyl | 4-biphenylyl | RS | >145 | 1726,1354 1326,1161 | — |
| 37 | N-(COOC₂H₅)-indol-3-ylmethyl | 4-biphenylyl | RS | — | 1732,1594 1404,1155 | — |
| 38 | indol-3-ylmethyl | 4'-methoxy-4-biphenylyl | R | 188–190 | 1607,1594 1294,1153 | C₂₄H₂₂N₂O₅S·0.5H₂O Calc. C:62.73 H:5.04 N:6.10 S:6.98 Foun. C:62.75 H:5.08 N:6.31 S:7.05 |
| 39 | indol-3-ylmethyl | 3'-methoxy-4-biphenylyl | R | 90–93 | 1724,1594 1326,1159 | C₂₄H₂₂N₂O₅S·0.8H₂O Calc. C:62.00 H:5.12 N:6.03 S:6.90 Foun. C:62.03 H:5.06 N:6.08 S:6.82 |
| 40 | indol-3-ylmethyl | 4'-methyl-4-biphenylyl | R | 149–152 | 1685,1349 1166 | — |

TABLE 10-continued $$R^{18}SO_2NH-\overset{R^1}{\underset{*}{C}}-COOH \quad (Ia)$$

| Example No. | R¹ | R¹⁸ | * | mp (decomp.) (° C.) | IR (ν cm⁻¹) (KBr) | Elemental analysis |
|---|---|---|---|---|---|---|
| 41 | indol-3-ylmethyl (1H-indole-CH₂—) | 4'-fluoro-biphenyl-4-yl | R | 104–107 | 1725,1599 1372,1173 | — |
| 42 | indol-3-ylmethyl (1H-indole-CH₂—) | 4'-(methylthio)-biphenyl-4-yl (H₃CS—) | R | 167–169 | 1745,1653 1391,1147 | — |
| 43 | $(CH_3)_2CH-$ | biphenyl-4-yl | R | 155–157 | 1714,1594 1334,1166 | $C_{17}H_{19}NO_4S \cdot 0.1CF_3COOH$ Calc. C:59.99 H:5.58 N:4.06 S:9.30 Foun. C:60.37 H:5.74 N:4.13 S:9.76 |

TABLE 11

$$R^{18}SO_2NH-\overset{R^1}{\underset{*}{C}}-COOH \quad (Ia)$$

| Example No. | R¹ | R¹⁸ | * | mp (decomp.) (° C.) | IR (ν cm⁻¹) (KBr) | Elemental analysis |
|---|---|---|---|---|---|---|
| 44 | $(CH_3)_2CH-$ | 4'-tert-butyl-biphenyl-4-yl (ᵗBu—) | R | 196–197 | 1724,1340 1328,1167 | $C_{21}H_{27}NO_4S \cdot 0.3H_2O$ Calc. C:63.87 H:7.04 N:3.55 S:8.12 Foun. C:63.84 H:6.86 N:3.42 S:8.01 |
| 45 | $(CH_3)_2CH-$ | 4''-terphenyl-4-yl | R | 241–243 | 1734,1719 1324,1160 | $C_{23}H_{23}NO_4S \cdot 0.3H_2O$ Calc. C:66.58 H:5.73 N:3.38 S:7.73 Foun. C:66.45 H:5.52 N:3.24 S:7.56 |
| 46 | $(CH_3)_2CH-$ | 4'-(trifluoromethyl)-biphenyl-4-yl (F₃C—) | R | 157–159 | 1670, 1375 1148 | — |
| 47 | $(CH_3)_2CH-$ | 4'-methoxy-biphenyl-4-yl (H₃CO—) | R | 175–176 | 1717,1694 1349,1165 | — |
| 48 | $(CH_3)_2CH-$ | 4'-fluoro-biphenyl-4-yl (F—) | R | 145–147 | 1634,1334 1158 | $C_{17}H_{18}FNO_4S$ Calc. C:58.11 H:5.16 F:5.41 N:3.99 S:9.12 Foun. C:58.11 H:5.17 F:5.86 N:3.92 S:9.69 |
| 49 | $(CH_3)_2CH-$ | 4'-methyl-biphenyl-4-yl (H₃C—) | R | 183–186 | 1681,1319 1162 | — |

TABLE 11-continued
(Ia)
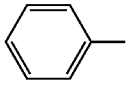
| Example No. | R¹ | R¹⁸ | * | mp (decomp.) (° C.) | IR (ν cm⁻¹) (KBr) | Elemental analysis |
|---|---|---|---|---|---|---|
| 50 | 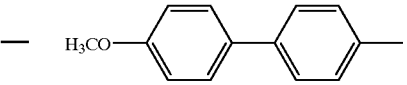 | 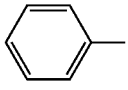 | R | 183–184 | 1725,1340 1159 | — |
| 51 | 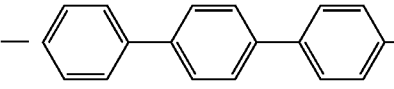 | 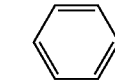 | R | 224–226 | 1750,1324 1159 | $C_{27}H_{23}NO_4S \cdot 0.7H_2O$<br>Calc. C:68.98 H:5.23<br>N:2.98 S:6.82<br>Foun. C:69.08 H:5.09<br>N:2.91 S:6.73 |
TABLE 12
(Ia)
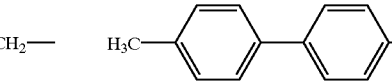
| Example No. | R¹ | R¹⁸ | * | mp (decomp.) (° C.) | IR (ν cm⁻¹) (KBr) | Elemental analysis |
|---|---|---|---|---|---|---|
| 52 | 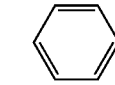 | 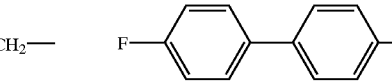 | R | 157–160 | 1685,1349 1166 | — |
| 53 | 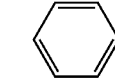 | 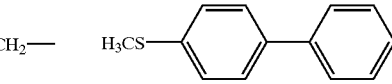 | R | 111–112 | 1691,1567 1390,1159 | — |
| 54 |  | 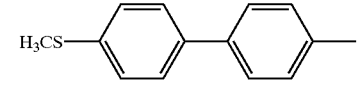 | R | 194–195 | 1749,1592 1323,1164 | — |
| 55 | $(CH_3)_2CH—$ | 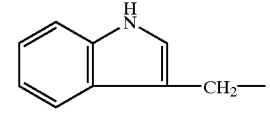 | R | 197–199 | 1746,1337 1164 | $C_{18}H_{21}NO_4S_2 \cdot 0.2H_2O$<br>Calc. C:56.43 H:5.63<br>N:3.66 S:16.74<br>Foun. C:56.74 H:5.67<br>N:3.86 S:16.35 |
| 56 | 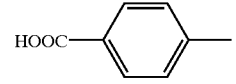 | 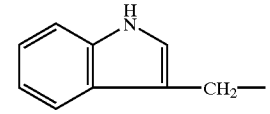 | R | 108–110 | 1649,1337 1165 | — |
| 57 | 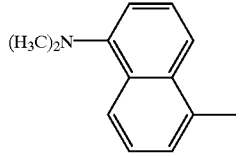 | | R | 187–190 | 1588,1308 1141 | — |

TABLE 12-continued (Ia)

R¹⁸SO₂NH—*CH(R¹)—COOH

| Example No. | R¹ | R¹⁸ | * | mp (decomp.) (° C.) | IR (ν cm⁻¹) (KBr) | Elemental analysis |
|---|---|---|---|---|---|---|
| 58 | 1-(COOC₂H₅)-indol-3-yl-CH₂— | 5-(thiophen-2-yl)-phenyl | R | 239–243 | 1744,1592 1323,1160 | $C_{21}H_{18}N_2O_4S_2 \cdot 0.3H_2O$ Calc. C:58.40 H:4.34 N:6.45 S:14.85 Foun. C:58.40 H:4.44 N:6.58 S:14.57 |
| 59 | 1H-indol-3-yl-CH₂— | 2-chloro-5-nitro-phenyl | R | 222–224 | 1751,1734 1537,1347 1172 | $C_{17}H_{14}ClN_3O_6S \cdot 0.3H_2O$ Calc. C:47.48 H:3.44 Cl:8.39 N:9.65 S:7.52 Foun. C:47.57 H:3.43 Cl:8.26 N:9.79 S:7.47 |

TABLE 13

(Ib)

R¹⁸SO₂NH—*CH(R¹)—CONHOH

| Example No. | R¹ | R¹⁸ | * | mp (decomp.) (° C.) | IR (ν cm⁻¹) (KBr) | ¹H-NMR(δ ppm) de-DMSO |
|---|---|---|---|---|---|---|
| 60 | phenyl-CH₂— | 4-phenoxy-phenyl | R | foam | 3700–2400br, 3277,1669 1325,1152 | 2.60(dd, J=8.7, 13.7Hz, 1H), 2.79(dd, J=6.0, 13.7Hz, 1H), 13.75(ddd, J=6.0, 8.7, 9.0, 1H), 6.94(d, J=8.9Hz, 2H) |
| 61 | 1H-indol-3-yl-CH₂— | 4-phenoxy-phenyl | R | 115–118 | 3302,1667 1324,1153 (Nujol) | 2.71 (dd, J=7.0, 14.4Hz, 1H), 2.96(dd, J=7.0, 14.2Hz, 1H), 3.78(t, J=7.6Hz, 1H) |
| 62 | 1H-indol-3-yl-CH₂— | 4-phenoxy-phenyl | S | — | 3406,1670 1582,1325 1153 | 2.71(dd, J=7.9, 14.4Hz, 1H), 2.96(dd, 7.6, 14.4Hz, 1H), 3.78(dd, J=7.2, 7.3Hz, 1H) |
| 63 | (CH₃)₂CH— | 4-phenoxy-phenyl | R | 149–151 | 3268,1634 1584,1336 1157 | 0.76(d, J=6.6Hz, 6H), 1.77(m, 1H), 3.26(m, 1H) |
| 64 | 1-methyl-indol-3-yl-CH₂— | 4-phenoxy-phenyl | RS | — | 3314,1669 1582,1420 1328,1154 | 2.71(dd, J=7.9, 14.2Hz, 1H), 2.93(dd, J=6.5, 14.3Hz, 1H), 3.65(s, 3H), 3.78(dd, J=7.1, 7.2Hz, 1H) |
| 65 | 5-methyl-1H-indol-3-yl-CH₂— | 4-phenoxy-phenyl | RS | — | 3405, 1671 1582,1487 1324,1154 | 2.34(s, 3H), 2.65(dd, J=7.8, 14.1Hz, 1H), 2.93(dd, J=7.6, 14.4Hz, 1H), 3.75(dd, J=6.8, 7.7Hz, 1H) |

TABLE 13-continued (Ib)

$$R^{18}SO_2NH-\overset{R^1}{\underset{*}{C}}H-CONHOH$$

| Example No. | R[1] | R[18] | * | mp (decomp.) (° C.) | IR (ν cm$^{-1}$) (KBr) | $^1$H-NMR(δ ppm) de-DMSO |
|---|---|---|---|---|---|---|
| 66 | 5-fluoro-1H-indol-3-yl-CH$_2$— | 4-phenoxyphenyl | RS | — | 3317,1670, 1582,1488, 1323,1153 | 2.71 (dd, J=8.9, 14.4Hz, 1H), 2.89(dd, J=6.6, 14.4Hz, 1H), 3.75(dd, J=6.5, 6.8Hz, 1H) |
| 67 | 1-acetyl-1H-indol-3-yl-CH$_2$— | 4-phenoxyphenyl | RS | — | 3421,1702, 1676,1582, 1354,1328, 1153 | 2.54(s, 3H), 2.69–2.89(m, 2H), 3.87(m, 1H) |

TABLE 14

(Ia)

$$R^{18}SO_2NH-\overset{R^1}{\underset{*}{C}}H-COOH$$

| Example No. | R[1] | R[18] | * | mp (decomp.) (° C.) | IR (ν cm$^{-1}$) (KBr) | $^1$H-NMR(δ ppm) d$_6$-DMSO |
|---|---|---|---|---|---|---|
| 60 | phenyl-CH$_2$— | 4-phenoxyphenyl | R | 108–109 | 2400–3600br, 3345,3213, 1735,1700, 1346,1163 | 2.72 (dd, J=8.7, 13.6Hz, 1H), 2.94(dd, J=5.6, 13.6Hz, 1H), 3.84(ddd, J=5.6, 8.7, 8.7Hz, 1H), 8.23(d, J=8.7Hz, 1H) |
| 61 | 1H-indol-3-yl-CH$_2$— | 4-phenoxyphenyl | R | 82–87 | 3410,3276, 1724,1582, 1488,1331, 1152(Nujol) | 2.88(dd, J=7.4, 15.2Hz, 1H), 3.07(dd, J=6.2, 14.4Hz, 1H), 3.83(m, 1H), 8.08(m, 1H), 10.80(s, 1H), 12.70(br, 1H) |
| 62 | 1H-indol-3-yl-CH$_2$— | 4-phenoxyphenyl | S | foam | 3412,1724, 1582,1488, 1332,1152 | 2.81–3.12(m, 2H), 3.88(m, 1H), 8.19(d, J=8.4Hz, 1H) |
| 63 | (CH$_3$)$_2$CH— | 4-phenoxyphenyl | R | 137–138 | 3154,1720 1688,1583, 1488,1251 | 0.89(d, J=7.0Hz, 3H), 0.98(d, J=6.8Hz, 3H), 2.12(m, 2H), 3.80(dd, J=4.7, 9.7Hz, 1H), 5.17(d, J=9.6Hz, 1H) |
| 64 | 1-methyl-1H-indol-3-yl-CH$_2$— | 4-phenoxyphenyl | RS | — | 3273,1724, 1582,1487, 1331,1198, 1153 | 2.78–3.10(m, 2H), 3.67(s, 3H), 3.86(m, 1H) |

TABLE 14-continued
$$\underset{R^{18}SO_2NH}{\overset{R^1}{\underset{*}{\bigvee}}}COOH \quad (Ia)$$
| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 65 | 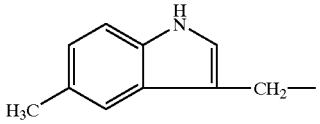 | 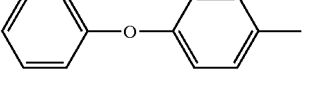 | RS | — | 3409,3281, 1725,1582, 1331,1197, 1153 | 2.34(s, 3H), 2.75–3.08(m, 2H), 3.86(m, 1H), 8.19(d, J= 8.4Hz, 1H) |
| 66 | 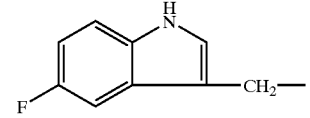 | 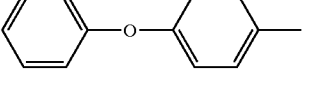 | RS | — | 3415,1725, 1582,1488, 1329,1196, 1174,1152 | 2.78–3.08(m, 2H), 3.85(m, 1H), 8.18 (d, J=8.6Hz, 1H) |
| 67 | 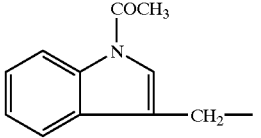 | 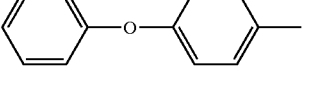 | RS | 236–237 | 3296,1742, 1647,1604, 1581,1342, 1334,1152 | 2.55(s, 3H),2.79–3.11(m, 2H), 3.98(m, 1H) |
TABLE 15
$$\underset{R^{18}SO_2NH}{\overset{R^1}{\underset{*}{\bigvee}}}COOH \quad (Ia)$$
| Example No. | R¹ | R¹⁸ | * | mp (decomp.) (° C.) | IR (ν cm⁻¹) (KBr) | Elemental analysis |
|---|---|---|---|---|---|---|
| 68 | 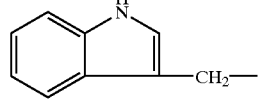 | 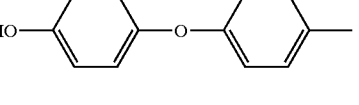 | R | >240 | 1608,1590 1507,1232 1157 | — |
| 69 | 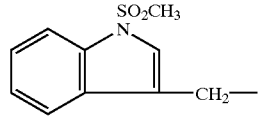 | 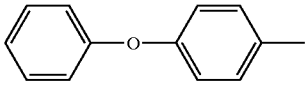 | RS | — | 1735,1583 1362,1171 | C₂₄H₂₂N₂O₇S₂ Calc. C:56.02 H:4.31 N:5.44 S:12.46 Foun. C:55.75 H:4.40 N:5.41 S:12.21 |
| 70 | 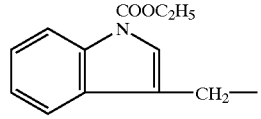 | 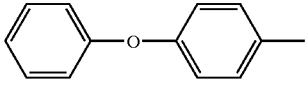 | RS | — | 1733,1583 1150 | — |

TABLE 16

$$\text{R}^{18}\text{SO}_2\text{NH}-\overset{\text{R}^1}{\underset{*}{\text{C}}}-\text{CONHOH} \qquad \text{(Ib)}$$

| Example No. | R$^1$ | R$^{18}$ | * | mp (decomp.) (° C.) | IR (ν cm$^{-1}$) (KBr) |
|---|---|---|---|---|---|
| 71 | benzyl (PhCH$_2$–) | CH$_3$(CH$_2$)$_4$–C$_6$H$_4$– (4-pentylphenyl) | R | 129–131 | 3700–2400 br, 3247, 1636, 1337, 1160 |
| 72 | benzyl (PhCH$_2$–) | CH$_3$(CH$_2$)$_7$– | R | oil | 3700–2400 br, 1663, 1320, 1145 (film) |
| 73 | benzyl (PhCH$_2$–) | CH$_3$(CH$_2$)$_3$– | R | oil | 3600–2400 br, 3262, 1673, 1321, 1142 (CHCl$_3$) |
| 74 | 1H-indol-3-ylmethyl | 5-chloro-2,3-dimethylbenzo[b]thiophen-? | R | — | — |
| 75 | benzyl (PhCH$_2$–) | 4-benzylphenyl (PhCH$_2$–C$_6$H$_4$–) | R | 85–86 | 3700–2200 (br), 3262, 1639, 1332, 1156 |
| 76 | 1H-indol-3-ylmethyl | 4-morpholinyl | R | — | — |

| Example No. | $^1$H—NMR (δ ppm) d$_6$-DMSO |
|---|---|
| 71 | 0.90(t, J=6.8Hz, 3H), 1.22–1.40(m, 4H), 1.52–1.67(m, 2H), 2.62(t, J=7.7Hz, 2H), 2.86(dd, J=8.4, 13.7Hz, 1H), 3.02(dd, J=5.7, 13.7Hz, 1H) (CDCl$_3$) |
| 72 | 0.87(t, J=6.3Hz, 3H), 2.50(t, J=7.4Hz, 2H), 2.76(dd, J=9.6, 14.0Hz, 1H), 2.87(dd, J=5.8, 14.0Hz, 1H), 3.84(dd, J=5.8, 9.6Hz, 1H), |
| 73 | 0.79(t, J=7.0Hz, 3H), 2.32–2.56(m, 2H), 2.92(m, 1H), 3.26(m, 1H), |
| 74 | — |
| 75 | 2.80(m, 1H), 2.96(m, 1H), 3.94(s, 2H), 3.86(m, 1H), 6.80–7.52(m, 10H), 7.08(A$_2$B$_2$q J=7.5Hz, 2H), 7.42(A$_2$B$_2$q, J=7.5Hz, 2H)(CDCl$_3$) |
| 76 | — |

TABLE 17

$$R^{18}SO_2NH-\overset{R^1}{\underset{*}{C}H}-CONHOH \quad (Ib)$$

| Example No. | R¹ | R¹⁸ | * | mp (decomp.) (°C.) | IR (ν cm⁻¹) (KBr) | ¹H—NMR (δ ppm) d₆-DMSO |
|---|---|---|---|---|---|---|
| 77 | benzyl (PhCH₂—) | trans-styryl (PhCH=CH—) | R | 138–139 | 3700–2400 (br), 3312, 1629, 1329, 1144 | 2.79(dd, J=8.5, 13.4Hz, 1H), 2.89(dd, J=6.0, 13.4Hz, 1H), 3.81(dd, J=6.0, 8.5Hz, 1H), 6.55(d, J=15.5Hz, 1H) |
| 78 | benzyl (PhCH₂—) | benzyl (PhCH₂—) | R | 69–70 | 3700–2200 (br), 1670, 1318, 1152 | 2.78(dd, J=8.6, 13.4Hz, 1H), 2.91(dd, J=6.0, 13.4Hz, 1H), 3.92(ABq, J=13.5Hz, 1H), 3.90(m, 1H), 9.01(s, 1H), 10.78(s, 1H) |
| 79 | (1H-indol-3-yl)methyl | cyclohexyl-NH— | R | — | — | — |

TABLE 18

$$R^{18}SO_2NH-\overset{R^1}{\underset{*}{C}H}-COOH \quad (Ia)$$

| Example No. | R¹ | R¹⁸ | * | mp (decomp.) (°C.) | IR (ν cm⁻¹) (KBr) |
|---|---|---|---|---|---|
| 71 | benzyl (PhCH₂—) | CH₃(CH₂)₄—C₆H₄— (4-pentylphenyl) | R | 121–122 | 2300–3700 br, 3426, 3318, 1713, 1330, 1159 |
| 72 | benzyl (PhCH₂—) | CH₃(CH₂)₇— | R | oil | 2400–3600 br, 3340, 1736, 1334, 1142 (CHCl₃) |
| 73 | benzyl (PhCH₂—) | CH₃(CH₂)₃— | R | 89–90 | 2300–3700 br, 3240, 1725, 1341, 1144 |
| 74 | (1H-indol-3-yl)methyl | 5-chloro-2,3-dimethylbenzo[b]thiophen-? | R | >250 | 3421, 1580, 1333, 1421, 1153 |
| 76 | (1H-indol-3-yl)methyl | morpholin-4-yl | R | foam | 3413, 1594, 1456, 1416, 1157 |
| 77 | benzyl (PhCH₂—) | trans-propenylphenyl (PhCH=CH—CH-) | R | — | 2400–3700 br, 3252, 1765, 1725, 1301, 1140 |

TABLE 18-continued (Ia)

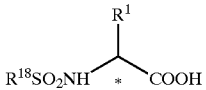

| No. | R¹ | R¹⁸ | * | mp | IR |
|---|---|---|---|---|---|
| 78 | 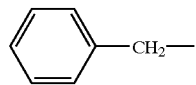 | 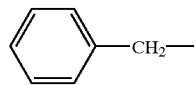 | R | — | 2200–3700 br, 3268, 1726, 1321, 1152 (film) |
| 79 | 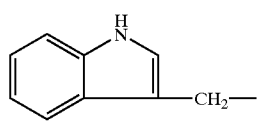 | 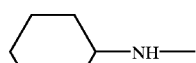 | R | — | 3413, 2931, 1720, 1585, 1455, 1421, 1313, 1144 |

| Example No. | ¹H—NMR (δ ppm) d₆-DMSO |
|---|---|
| 71 | 0.89(t, J=6.7Hz, 3H), 2.62(t, J=7.6Hz, 2H), 2.96 (dd, J=7.0, 13.9Hz, 1H), 3.10(dd, J=5.4, 13.9Hz, 1H), 4.19(dt, J=6.9, 8.2Hz, 1H), 5.30(d, J=8.2Hz, 1H), |
| 72 | 0.88(t, J=6.9Hz, 3H), 2.55–2.73(m, 2H), 2.97(dd, J=8.4, 13.8Hz, 1H), 3.24(dd, J=4.8, 13.8Hz, 1H), 4.35(m, 1H), 4.98(m, 1H) (CDCl₃) |
| 73 | 0.84(t, J=7.1Hz, 3H), 2.57–2.70(m, 2H), 2.97(dd, J=8.4, 13.9Hz, 1H), 3.25(dd, J=4.8, 13.9Hz, 1H), 4.35(m, 1H), 4.96(d, J=9.6Hz, 1H) (CDCl₃) |
| 74 | 2.41(s, 3H), 3.01(dd, J=6.0, 14.4Hz, 1H), 3.12(dd, J=4.5, 14.4Hz, 1H), 3.67(t, J=5.4Hz, 1H), 6.79(m, 1H), 6.89(m, 1H), 10.59(s, 1H) |
| 76 | 3.03(dd, J=6.5, 15.1Hz, 1H), 3.15(dd, J=4.7, 14.1Hz, 1H), 3.64(t, J=5.1Hz, 1H), 10.68(s, 1H) |
| 77 | 2.81(dd, J=9.2, 13.7Hz, 1H), 3.03(dd, J=5.4, 13.7Hz, 1H), 3.94(dt, J=5.4, 9.2Hz, 1H), 6.66(d, J=15.2Hz, 1H), 7.16(d, J=15.2Hz, 1H), 8.01(d, J=9.2Hz, 1H) |
| 78 | 2.81(dd, J=9.2, 13.7Hz, 1H), 3.00(dd, J=5.6, 13.7Hz, 1H), 4.01(ABq, J=13.7Hz, 2H), 4.01(m, 1H), 7.65(d, J=8.3Hz, 1H) |
| 79 | 0.90–1.68(m, 9H), 1.78(m, 1H), 2.74(m, 1H), 3.00–3.20(m, 2H), 3.77(m, 1H), 6.45(br.s, 1H), 6.77(br.s, 1H) |

TABLE 19

(Ia)

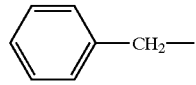

| Example No. | R¹ | R¹⁸ | * | mp (decomp.) (°C.) | IR (ν cm⁻¹) (KBr) |
|---|---|---|---|---|---|
| 80 | 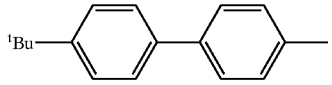 | 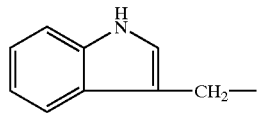 | R | 153–155 | 1704, 1596, 1349, 1164 |
| 81 | 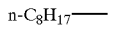 | n-C₈H₁₇— | R | >130 | 1576, 1356, 1139 |
| 82 | 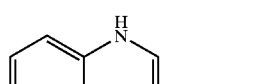 | 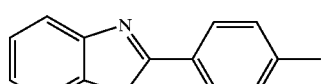 | R | 128–130 | 1732, 1342, 1167 |

TABLE 19-continued (Ia)

$$R^{18}SO_2NH-\underset{*}{\overset{R^1}{C}}H-COOH$$

| No. | R¹ | R¹⁸ | * | mp (decomp.) (° C.) | IR (ν cm⁻¹) (KBr) |
|---|---|---|---|---|---|
| 83 | (indol-3-yl)-CH₂— | 2-(4-methylphenyl)benzothiazol-6-yl | R | 210–214 | 1745, 1590, 1316, 1157 |
| 84 | (indol-3-yl)-CH₂— | 2-methyldibenzofuran-8-yl | R | 198–200 | 1594, 1456, 1200, 1188 |

| Example No. | ¹H—NMR (δ ppm) d₆-DMSO |
|---|---|
| 80 | — |
| 81 | — |
| 82 | $C_{24}H_{19}N_3O_5S \cdot 1.3H_2O$<br>Calc. C: 59.45  H: 4.49  N: 8.67  S: 6.61<br>Foun. C: 59.43  H: 4.45  N: 8.59  S: 6.58 |
| 83 | — |
| 84 | — |

TABLE 20

(Ib)

$$R^{18}SO_2NH-\underset{*}{\overset{R^1}{C}}H-CONHOH$$

| Example No. | R¹ | R¹⁸ | * | mp (decomp.) (° C.) | IR (ν cm⁻¹) (KBr) |
|---|---|---|---|---|---|
| 85 | PhCH₂— | 4-(phenylazo)-4'-methylphenyl | R | 157–160 | 3700–2400 br, 3273, 1633, 1338, 1166 |
| 86 | PhCH₂— | 4-((4-dimethylaminophenyl)azo)-4'-methylphenyl | R | 138–142 | 3700–2400 br, 2921, 1672, 1314, 1165, |
| 87 | PhCH₂— | 4-(3-(4-methylphenyl)ureido)phenyl | R | 206–207 | 3700–2400 (br), 3357, 1686, 1641, 1314, 1155 |

| Example No. | ¹H—NMR (δ ppm) d₆-DMSO |
|---|---|
| 85 | 2.65(dd, J=8.9, 13.6Hz, 1H), 2.82(dd, J=6.6, 13.6Hz, 1H), 3.86(m, 1H), 7.75(d, J=7.8Hz, 2H), 7.87(d, J=8.7Hz, 2H) |
| 86 | 2.62(dd, J=8.6, 13.5Hz, 1H), 2.81(dd, J=6.5, 13.6Hz, 1H), 3.09(s, 6H), 3.83(m, 1H), 6.86(d, J=9.0Hz, 2H), 7.83(d, J=8.8Hz, 2H) |
| 87 | 2.57(dd, J=8.3, 13.6Hz, 1H), 2.79(dd, J=6.0, 13.6Hz, 1H), 3.76(m, 1H), 8.02(d, J=8.7Hz, 1H), 8.80(s, 1H), 8.85(d, J=1.7Hz, 1H), 9.06(s, 1H), 10.59(d, J=1.7Hz, 1H) |

TABLE 21

(Ia)

R¹⁸SO₂NH—*CH(R¹)—COOH

| Example No. | R¹ | R¹⁸ | * | mp (decomp.) (° C.) | IR (ν cm⁻¹) (KBr) |
|---|---|---|---|---|---|
| 85 | PhCH₂— | Ph—N=N—C₆H₄—CH₃ (p) | R | 172–174 | 2400–3600 br, 3426, 3296, 1698, 1350, 1167 |
| 86 | PhCH₂— | Me₂N—C₆H₄—N=N—C₆H₄—CH₃ (p) | R | 93–94 | 2200–3700 br, 3431, 1735, 1391, 1154 |
| 87 | PhCH₂— | Ph—NH—C(=O)—NH—C₆H₄—CH₃ (p) | S | 203–204 | 2300–3700 br, 3358, 3262, 1718, 1686, 1660, 1313, 1159 |

| Example No. | $^1$H—NMR (δ ppm) d₆-DMSO |
|---|---|
| 85 | 2.75(dd, J=9.1, 13.7Hz, 1H), 2.98(dd, J=5.5, 13.7Hz, 1H), 3.96(ddd, J=5.5, 9.1, 9.1Hz, 1H), 8.51(d, J+9.1Hz, 1H) |
| 86 | 2.74(dd, J=9.1, 13.6Hz, 1H), 2.96(dd, J=5.7, 13.6Hz, 1H), 3.09(s, 6H), 3.93(dt, J=5.7, 9.1Hz, 1H), 8.39(d, J=9.1Hz, 1H) |
| 87 | 2.71(dd, J=9.1, 13.7Hz, 1H), 2.93(dd, J=5.6, 13.7Hz, 1H), 3.84(dt, J=5.6, 9.1Hz, 1H), 8.11(d, J=9.1Hz, 1H), 8.78(s, 1H), 9.06(s, 1H) |

TABLE 22

(Ia)

R¹⁸SO₂NH—*CH(R¹)—COOH

| Example No. | R¹ | R¹⁸ | * | mp (decomp.) (° C.) |
|---|---|---|---|---|
| 88 | (1H-indol-3-yl)CH₂— | Ph—NH—C(=O)—C₆H₄—CH₃ (p) | R | 103–106 |
| 89 | (CH₃)₂CH— | Ph—SO₂—NH—C₆H₄—CH₃ (p) | R | 96–99 |
| 90 | (CH₃)₂CH— | Ph—SO₂—NH—N=CH—C₆H₄—CH₃ (p) | R | 110–112 |
| 91 | PhCH₂— | Br—C₆H₄—SO₂—NH—C₆H₄—CH₃ (p) | R | 98–101 |

| Example No. | IR (ν cm⁻¹) (KBr) | Elemental analysis |
|---|---|---|

TABLE 22-continued (Ia)

$$R^{18}SO_2NH-\underset{*}{\overset{R^1}{C}}-COOH$$

| | | | |
|---|---|---|---|
| 88 | 1719, 1390, 1229 | — | |
| 89 | 1734, 1461, 1327, 1158 | $C_{17}H_{20}N_2O_6S_2$ .0.9Ethylether Calc. C: 51.63 H: 6.10 N: 5.85 S: 13.38 Foun. C: 51.23 H: 6.17 N: 5.87 S: 13.11 | |
| 90 | 1724, 1325, 1168 | $C_{18}H_{21}N_3O_6S_2$ .0.8Ethylether Calc. C: 51.05 H: 5.86 N: 8.42 S: 12.86 Foun. C: 50.75 H: 5.89 N: 8.15 S: 12.47 | |
| 91 | 1735, 1598, 1327, 1185 | $C_{21}H_{19}BrN_2O_6S_2$ .0.5CF$_3$COOH Calc. C: 44.30 H: 3.30 Br: 13.40 N: 4.70 S: 10.75 Foun. C: 44.62 H: 3.52 Br: 13.07 N: 4.64 S: 10.85 | |

Example 92 (Method B)

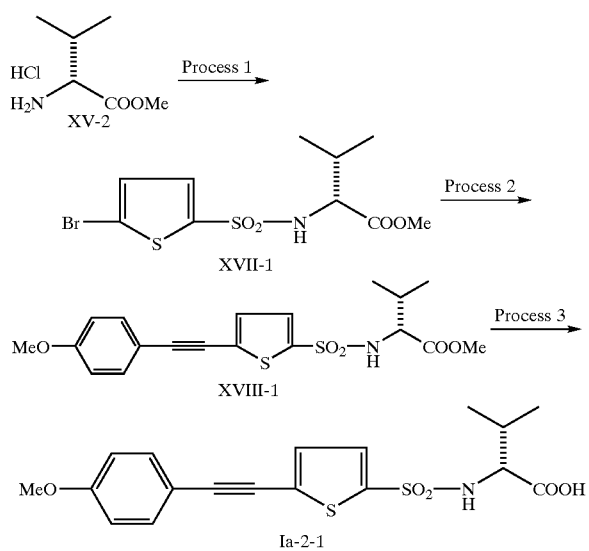

Process 1

To a solution of D-valine methylester hydrochloride (XV-2) (755 mg, 4.5 mmol) in dichloromethane(12 ml) was added N-methylmorpholine (1.49 ml, 3×4.5 mmol) and 5-bromo-2-thiophensulfonyl chloride (1.24 g, 1.05×4.5 mmol) was added under ice-cooling. After being stirred for 15 h. at room temperature, the reaction mixture was washed with 2N HCl, 5% NaHCO$_3$, and water. The organic layer was concentrated in vacuo, and dried over Na$_2$SO$_4$. The residue was subjected to silica gel column chromatography and the fractions eluting with ethyl acetate/hexane=1/3 were collected and washed with n-hexane to give 1.32 g of the desired compound (XVII-1).

Yield 82%. mp. 109–110° C. Elemental analysis $C_{10}H_{14}BrNO_4S2$ Calcd.: C; 33.71 H; 3.96 Br; 22.43 N; 3.93 S;1 8.00; Found: C; 33.75 H; 3.89 Br; 22.43 N; 3.96 S; 17.86; [α]$_D$: −34.5±0.7(c=1.012 CHCl$_3$ 25° C.); IR(CHCl$_3$, ν max cm$^{-1}$)1737,1356,1164,1138; NMR (CDCl$_3$, δ ppm): 0.89(d, J=6.8 Hz, 3H), 1.00(d, J=6.8 Hz, 3H), 2.00 (m, 1H), 3.60(s, 3H), 3.83(dd, J=5.2, 10.0 Hz, 1H), 5.20(d, J=10.0 Hz, 1H), 7.04(d, J=4.1 Hz, 1H), 7.32 (d, J=4.1 Hz, 1H).

Process 2

To a degassed solution of 400 mg (1.12 mmol) of compound (XVII-1) in 5 ml of dimethylformamide was added 222 mg (1.5×1.12 mmol) of 4-methoxyphenylacetylene and 21 mg (0.1×1.12 mmol) of copper iodide (I) under an argon atmosphere. Then 39 mg (0.05×1.12 mmol) of bis (triphenylphosphine)palladium dichloride (II) and 0.47 ml (3×1.12 mmol) of triethylamine were added to the reaction mixture. The resulting mixture was degassed and stirred overnight under an argon atmosphere at 50° C. The reaction mixture was diluted with ethyl acetate. The organic later was washed with 1N HCl, 5% NaHCO$_3$, and water, dried over Na$_2$SO$_4$, and concentrated in vacuo. The resulting residue was column chromatographed on silica gel. The fractions eluting with n-hexane/ethyl acetate=2/1 were collected and recrystallized from ethyl acetate/n-hexane to give 392 mg of the desired compound (XVIII-1). Yield 86%. mp. 131–132° C.

Elemental analysis $C_{19}H_{21}NO_5S_2$.0.2 H$_2$O; Calcd.: C; 55.51 H; 5.25 N; 3.41 S; 15.60; Found: C; 55.80 H; 5.19 N; 3.38 S; 15.36; IR(KBr, ν max cm$^{-1}$): 3268,2203,1736,1604, 1524,1348,1164. NMR(CDCl$_3$, δ ppm): 0.90(d, J=6.6 Hz, 3H), 1.00(d, J=7.0 Hz, 3H), 2.00(m, 1H), 3.60(s, 3H), 3.84(s, 3H), 3.86(dd, J=5.0, 10.2 Hz, 1H), 5.21(d, J=10.2 Hz, 1H), 6.90(d, J=9.0 Hz, 2H), 7.44(d, J=9.0 Hz, 2H), 7.12(d, J=4.0 Hz, 1H), 7.44(d, J=4.0 Hz, 1H).

Process 3

To a solution of 407 mg (1 mmol) of compound (XVII-1) in 8 ml of tetrahydrofuran and 8 ml of methanol was added 5.1 ml of IN NaOH. The resulting mixture was stirred for 6 h at 60° C. The reaction mixture was concentrated in vacuo to remove an organic solvent, and the residue was diluted with ethyl acetate. The mixture was acidified with aqueous solution of citric acid and extracted with ethyl acetate. The organic layer was washed with brine, dried over Na2SO$_4$, and concentrated in vacuo to give 373 mg of compound (Ia-2-1). Yield 100%. mp. 147–148° C.

IR (KBr, ν max cm$^{-1}$): 1710,1604,1351,1216. Elemental analysis $C_{18}H_{19}NO_5S_2$.0.2H$_2$O; Calcd.: C; 54.45 H; 4.92 N; 3.53 S; 16.15; Found: C; 54.39 H; 4.93 N; 3.79 S; 15.96;

Example 93–156

The compounds which were shown in Tables 23 to 30 were synthesized in a manner similar to those described in Example 92.

TABLE 23

(Ia)

$$R^{18}SO_2NH-\overset{R^1}{\underset{*}{C}H}-COOH$$

| Example No. | R¹ | R¹⁸ | * | mp (decomp.) (° C.) |
|---|---|---|---|---|
| 93 | indol-3-ylmethyl | phenyl-C≡C-(4-phenyl)- | R | 165–170 |
| 94 | indol-3-ylmethyl | 4-H₃CO-phenyl-C≡C-(4-phenyl)- | R | 223–226 |
| 95 | indol-3-ylmethyl | 4-HO-phenyl-C≡C-(4-phenyl)- | R | 216–218 |
| 96 | indol-3-ylmethyl | 4-H₃COCO-phenyl-C≡C-(4-phenyl)- | R | 111–114 |
| 97 | indol-3-ylmethyl | 4-F-phenyl-C≡C-(4-phenyl)- | R | 178–180 |
| 98 | indol-3-ylmethyl | 4-O₂N-phenyl-C≡C-(4-phenyl)- | R | 105–108 |
| 99 | indol-3-ylmethyl | 4-HOOC-phenyl-C≡C-(4-phenyl)- | R | >250 |
| 100 | indol-3-ylmethyl | 4-H₂N-phenyl-C≡C-(4-phenyl)- | R | 176–177 |

| Example No. | IR (ν cm⁻¹) (KBr) | Elemental analysis |
|---|---|---|
| 93 | 1590, 1316, 1137 | — |
| 94 | 1747, 1323, 1134 | $C_{26}H_{22}N_2O_5S$<br>Calc. C: 65.81 H: 4.67 N: 5.90 S: 6.76<br>Foun. C: 65.34 H: 4.90 N: 5.56 S: 6.40 |
| 95 | 1724, 1325, 1135 | — |
| 96 | 1739, 1336, 1163 | — |

TABLE 23-continued (Ia)

$$R^{18}SO_2NH-\overset{R^1}{\underset{*}{C}}H-COOH$$

| | | | | | | |
|---|---|---|---|---|---|---|
| 97 | 1710, 1511, 1329, 1161 | — | | | | |
| 98 | 1725, 1618, 1373, 1163 | — | | | | |
| 99 | 1706, 1606, 1350, 1164 | $C_{26}H_{20}N_2O_6S \cdot 0.4H_2O$ Calc. Foun. | C: 63.00 C: 62.99 | H: 4.23 H: 4.32 | N: 5.65 N: 5.82 | S: 6.47 S: 6.76 |
| 100 | 1735, 1633, 1321, 1173 | $C_{25}H_{21}N_3O_4S \cdot 0.8H_2O$ Calc. Foun. | C: 63.36 C: 63.45 | H: 4.81 H: 4.92 | N: 8.87 N: 8.77 | S: 6.77 S: 6.57 |

TABLE 24

(Ia)

$$R^{18}SO_2NH-\overset{R^1}{\underset{*}{C}}H-COOH$$

| Example No. | $R^1$ | $R^{18}$ | * | mp (decomp.) (° C.) |
|---|---|---|---|---|
| 101 | 1H-indol-3-ylmethyl | 4-methyl-phenyl-C≡C-(4-phenyl)- | R | 227–229 |
| 102 | 1H-indol-3-ylmethyl | HC≡C-(4-phenyl)-C≡C-(4-phenyl)- | R | 230–233 |
| 103 | 1H-indol-3-ylmethyl | 4-Me₂N-phenyl-C≡C-(4-phenyl)- | R | 234–236 |
| 104 | 1H-indol-3-ylmethyl | 4-H₃CO-phenyl-C≡C-(2-nitro-4-phenyl)- | R | >200 decomp. |
| 105 | (CH₃)₂CH— | 4-H₃CO-phenyl-C≡C-(4-phenyl)- | R | 146–149 |
| 106 | (CH₃)₂CH— | 4-O₂N-phenyl-C≡C-(4-phenyl)- | R | 231–232 |

TABLE 24-continued
(Ia)
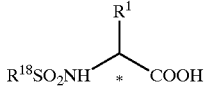
| 107 | (CH$_3$)$_2$CH— | 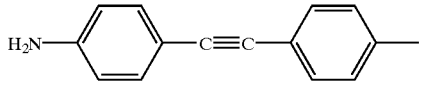 | R | 166–169 |
| 108 | (CH$_3$)$_2$CH— | 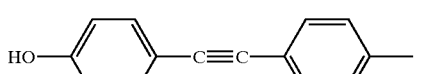 | R | 163–165 |
| Example No. | IR (ν cm$^{-1}$) (KBr) | Elemental analysis |
| --- | --- | --- |
| 101 | 1736, 1618 1398, 1168 | C$_{26}$H$_{22}$N$_2$O$_4$S 0.2H$_2$O<br>Calc. C: 67.57 H: 4.89 N: 6.06 S: 6.94<br>Foun. C: 67.66 H: 4.77 N: 6.09 S: 6.71 |
| 102 | 1735, 1654 1399, 1164 | — |
| 103 | 1732, 1631 1372, 1148 | — |
| 104 | 1600, 1558 1336, 1171 | — |
| 105 | 1795, 1718 1331, 1166 | — |
| 106 | 1719, 1595 1344, 1167 | C$_{19}$H$_{18}$N$_2$O$_6$S 0.1H$_2$O<br>Calc. C: 56.46 H: 4.54 N: 6.93 S: 7.93<br>Foun. C: 56.30 H: 4.37 N: 7.14 S: 7.85 |
| 107 | 1728, 1631 1372, 1148 | — |
| 108 | 1728, 1332 1172 | — |
TABLE 25
(Ia)
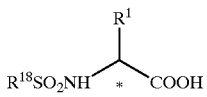
| Example No. | R$^1$ | R$^{18}$ | * | mp (decomp.) (° C.) |
| --- | --- | --- | --- | --- |
| 109 | (CH$_3$)$_2$CH— | 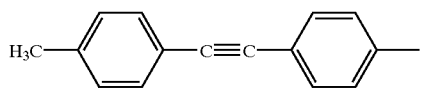 | R | 187–189 |
| 110 | (CH$_3$)$_2$CH— | 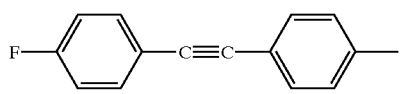 | R | 111–114 |

TABLE 25-continued $$R^{18}SO_2NH-\overset{R^1}{\underset{*}{C}H}-COOH \quad (Ia)$$

| No. | R¹ | R¹⁸ | mp (°C) |
|---|---|---|---|
| 111 | (CH₃)C— | 4-(4-methylphenylethynyl)-3-methoxyphenyl | 161–162 |
| 112 | CH₃CH₂(CH₃)CH— | 4-(4-methylphenylethynyl)-3-methoxyphenyl | 157–159 |
| 113 | PhCH₂— | 4-(4-methylphenylethynyl)-3-methoxyphenyl | 133–136 |
| 114 | PhCH₂— | 4-(4-methylphenylethynyl)-3-methylphenyl | 183–185 |
| 115 | PhCH₂— | 4-(4-methylphenylethynyl)-3-fluorophenyl | 166–168 |
| 116 | (CH₃)₂CH— | 4-(4-methylphenylethynyl)-3-hydroxyphenyl | 163–165 |

| Example No. | IR (ν cm⁻¹) (KBr) | Elemental analysis |
|---|---|---|
| 109 | 1720, 1656, 1319, 1165 | — |
| 110 | 1724, 1635, 1366, 1158 | — |
| 111 | 1711, 1683, 1600, 1328, 1159 | $C_{21}H_{23}NO_5S \cdot 1.3H_2O$<br>Calc. C: 59.36 H: 6.07 N: 3.30 S: 7.55<br>Foun. C: 59.36 H: 6.06 N: 3.50 S: 7.44 |
| 112 | 1732, 1680, 1329, 1167 | — |
| 113 | 1735, 1651, 1348, 1165 | — |
| 114 | 1727, 1604, 1335, 1182 | — |
| 115 | 1725, 1663, 1399, 1197 | $C_{23}H_{18}FNO_4S \cdot 0.3H_2O$<br>Calc. C: 64.41 H: 4.37 F: 4.43 N: 3.27 S: 7.48<br>Foun. C: 64.37 H: 4.38 F: 4.96 N: 3.31 S: 7.24 |
| 116 | 1728, 1332, 1172 | — |

TABLE 26

(Ia)

$$R^{18}SO_2NH-\overset{R^1}{\underset{*}{CH}}-COOH$$

| Example No. | $R^1$ | $R^{18}$ | * | mp (decomp.) (° C.) |
|---|---|---|---|---|
| 117 | indol-3-yl-CH₂— | 4-CH₃-C₆H₄-C≡C-C₆H₄- | R | 187–189 |
| 118 | indol-3-yl-CH₂— | 4-F-C₆H₄-C≡C-C₆H₄- | R | 111–114 |
| 119 | indol-3-yl-CH₂— | C₆H₅-C≡C-(thien-2,5-diyl)- | R | 167–169 |
| 120 | indol-3-yl-CH₂— | 2-NO₂-C₆H₄-C≡C-(thien-2,5-diyl)- | R | — |
| 121 | indol-3-yl-CH₂— | 4-CH₃O-C₆H₄-C≡C-(thien-2,5-diyl)- | R | — |
| 122 | indol-3-yl-CH₂— | 4-F-C₆H₄-C≡C-(thien-2,5-diyl)- | R | 103–106 |
| 123 | indol-3-yl-CH₂— | 4-CH₃-C₆H₄-C≡C-(thien-2,5-diyl)- | R | 180–182 |
| 124 | (CH₃)₂CH— | 4-CH₃O-C₆H₄-C≡C-(thien-2,5-diyl)- | R | 147–148 |

| Example No. | IR (ν cm⁻¹) (KBr) | Elemental analysis |
|---|---|---|
| 117 | 1720, 1656 1319, 1165 | — |
| 118 | 1724, 1635 1366, 1158 | — |
| 119 | 1585, 1318 1153 | — |
| 120 | 1605, | — |

TABLE 26-continued
(Ia)
$$R^{18}SO_2NH-\overset{R^1}{\underset{*}{C}H}-COOH$$
| | | |
|---|---|---|
| | 1523 | |
| | 1340, | |
| | 1151 | |
| 121 | 1604, | — |
| | 1524 | |
| | 1336, | |
| | 1173 | |
| 122 | 1721, | — |
| | 1620 | |
| | 1339, | |
| | 1163 | |
| 123 | 1729, | — |
| | 1675 | |
| | 1340, | |
| | 1168 | |
| 124 | 1710, | $C_{18}H_{19}NO_5S_2 \cdot 0.2H_2O$ |
| | 1604 | Calc. C: 54.45 H: 4.92 N: 3.53 S: 16.15 |
| | 1351, | Foun. C: 54.39 H: 4.93 N: 3.79 S: 15.96 |
| | 1216 | |
TABLE 27
(Ia)
$$R^{18}SO_2NH-\overset{R^1}{\underset{*}{C}H}-COOH$$
| Example No. | $R^1$ | $R^{18}$ | * | mp (decomp.) (° C.) |
|---|---|---|---|---|
| 125 | $(CH_3)_2CH-$ | 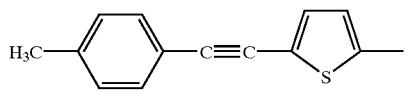 | R | 157–158 |
| 126 | $(CH_3)_2CH-$ | 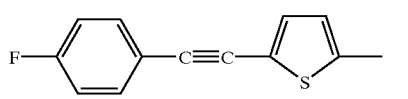 | R | 154–156 |
| 127 | 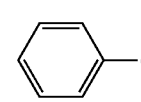 | 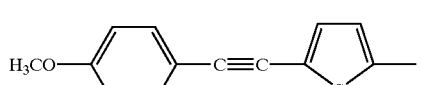 | R | 149–150 |
| 128 | 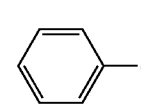 | 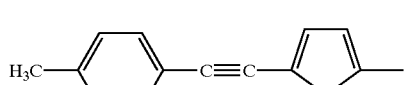 | R | 161–164 |
| 129 | 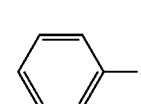 | 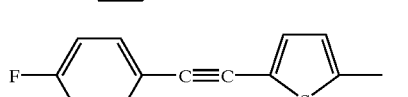 | R | 155–158 |
| 130 | 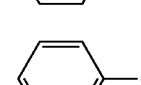 | 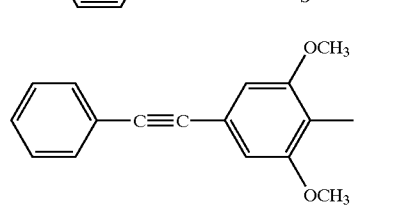 | R | — |

TABLE 27-continued $$R^{18}SO_2NH-\overset{R^1}{\underset{*}{C}H}-COOH \quad (Ia)$$

| Example | R¹ | R¹⁸ | * | |
|---|---|---|---|---|
| 131 | phenyl-CH₂- | 3,4,5-trimethoxyphenyl-C≡C-(4-methylphenyl) | R | — |
| 132 | phenyl-CH₂- | phenyl-C≡C-(4-methyl-3-nitrophenyl) | R | — |

| Example No. | IR (ν cm⁻¹) (KBr) | Elemental analysis |
|---|---|---|
| 125 | 1712, 1350, 1163 | $C_{18}H_{19}NO_4S_2 \cdot 0.2H_2O$<br>Calc. C: 56.73 H: 5.13 N: 3.68 S: 16.83<br>Foun. C: 57.03 H: 5.30 N: 3.89 S: 16.56 |
| 126 | 1710, 1499, 1356, 1165 | — |
| 127 | 1695, 1334, 1184 | $C_{22}H_{19}NO_5S_2 \cdot 0.2H_2O$<br>Calc. C: 59.36 H: 4.39 N: 3.15 S: 14.41<br>Foun. C: 59.43 H: 4.61 N: 3.25 S: 14.02 |
| 128 | 1710, 1329, 1180 | — |
| 129 | 1734, 1699, 1324, 1105 | $C_{21}H_{16}FNO_4S_2$<br>Calc. C: 58.73 H: 3.75 F: 4.42 N: 3.26 S: 14.93<br>Foun. C: 58.66 H: 3.93 F: 4.52 N: 3.33 S: 14.41 |
| 130 | — | — |
| 131 | — | — |
| 132 | — | — |

TABLE 28

$$R^{18}SO_2NH-\overset{R^1}{\underset{*}{C}H}-COOH \quad (Ia)$$

| Example No. | R¹ | R¹⁸ | * | mp (decomp.) (° C.) | IR (ν cm⁻¹) (KBr) | Elemental analysis |
|---|---|---|---|---|---|---|
| 133 | phenyl-CH₂- | cyclohexyl-C≡C-(4-methyl-3-nitrophenyl) | R | — | — | — |
| 134 | phenyl-CH₂- | CH₃(CH₂)₅-C≡C-(4-methylphenyl) | R | — | — | — |

TABLE 28-continued $$R^{18}SO_2NH-\overset{R^1}{\underset{*}{C}}H-COOH \quad (Ia)$$

| Example No. | R¹ | R¹⁸ | * | mp (decomp.) (° C.) | IR (ν cm⁻¹) (KBr) | Elemental analysis |
|---|---|---|---|---|---|---|
| 135 | Ph-CH₂— | H₃CO-C₆H₄-CH=CH-C₆H₄— | R | — | — | — |
| 136 | Ph-CH₂— | H₃CO-C₆H₄-CH=CH-(thiophene)— | R | — | — | — |
| 137 | Ph-CH₂— | F-C₆H₄-C≡C-(thiophene)— | R | — | — | — |
| 138 | Ph-CH₂— | Br-C₆H₄-C≡C-(thiophene)— | R | — | — | — |
| 139 | Ph-CH₂— | Cl-C₆H₄-C≡C-(thiophene)— | R | — | — | — |
| 140 | Ph-CH₂— | HO-C₆H₄-C≡C-(thiophene)— | R | — | — | — |

TABLE 29

$$R^{18}SO_2NH-\overset{R^1}{\underset{*}{C}}H-COOH \quad (Ia)$$

| Example No. | R¹ | R¹⁸ | * | mp (decomp.) (° C.) | IR (ν cm⁻¹) (KBr) | Elemental analysis |
|---|---|---|---|---|---|---|
| 141 | Ph-CH₂— | cyclopropyl-C₆H₄-C≡C-(thiophene)— | R | — | — | — |
| 142 | Ph-CH₂— | iPr-C₆H₄-C≡C-(thiophene)— | R | — | — | — |
| 143 | Ph-CH₂— | F₃C-C₆H₄-C≡C-(thiophene)— | R | — | — | — |
| 144 | Ph-CH₂— | Ph-C₆H₄-C≡C-(thiophene)— | R | — | — | — |

TABLE 29-continued (Ia)

$$R^{18}SO_2NH-\overset{R^1}{\underset{*}{C}H}-COOH$$

| Example No. | R¹ | R¹⁸ | * | mp (decomp.) (° C.) | IR (ν cm⁻¹) (KBr) | Elemental analysis |
|---|---|---|---|---|---|---|
| 145 | Ph-CH₂- | MeOC-C₆H₄-C≡C-(5-Me-thiophen-2-yl) | R | — | — | — |
| 146 | Ph-CH₂- | CH₂=CH-C₆H₄-C≡C-(5-Me-thiophen-2-yl) | R | — | — | — |
| 147 | Ph-CH₂- | HOOC-C₆H₄-C≡C-(5-Me-thiophen-2-yl) | R | — | — | — |
| 148 | Ph-CH₂- | MeOOC-C₆H₄-C≡C-(5-Me-thiophen-2-yl) | R | — | — | — |

TABLE 30

(Ia)

$$R^{18}SO_2NH-\overset{R^1}{\underset{*}{C}H}-COOH$$

| Example No. | R¹ | R¹⁸ | * | mp (decomp.) (° C.) | IR (νcm⁻¹) (KBr) | Elemental analysis |
|---|---|---|---|---|---|---|
| 149 | Ph-CH₂- | H₂NOC-C₆H₄-C≡C-(5-Me-thiophen-2-yl) | R | — | — | — |
| 150 | Ph-CH₂- | OHC-C₆H₄-C≡C-(5-Me-thiophen-2-yl) | R | — | — | — |
| 151 | Ph-CH₂- | O₂N-C₆H₄-C≡C-(5-Me-thiophen-2-yl) | R | — | — | — |
| 152 | Ph-CH₂- | H₂N-C₆H₄-C≡C-(5-Me-thiophen-2-yl) | R | — | — | — |
| 153 | Ph-CH₂- | Me₂N-C₆H₄-C≡C-(5-Me-thiophen-2-yl) | R | — | — | — |
| 154 | Ph-CH₂- | MeO₂S-C₆H₄-C≡C-(5-Me-thiophen-2-yl) | R | — | — | — |

TABLE 30-continued (Ia)

R¹⁸SO₂NH—*—COOH with R¹ on α-carbon

| Example No. | R¹ | R¹⁸ | * | mp (decomp.) (° C.) | IR (vcm⁻¹) (KBr) | Elemental analysis |
|---|---|---|---|---|---|---|
| 155 | Ph—CH₂— | HS—C₆H₄—C≡C—(thiophene)— | R | — | — | — |
| 156 | Ph—CH₂— | NC—C₆H₄—C≡C—(thiophene)— | R | — | — | — |

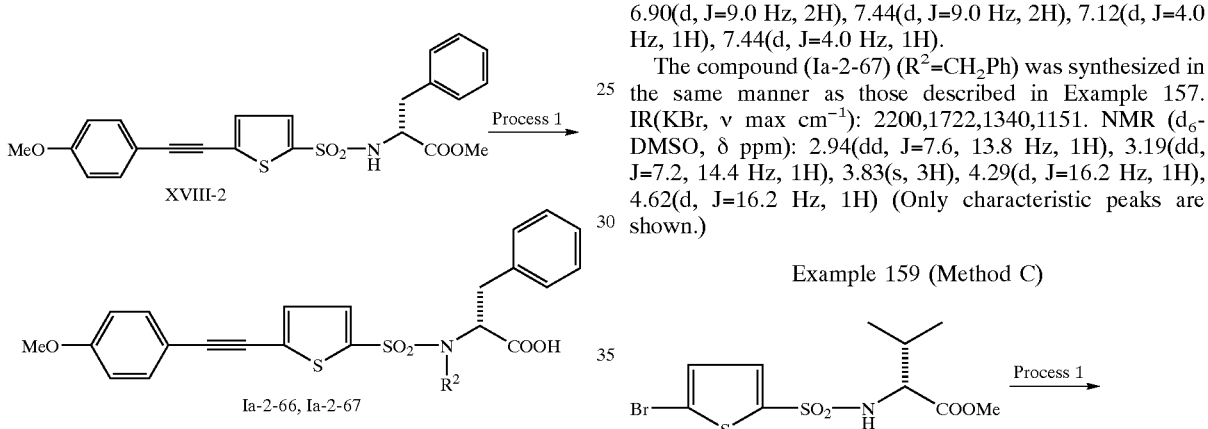

XVIII-2

Ia-2-66, Ia-2-67

Process 1 (R²=CH₃)

To a solution of 150 mg (0.33 mmol) of compound (XVIII-2) in 2 ml of dimethylformamide which was synthesized the same manner as those described in Example 96 was added 227 mg (5×0.33 mmol) of potassium carbonate and 0.1 ml (5×0.33 mmol) of methyl iodide, and the resulting mixture was stirred overnight at room temperature. The reaction mixture was poured into water and extracted with ethyl acetate. The organic layer was washed with water, dried over $Na_2SO_4$, and concentrated in vacuo to give 373 mg of N-methyl derivative as an oil. Yield 91%.

Elemental analysis $C_{24}H_{23}NO_5S_2$; Calcd.: C; 61.39 H; 4.94 N; 2.98 S; 13.66; Found: C; 61.22 H; 5.18 N; 2.93 S; 13.27;

Further, a solution of 140 mg of the above oily compound which was obtained the above process in 2 ml of methanol was added 0.6 ml of 1N NaOH, and the resulting mixture was stirred overnight at room temperature. The reaction mixture was acidified with 2N HCl and extracted with ethyl acetate. The organic layer was washed with water, dried over $Na_2SO_4$, and concentrated in vacuo to give 105 mg of compound (Ia-2-66) (R=Me). Yield 77%. mp. 185–186° C.

Elemental analysis $C_{23}H_{21}NO_5S$; Calcd.: C; 60.64 H; 4.65 N; 3.07 S; 14.08; Found: C; 60.56 H; 4.84 N; 3.01 S; 13.94. IR (KBr, ν max cm⁻¹): 3600–2300 br, 3426, 2203, 1710, 1604, 1503, 1344, 1151. NMR ($d_6$-DMSO, δ ppm): 2.88(s, 3H), 2.93(dd, J=12.0, 10.2 Hz, 1H), 3.19 (dd, J=14.2, 5.6 Hz, 1H), 3.81(s, 3H), 4.74(dd, J=5.4, 10.2 Hz, 1H), 6.99–7.04(m, 2H), 7.20–7.35(m, 7H), 7.52–7.56(m, 2H), 6.90(d, J=9.0 Hz, 2H), 7.44(d, J=9.0 Hz, 2H), 7.12(d, J=4.0 Hz, 1H), 7.44(d, J=4.0 Hz, 1H).

The compound (Ia-2-67) (R²=CH₂Ph) was synthesized in the same manner as those described in Example 157. IR(KBr, ν max cm⁻¹): 2200,1722,1340,1151. NMR ($d_6$-DMSO, δ ppm): 2.94(dd, J=7.6, 13.8 Hz, 1H), 3.19(dd, J=7.2, 14.4 Hz, 1H), 3.83(s, 3H), 4.29(d, J=16.2 Hz, 1H), 4.62(d, J=16.2 Hz, 1H) (Only characteristic peaks are shown.)

Example 159 (Method C)

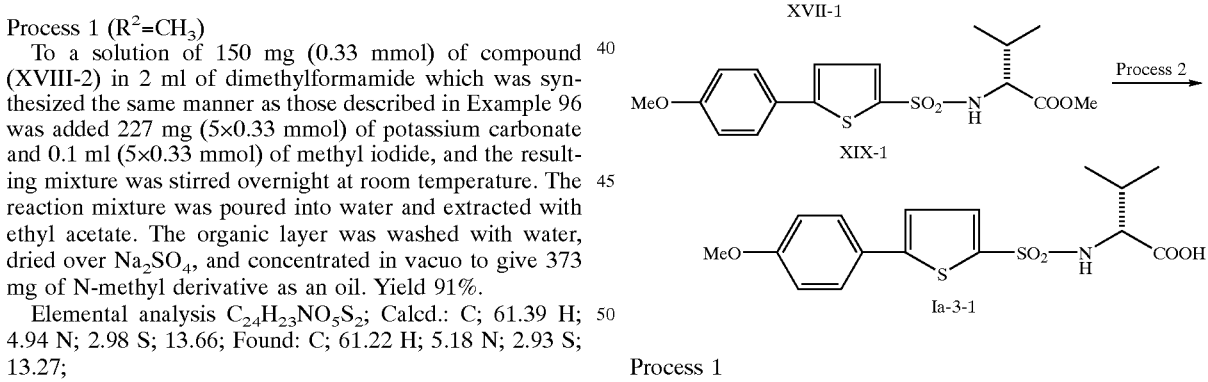

XVII-1

XIX-1

Ia-3-1

Process 1

To a solution of 500 mg (1.4 mmol) of compound(XVII-2) which was obtained Example 96 in 12 ml of dry tetrahydrofuran was added 387 mg (2×1.4 mmol) of powdery potassium carbonate, 319 mg (1.5×1.4 mmol) of 4-methoxyphenylboronic acid and 81 mg (0.05×1.4 mmol) of tetrakis(triphenylphosphine)palladium. The resulting mixture was stirred under argon atmosphere for 48 h at 75° C. The reaction mixture was diluted with ethyl acetate. The organic layer was washed with 1N HCl, 5% NaHCO₃ aq., and water, dried over $Na_2SO_4$, and concentrated in vacuo. The residue was column chromatographed on silica gel. The fractions eluting with n-hexane/ethyl acetate=3/1 were collected and recrystallized from n-hexane to give 447 mg of the desired compound (XIX-1). Yield 83%. mp. 122–123° C.

Elemental analysis C$_{17}$H$_{21}$NO$_5$S$_2$; Calcd.: C; 53.25 H; 5.52 N; 3.65 S; 16.72; Found: C; 53.26 H; 5.50 N; 3.69 S; 16.63; [α]$_D$ −21.7±0.6 (c=1.000 DMSO 25° C.); IR (KBr, ν max cm$^{-1}$): 1735,1605,1505,1350,1167,1136; NMR (CDCl$_3$, δ ppm): 0.90(d, J=7.0 Hz, 3H), 1.00(d, J=6.6 Hz, 3H), 2.10(m, 1H), 3.54(s, 3H), 3.85(s, 3H), 3.87(dd, J=5.0, 10.2 Hz, 1H), 5.20(d, J=10.2 Hz, 1H), 6.94(d, J=9.0 Hz, 2H), 7.52(d, J=9.0 Hz, 2H), 7.11(d, J=4.0 Hz, 1H), 7.49(d, J=4.0 Hz, 1H).

Process 2

To a solution of 390 mg (1.01 mmol) of compound (XIX-1) in 8 ml of tetrahydrofuran and 8 ml of methanol was added 5.1 ml of 1N NaOH, and resulting mixture was stirred at 60° C. for 6 h. The reaction mixture was concentrated in vacuo to remove an organic solvent. The resulting residue was diluted with ethyl acetate. The mixture was acidified with aqueous solution of citric acid and extracted with ethyl acetate. The organic layer was washed with brine, dried over Na$_2$SO$_4$, and concentrated in vacuo to give 373 mg of compound (Ia-3-1). Yield 100%. mp.: 174–176° C. IR(KBr, ν max cm$^{-1}$): 1735, 1503, 1343, 1163.

Example 160–175

The compounds which were shown in Tables 31 to 32 were synthesized in a manner similar to those described in Example 159,.

TABLE 31

(Ia)

R$^{18}$SO$_2$NH—*CH(R$^1$)—COOH

| Example No. | R$^1$ | R$^{18}$ | * | mp (decomp.) (° C.) | IR (ν cm$^{-1}$) (KBr) | Elemental analysis |
|---|---|---|---|---|---|---|
| 160 | indol-3-ylmethyl | H$_3$CO—C$_6$H$_4$—thienyl | R | 93–96 | 1667, 1337, 1180 | — |
| 161 | indol-3-ylmethyl | H$_3$C—C$_6$H$_4$—thienyl | R | 157–159 | 1670, 1339, 1194 | — |
| 162 | indol-3-ylmethyl | F—C$_6$H$_4$—thienyl | R | 168–171 | 1725, 1598, 1371, 1185 | — |
| 163 | indol-3-ylmethyl | H$_3$CS—C$_6$H$_4$—thienyl | R | 226–230 | 1735, 1341, 1159 | C$_{22}$H$_{20}$N$_2$O$_4$S$_3$·0.4H$_2$O Calc. C:55.07 H:4.37 N:5.84 S:20.05 Foun. C:55.35 H:4.43 N:6.04 S:19.65 |
| 164 | (CH$_3$)$_2$CH— | H$_3$CO—C$_6$H$_4$—thienyl | R | 174–176 | 1735, 1503, 1343, 1163 | — |
| 165 | (CH$_3$)$_2$CH— | H$_3$C—C$_6$H$_4$—thienyl | R | 165–167 | 1713, 1353, 1163 | — |
| 166 | (CH$_3$)$_2$CH— | F—C$_6$H$_4$—thienyl | R | 146–147 | 1702, 1504, 1352, 1168 | C$_{15}$H$_{16}$FNO$_4$S$_2$·0.1H$_2$O Calc. C:50.15 H:4.55 F:5.29 N:3.90 S:17.85 Foun. C:49.99 H:4.58 F:5.22 N:4.05 S:17.77 |
| 167 | (CH$_3$)$_2$CH— | H$_3$CS—C$_6$H$_4$—thienyl | R | 157–159 | 1747, 1324, 1159 | C$_{16}$H$_{19}$NO$_4$S$_3$ Calc. C:49.85 H:4.97 N:3.63 S:24.95 Foun. C:49.70 H:5.00 N:3.93 S:24.96 |

TABLE 32

(Ia)

$$R^{18}SO_2NH-\underset{*}{CH}(R^1)-COOH$$

| Example No. | R¹ | R¹⁸ | * | mp (decomp.) (° C.) | IR (ν cm⁻¹) (KBr) | Elemental analysis |
|---|---|---|---|---|---|---|
| 168 | PhCH₂— | H₃CO-C₆H₄-thienyl- | R | 161–165 | 1735, 1698 1374, 1163 | C₂₀H₁₉NO₅S₂ Calc. C:57.54 H:4.59 N:3.35 S:15.36 Foun. C:57.62 H:4.72 N:3.52 S:15.27 |
| 169 | PhCH₂— | H₃C-C₆H₄-thienyl- | R | 166–167 | 1713, 1609 1378, 1194 | C₂₀H₁₉NO₄S₂ Calc. C:59.83 H:4.77 N:3.49 S:15.97 Foun. C:59.77 H:4.86 N:3.61 S:15.86 |
| 170 | PhCH₂— | F-C₆H₄-thienyl- | R | 174–175 | 1721, 1654 1365, 1148 | C₁₉H₁₆FNO₄S₂ Calc. C:56.28 H:3.98 F:4.09 N:3.45 S:15.82 Foun. C:56.33 H:4.09 F:4.65 N:3.65 S:15.84 |
| 171 | PhCH₂— | H₃CS-C₆H₄-thienyl- | R | 203–205 | 1750, 1730 1428, 1325 1155 | C₂₀H₁₉NO₄S₃·0.2H₂O Calc. C:54.95 H:4.47 N:3.20 S:22.00 Foun. C:55.05 H:4.52 N:3.34 S:22.04 |
| 172 | PhCH₂— | H₂N-C₆H₄-thienyl- | R | — | — | — |
| 173 | PhCH₂— | Me₂N-C₆H₄-thienyl- | R | — | — | — |
| 174 | PhCH₂— | F₃C-C₆H₄-thienyl- | R | — | — | — |
| 175 | PhCH₂— | NC-C₆H₄-thienyl- | R | — | — | — |

Example 176 (Method D)

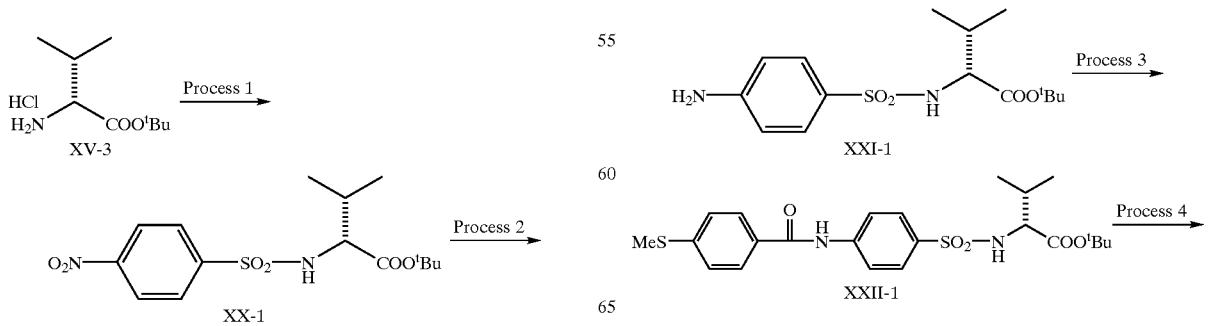

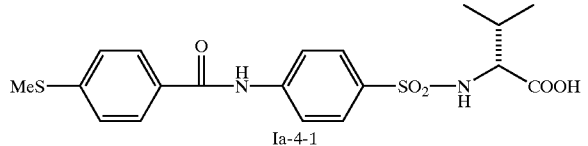

Ia-4-1

Process 1

To a solution of 10 g (47.68 mmol) of D-valine tert-butyl ester hydrochloride (XV-3) in 100 ml of dichloromethane was added 15.7 ml (3×47.68 mmol) of N-methylmorpholine and 14.1 g (1.2×47.68 mmol) of 4-nitrobenzenesulfonyl chloride under ice-cooling. After being stirred for 5 h at room temperature the reaction mixture was washed with 2N HCl, 5% NaHCO$_3$, water. The organic layer was dried over Na2SO$_4$ and concentrated in vacuo, and the resulting residue was recrystallized from dichloromethane/n-hexane to give 13.3g of the desired compound (XX-1). Yield 77.8%. mp. 89–90° C.

Elemental analysis C$_{15}$H$_{22}$N$_2$O$_6$S; Calcd.: C; 50.27 H; 6.19 N; 7.82 S; 8.95; Found: C; 50.04 H; 6.10 N; 7.89 S; 8.84; [α]$_D$ −2.9±0.8(c=0.512 DMSO 23° C.) IR(KBr, ν max cm$^{-1}$): 3430 br, 3301, 1722, 1698, 1525, 1362, 1348, 1181, 1174, 1159.

Process 2

A solution of 13.29 g (37.08 mmol) of compound (XX-1) in 200 ml of methanol was hydrogenated using 10% Pd/C (1 g) for 2 h at room temperature. The reaction mixture was filtered off and the filtrate was concentrated in vacuo. The residue was recrystallized from acetone/n-hexane to give 11.5 g of amine derivative (XXI-1). Yield 94.4%. mp. 164–166° C.

Elemental analysis C$_{15}$H$_{24}$N$_2$O$_4$S; Calcd.: C; 54.86 H; 7.37 N; 8.53 S; 9.76; Found: C; 54.84 H; 7.33 N; 8 63 S; 9.50; [α]$_D$ +10.3±1.0(c=0.515 DMSO 23° C.); IR(KBr, ν max cm$^{-1}$): 3461, 3375, 1716, 1638, 1598, 1344, 1313. NMR(d-DMSO, δ ppm): 0.80(d, J=6.8 Hz, 3H), 0.82(d, J=6.6 Hz, 3H), 1.23(s, 9H), 1.83(m, 1H), 3.30(m, 1H), 5.86(s, 2H), 6.56(d, J=8.8 Hz, 2H), 7.36(d, J=8.6 Hz, 2H), 7.47(d, J=9.6 Hz, 1H).

Process 3

To a solution of 328 mg (1 mmol) of compound (XXI-1) in 10 ml of dichloromethane was added 0.33 ml (3×1 mmol) of N-methylmorpholine and 280 mg (1.5×1 mmol) of 4-(methylthio)benzoyl chloride under ice-cooling. The reaction mixture was stirred overnight at room temperature. To the reaction mixture was added ethyl ether and precipitation were collected and washed with ice-water and ethyl ether, The solid were recrystallized from acetone/ethyl ether to give 433 mg of the desired compound (XXII-1). Yield 90.5%. mp. 235–238° C.

Elemental analysis C$_{23}$H$_{30}$N$_2$O$_5$S2; Calcd.: C; 57.72 H; 6.32 N; 5.85 S; 13.40; Found: C; 57.63 H; 6.28 N; 5.86 S; 13.20; [α]$_D$ +5.7±0.9(c=0.512 DMSO 25° C.) IR(KBr, ν max cm$^{-1}$): 3366, 3284, 1713, 1667, 1592, 1514, 1498, 1341, 1317. NMR(d$_6$-DMSO, δ ppm) : 0.82(d, J=6.6 Hz, 3H), 0.84(d, J=6.8 Hz, 3H), 1.22(s, 9H), 1.91(m, 1H), 2.55(s, 3H), 3.32(s, 3H), 3.44(dd, J=6.2, 8.6 Hz, 1H), 7.40(d, J=8.6 Hz, 2H), 7.73(d, J=8.6 Hz, 2H), 7.90–8.01(m, 5H), 10.48 (s, 1H).

Process 4

To a solution of 405 mg (0.85 mmol) of compound (XXII-1) in 3 ml of dichloromethane was added 3.3 ml (50×0.85 mmol) of trifluoroacetic acid and resulting mixture was stirred for 2 h at room temperature. The reaction mixture was concentrated in vacuo and the resulting residue was washed with ethyl ether to give 340 mg of the desired compound (Ia-4-1). Yield 94.7%. mp. 231–234° C. IR(KBr, ν max cm$^{-1}$): 1748, 1655, 1592, 1323, 1161.

Elemental analysis C$_{19}$H$_{22}$N$_2$O$_5$S$_2$ . 0.1CF$_3$COOH; Calcd.: C; 53.14 H; 5.13 N; 6.46 S; 14.78; Found: C; 53.48 H; 5.31 N; 6.57 S; 15.06;

Example 177–208

The compounds which were shown in Tables 33 to 36 were synthesized in a manner similar to those described in Example 176.

TABLE 33

(Ia)

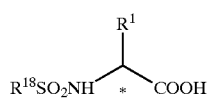

| Example No. | R$^1$ | R$^{18}$ |
|---|---|---|
| 177 | indol-3-yl-CH$_2$— | phenyl-C(O)-NH-(4-phenyl)— |
| 178 | indol-3-yl-CH$_2$— | H$_3$CO-(4-phenyl)-C(O)-NH-(4-phenyl)— |
| 179 | indol-3-yl-CH$_2$— | H$_2$N-(4-phenyl)-C(O)-NH-(4-phenyl)— |

TABLE 33-continued $$R^{18}SO_2NH-\overset{R^1}{\underset{*}{C}}H-COOH \quad (Ia)$$

| No. | R¹ | R¹⁸ |
|---|---|---|
| 180 | indol-3-yl-CH₂— | 4-O₂N-C₆H₄-C(O)NH-C₆H₄-4- |
| 181 | indol-3-yl-CH₂— | 4-(H₃C)₂N-C₆H₄-C(O)NH-C₆H₄-4- |
| 182 | indol-3-yl-CH₂— | 4-H₃C-C₆H₄-C(O)NH-C₆H₄-4- |
| 183 | indol-3-yl-CH₂— | 4-Br-C₆H₄-C(O)NH-C₆H₄-4- |
| 184 | indol-3-yl-CH₂— | 4-H₃CS-C₆H₄-C(O)NH-C₆H₄-4- |

| Example No. | * | mp (decomp.) (° C.) | IR (ν cm⁻¹) (KBr) | Elemental analysis |
|---|---|---|---|---|
| 177 | R | 215–217 | 1732, 1641 | — |
|  |  |  | 1341, 1163 |  |
| 178 | R | 233–234 | 1726, 1655 | $C_{25}H_{23}N_3O_6S \cdot 0.9H_2O$ |
|  |  |  | 1323, 1177 | Calc. C:58.91 H:4.90 N:8.24 S:6.29 |
|  |  |  |  | Foun. C:58.97 H:5.07 N:7.95 S:6.10 |
| 179 | R | 216–218 | 1723, 1633 | — |
|  |  |  | 1361, 1149 |  |
| 180 | R | 211–213 | 1719, 1629 | $C_{24}H_{20}N_4O_7S \cdot 1.1H_2O$ |
|  |  |  | 1340, 1156 | Calc. C:54.56 H:4.24 N:10.60 S:6.07 |
|  |  |  |  | Foun. C:54.51 H:4.32 N:10.83 S:6.15 |
| 181 | R | 236–238 | 1732, 1653 | $C_{26}H_{26}N_4O_5S \cdot 0.9H_2O$ |
|  |  |  | 1399, 1199 | Calc. C:59.73 H:5.36 N:10.72 S:6.13 |
|  |  |  |  | Foun. C:59.58 H:5.23 N:10.85 S:6.47 |
| 182 | R | 240–244 | 1731, 1656 | $C_{25}H_{23}N_3O_5S \cdot 0.9H_2O$ |
|  |  |  | 1591, 1327 | Calc. C:60.82 H:5.06 N:8.51 S:6.49 |
|  |  |  | 1160 | Foun. C:60.83 H:5.19 N:8.66 S:6.66 |
| 183 | R | 215–218 | 1727, 1668 | $C_{24}H_{20}BrN_3O_5S \cdot 0.6H_2O$ |
|  |  |  | 1590, 1316 | Calc. C:52.11 H:3.86 Br:14.44 N:7.60 S:5.80 |
|  |  |  | 1154 | Foun. C:52.13 H:4.04 Br:14.57 N:7.43 S:5.70 |
| 184 | R | 244–249 | 1728, 1653 | $C_{25}H_{23}N_3O_5S_2 \cdot 0.7H_2O$ |
|  |  |  | 1593, 1323 | Calc. C:57.50 H:4.71 N:8.05 S:12.28 |
|  |  |  | 1159 | Foun. C:57.63 H:4.79 N:8.00 S:12.08 |

TABLE 34

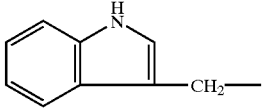

| Example No. | R¹ | R¹⁸ |
|---|---|---|
| 185 | 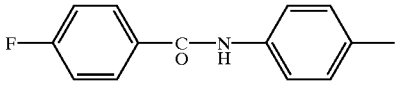 | 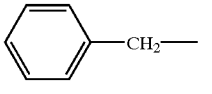 |
| 186 | 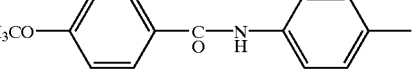 | 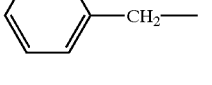 |
| 187 | 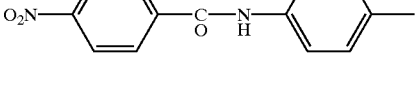 | 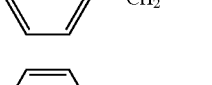 |
| 188 | 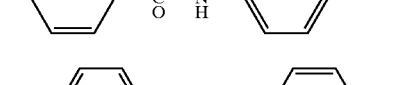 |  |
| 189 |  | 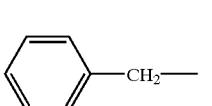 |
| 190 | 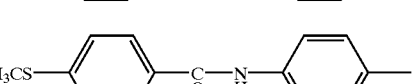 | 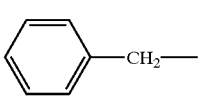 |
| 191 | 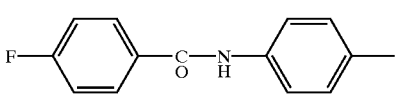 | 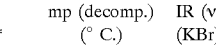 |
| 192 |  | |

| Example No. | * | mp (decomp.) (° C.) | IR (ν cm⁻¹) (KBr) | Elemental analysis |
|---|---|---|---|---|
| 185 | R | 170–175 | 1730, 1651 1603, 1333 1161 | $C_{24}H_{20}FN_3O_5S \cdot 0.6H_2O$<br>Calc. C:58.55 H:4.34 F:3.86 N:8.54 S:6.51<br>Foun. C:58.67 H:4.51 F:3.77 N:8.42 8:6.47 |
| 186 | R | 237–239 | 1723, 1651 1591, 1322 1161 | $C_{23}H_{22}N_2O_6S$<br>Calc. C:60.78 H:4.88 N:6.16 S:7.05<br>Foun. C:60.50 H:4.99 N:6.14 S:7.31 |
| 187 | R | 235–239 | 1719, 1672 1593, 1327 1159 | $C_{22}H_{19}N_3O_7S$<br>Calc. C:56.29 H:4.08 N:8.95 S:6.83<br>Foun. C:56.01 H:4.09 N:8.93 S:6.75 |
| 188 | R | 114–115 | 1748, 1658 1592, 1325 1159 | $C_{22}H_{20}N_2O_5S \cdot 0.5CF_3COOH$<br>Calc. C:57.37 H:4.29 N:5.82 S:6.68<br>Foun. C:57.53 H:4.45 N:5.75 S:7.11 |
| 189 | R | 242–243 | 1743, 1670 1591, 1335 1167 | $C_{22}H_{19}BrN_2O_5S \cdot CF_3COOH$<br>Calc. C:46.69 H:3.27 Br:12.94 N:4.54 S:5.19<br>Foun. C:46.79 H:3.41 Br:12.86 N:4.57 S:5.37 |
| 190 | R | 242–244 | 1752, 1726 1656, 1591 1324, 1160 | $C_{23}H_{22}N_2O_5S$<br>Calc. C:63.00 H:5.06 N:6.39 S:7.31<br>Foun. C:62.70 H:5.13 N:6.36 S:7.36 |
| 191 | R | 232–235 | 1742, 1667 1591, 1334 1161 | $C_{23}H_{22}N_2O_5S_2 \cdot 0.8CF_3COOH$<br>Calc. C:52.59 H:4.09 N:4.99 S:11.42<br>Foun. C:52.77 H:4.24 N:5.12 S:11.58 |

TABLE 34-continued (Ia)

R¹⁸SO₂NH—*CH(R¹)—COOH

| 192 | R | 218–220 | 1737, 1651 | C₂₂H₁₉FN₂O₅S |
| --- | --- | --- | --- | --- |
| | | | 1598, 1324 | Calc. C:59.72 H:4.33 F:4.29 N:6.33 S:7.25 |
| | | | 1160 | Foun. C:59.59 H:4.42 F:4.30 N:6.37 S:7.24 |

TABLE 35

(Ia)

R¹⁸SO₂NH—*CH(R¹)—COOH

| Example No. | R¹ | R¹⁸ |
| --- | --- | --- |
| 193 | C₆H₅—CH₂— | 6-Cl-pyridin-3-yl-C(O)NH-C₆H₄- (p-tolyl) |
| 194 | C₆H₅—CH₂— | 6-CH₃-2-Cl-pyridin-3-yl-C(O)NH-C₆H₄- (p-tolyl) |
| 195 | (CH₃)₂CH— | 4-phenyl-C₆H₄—C(O)NH—C₆H₄— (p-tolyl) |
| 196 | (CH₃)₂CH— | 4-CH₃-C₆H₄—C(O)NH—C₆H₄— (p-tolyl) |
| 197 | (CH₃)₂CH— | 4-CH₃S-C₆H₄—C(O)NH—C₆H₄— (p-tolyl) |
| 198 | (CH₃)₂CH— | 4-F-C₆H₄—C(O)NH—C₆H₄— (p-tolyl) |
| 199 | (CH₃)₂CH— | C₆H₅—C(O)NH—C₆H₄— (p-tolyl) |
| 200 | (CH₃)₂CH— | 4-CH₃O-C₆H₄—C(O)NH—C₆H₄— (p-tolyl) |

| Example No. | * | mp (decomp.) (° C.) | IR (ν cm⁻¹) (KBr) | Elemental analysis |
| --- | --- | --- | --- | --- |
| 193 | R | 201–203 | 1724, 1673 | C₂₁H₁₈ClN₃O₅S |
| | | | 1592, 1326 | Calc. C:54.84 H:3.94 Cl:7.71 N:9.14 S:6.97 |
| | | | 1156 | Foun. C:54.39 H:4.06 Cl:7.42 N:8.98 S:6.99 |
| 194 | R | 206–208 | 1725, 1682 | C₂₂H₂₀ClN₃O₅S.0.1CF₃COOH |
| | | | 1592, 1332 | Calc. C:55.15 H:4.19 Cl:7.33 N:8.69 S:6.63 |
| | | | 1160 | Foun. C:55.25 H:4.28 Cl:7.10 N:8.80 S:6.80 |

TABLE 35-continued (Ia)

$$R^{18}SO_2NH-\underset{*}{CH}(R^1)-COOH$$

| | | | | | |
|---|---|---|---|---|---|
| 195 | R | 254–256 | 1748, 1659 | | $C_{24}H_{24}N_2O_5S\cdot 0.5H_2O$ |
| | | | 1590, 1324 | | Calc. C:62.46 H:5.46 N:6.07 S:6.95 |
| | | | 1161 | | Foun. C:62.42 H:5.54 N:6.26 S:6.97 |
| 196 | R | 227–229 | 1749, 1658 | | $C_{19}H_{22}N_2O_5S\cdot 0.2H_2O$ |
| | | | 1592, 1323 | | Calc. C:57.91 H:5.73 N:7.11 S:8.14 |
| | | | 1161 | | Foun. C:57.94 H:5.69 N:7.03 S:8.14 |
| 197 | R | 231–234 | 1748, 1655 | | $C_{19}H_{22}N_2O_5S_2\cdot 0.1CF_3COOH$ |
| | | | 1592, 1323 | | Calc. C:53.14 H:5.13 N:6.46 S:14.78 |
| | | | 1161 | | Foun. C:53.48 H:5.31 N:6.57 S:15.06 |
| 198 | R | 235–236 | 1749, 1726 | | $C_{18}H_{19}FN_2O_5S\cdot 0.1CF_3COOH$ |
| | | | 1668, 1597 | | Calc. C:53.86 H:4.74 F:6.09 N:6.90 S:7.90 |
| | | | 1322, 1160 | | Foun. C:53.82 H:4.85 F:5.60 N:6.93 S:7.78 |
| 199 | R | 226–227 | 1728, 1661 | | $C_{18}H_{20}N_2O_5S\cdot 0.1H_2O$ |
| | | | 1591, 1317 | | Calc. C:57.16 H:5.38 N:7.41 S:8.48 |
| | | | 1159 | | Foun. C:57.01 H:5.46 N:7.57 S:8.57 |
| 200 | R | 220–221 | 1696, 1654 | | $C_{19}H_{22}N_2O_6S\cdot 0.2H_2O$ |
| | | | 1591, 1317 | | Calc. C:55.65 H:5.51 N:6.83 S:7.82 |
| | | | 1255 | | Foun. C:55.63 H:5.48 N:7.03 S:7.75 |

TABLE 36

(Ia)

$$R^{18}SO_2NH-\underset{*}{CH}(R^1)-COOH$$

| Example No. | $R^1$ | $R^{18}$ |
|---|---|---|
| 201 | $(CH_3)_2CH-$ | 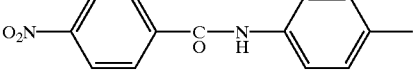 |
| 202 | $(CH_3)_2CH-$ | 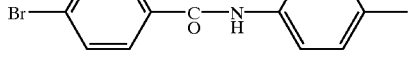 |
| 203 | $(CH_3)_3C-$ | 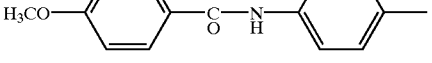 |
| 204 | 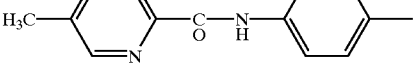 | |
| 205 | | 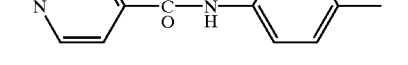 |
| 206 | | 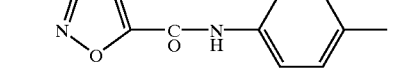 |
| 207 | | 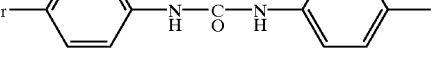 |

TABLE 36-continued (Ia)

$$R^{18}SO_2NH-\overset{R^1}{\underset{*}{C}H}-COOH$$

| 208 | Ph-CH$_2$- | H$_2$N-C$_6$H$_4$- | -C(O)NH-C$_6$H$_4$-CH$_3$ |

| Example No. | * | mp (decomp.) (° C.) | IR (ν cm$^{-1}$) (KBr) | Elemental analysis |
|---|---|---|---|---|
| 201 | R | 240–242 | 1726, 1688 1591, 1347 1166 | C$_{18}$H$_{19}$N$_3$O$_7$S·0.4H$_2$O Calc. C:50.44 H:4.66 N:9.80 S:7.48 Foun. C:50.40 H:4.55 N:9.90 S:7.44 |
| 202 | R | 229–230 | 1726, 1663 1592, 1318 1159 | C$_{18}$H$_{19}$BrN$_2$O$_5$S·0.2Ethylether Calc. C:48.03 H:4.50 Br:17.00 N:5.96 S:6.82 Foun. C:48.04 H:4.61 Br:16.83 N:5.96 S:6.86 |
| 203 | R | 214–216 | 1659, 1591 1316, 1159 | C$_{20}$H$_{24}$N$_2$O$_6$S·0.4H$_2$O Calc. C:56.17 H:5.84 N:6.55 S:7.50 Foun. C:56.21 H:6.02 N:6.50 S:1.33 |
| 204 | R | 236–237 | 1723, 1679 1590, 1337 1162 | C$_{21}$H$_{20}$N$_4$O$_5$S·0.25CF$_3$COOH Calc. C:55.06 H:4.35 N:11.95 S:6.84 Foun. C:54.80 H:4.90 N:12.16 S:7.10 |
| 205 | R | 272–275 | 1719, 1672 1594, 1339 1165 | C$_{21}$H$_{19}$N$_3$O$_5$S Calc. C:59.28 H:4.50 N:9.88 S:7.54 Foun. C:58.84 H:4.58 N:9.71 S:7.36 |
| 206 | R | 214–215 | 1733, 1685 1594, 1319 1154 | C$_{20}$H$_{19}$N$_3$O$_6$S Calc. C:55.94 H:4.46 N:9.78 S:7.47 Foun. C:55.50 H:4.47 N:9.74 S:7.31 |
| 207 | R | 217–220 | 1732, 1679 1592, 1312 1155 | — |
| 208 | R | — | — | — |

Example 209 (Method E)

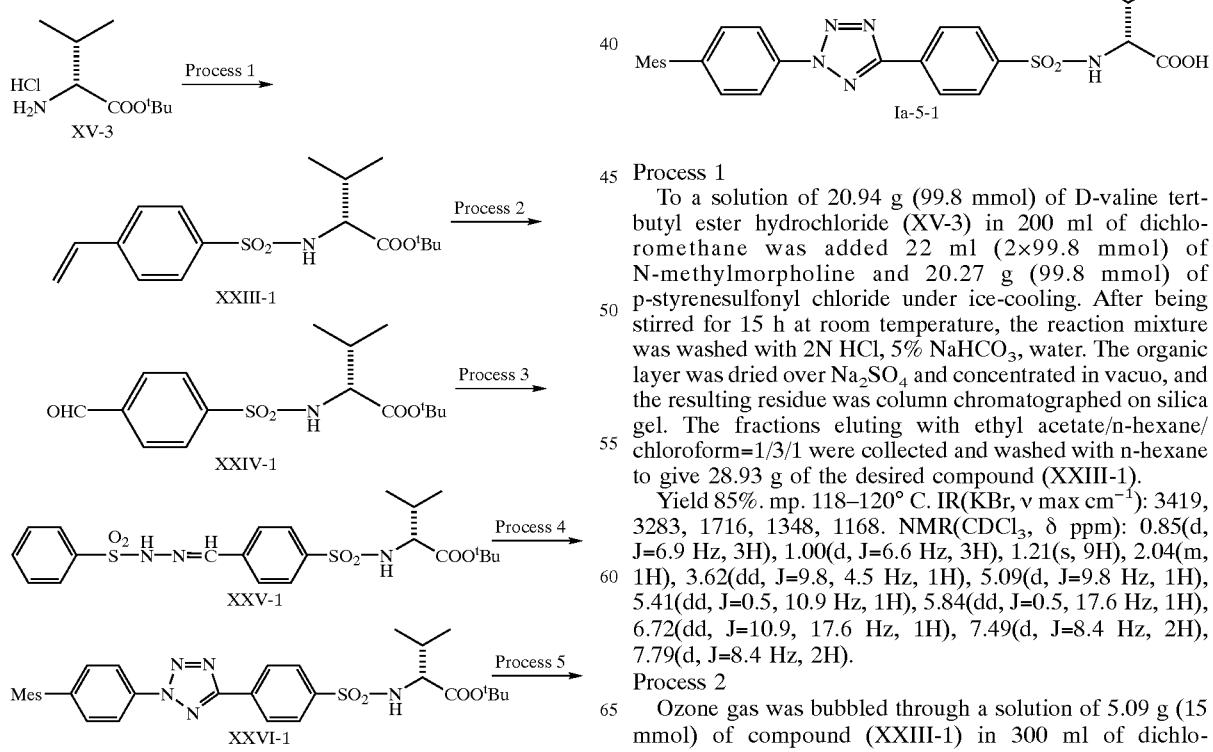

Process 1

To a solution of 20.94 g (99.8 mmol) of D-valine tert-butyl ester hydrochloride (XV-3) in 200 ml of dichloromethane was added 22 ml (2×99.8 mmol) of N-methylmorpholine and 20.27 g (99.8 mmol) of p-styrenesulfonyl chloride under ice-cooling. After being stirred for 15 h at room temperature, the reaction mixture was washed with 2N HCl, 5% NaHCO$_3$, water. The organic layer was dried over Na$_2$SO$_4$ and concentrated in vacuo, and the resulting residue was column chromatographed on silica gel. The fractions eluting with ethyl acetate/n-hexane/chloroform=1/3/1 were collected and washed with n-hexane to give 28.93 g of the desired compound (XXIII-1).

Yield 85%. mp. 118–120° C. IR(KBr, ν max cm$^{-1}$): 3419, 3283, 1716, 1348, 1168. NMR(CDCl$_3$, δ ppm): 0.85(d, J=6.9 Hz, 3H), 1.00(d, J=6.6 Hz, 3H), 1.21(s, 9H), 2.04(m, 1H), 3.62(dd, J=9.8, 4.5 Hz, 1H), 5.09(d, J=9.8 Hz, 1H), 5.41(dd, J=0.5, 10.9 Hz, 1H), 5.84(dd, J=0.5, 17.6 Hz, 1H), 6.72(dd, J=10.9, 17.6 Hz, 1H), 7.49(d, J=8.4 Hz, 2H), 7.79(d, J=8.4 Hz, 2H).

Process 2

Ozone gas was bubbled through a solution of 5.09 g (15 mmol) of compound (XXIII-1) in 300 ml of dichloromethane for 15 h at −78° C. To this solution was added 22 ml (20×15 mmol) of methylsulfide, and the reaction mixture was allowed to warm to room temperature gradually over 80 min and concentrated in vacuo to give 6.03 g aldehyde derivative (XXIV-1). IR(CHCl$_3$, ν max cm$^{-1}$) : 3322, 1710, 1351, 1170. NMR(CDCl$_3$, δ ppm) : 0.85(d, J=6.9 Hz, 3H), 1.00(d, J=6.9 Hz, 3H), 1.22(s, 9H), 2.07(m, 1H), 3.69(dd, J=4.5, 9.9 Hz, 1H), 8.01(s, 4H), 10.08(s, 1H).

Process 3

To a solution of 6.02 g (15 mmol) of compound (XXIV-1) in 60 ml of ethanol and 15 ml of tetrahydrofuran was added 2.72 g (1.05×15 mmol) of benzenesulfonyl hydrazide at room temperature. After being stirred for 2 h, the resulting mixture was concentrated in vacuo. The residue which was obtained by concentration in vacuo was column chromatographed on silica gel and the fractions eluting with chloroform/ethyl acetate=1/4 were collected and recrystallized from ethyl acetate to give 4.44 g of the desired compound (XXV-1). Yield from process 2 60%. mp. 163–164° C.

Elemental analysis C$_{22}$H$_{29}$N$_3$O$_6$S$_2$; Calcd.: C; 53.32 H; 5.90 N; 8.48 S; 12.94; Found: C; 53.15 H; 5.87 N; 8.32 S; 12.82; [α]$_D$ −11.6±1.0(c=0.509 DMSO 23.5° C.); IR(KBr, ν max cm$^{-1}$): 3430, 3274, 1711, 1364, 1343, 1172.

NMR(CDCl$_3$ δ ppm): 0.84(d, J=6.9 Hz, 3H), 0.99(d, J=6.6 Hz, 3H), 1.19(s, 9H), 2.00)m, 1H), 3.63(dd, J=4.5, 9.9 Hz, 1H), 5.16(d, J=9.9 Hz, 1H), 7.50–7.68(m, 5H), 7.73(s, 1H), 7.78–7.84(m, 2H), 7.96–8.02(m, 2H), 8.16(brs, 1H).

Process 4

To a solution of 0.14 ml (1.11×1 mmol) of 4—(methylmercapto)aniline and 0.3 ml of conc. hydrochloric acid in 3 ml of aqueous 50% ethanol solution was added a solution of 78.4 mg (1.14×1 mmol) of sodium nitrite in 1 ml of water at 0 to 5° C. of the internal temperature and the reaction mixture was stirred for 15 min at the same temperature. To a solution of 496 mg (1 mmol) of compound (XXV-1) in 5 ml of dry pyridine was added the above reaction mixture over 8 min at −25° C. This reaction mixture was stirred for additional 4 h at −15° C. to rt, poured into water, and extracted with ethyl acetate. The organic layer was washed with 2N HCl, 5% NaHCO$_3$, and water, dried over Na$_2$SO$_4$, and concentrated in vacuo. The residue was column chromatographed on silica gel and the fractions eluting with chloroform/ethyl acetate=1/9 were collected to give 374 mg of the desired compound (XXVI-1). Yield 74%.

Elemental analysis C$_{23}$H$_{29}$N$_5$O$_4$S$_2$. 0.3H$_2$O; Calcd.: C; 54.27 H; 5.86 N; 13.76 S; 12.60; Found: C; 54.25 H; 5.77 N; 13.87 S; 12.52; IR(KBr, ν max cm$^{-1}$): 3422, 3310, 1705, 1345, 1171. NMR(d$_6$-DMSO, δ ppm): 0.83(d, J=6.9 Hz, 3H), 0.86(d, J=7.2 Hz, 3H), 1.19(s, 9H), 2.00(m, 1H), 2.59(s, 3H), 3.54(dd, J=6.3, 9.6 Hz, 1H), 7.56(d, J=8.7 Hz, 2H), 8.00(d, J=8.6 Hz, 2H), 8.10(d, J=8.7 Hz, 2H), 8.33(d, J=9.6 Hz, 2H), 8.34(d, J=8.7 Hz, 2H).

Process 5

A solution of 353 mg of compound (XXVI-1) in 2.5 ml of dichloromethane and 2.5 ml of trifluoroacetic acid was stirred for 3 h at room temperature. The reaction mixture was concentrated in vacuo and the resulting residue was washed with ethyl ether to give 308 mg of compound (Ia-5-1). Yield 98%. mp. 194–195° C. IR(KBr, ν max cm$^{-1}$): 1720, 1343, 1166.

Elemental analysis C$_{19}$H$_{21}$N$_5$O$_4$S$_2$.1.1H$_2$O; Calcd.: C; 48.83 H; 5.00 N; 14.99 S; 13.72; Found: C; 49.13 H; 5.25 N; 14.55 S; 13.34.

Example 210–251

The compounds which were shown in Tables 37 to 43 were synthesized in a manner similar to those described in Example 209.

TABLE 37

(Ib)

R$^{18}$SO$_2$NH—*C(R$^1$)(H)—CONHOH

| Example No. | R$^1$ | R$^{18}$ |
|---|---|---|
| 210 | indol-3-yl-CH$_2$— | phenyl-N(tetrazol)-phenyl |
| 211 | benzyl-CH$_2$— | phenyl-N(tetrazol)-phenyl |

| Example No. | * | mp (decomp.) (° C.) | IR (ν cm$^{-1}$) (KBr) | $^1$H-NMR(δ ppm) d$_6$-DMSO |
|---|---|---|---|---|
| 210 | R | — | — | — |
| 211 | R | 194–195 | 3700–2200(br), 3278, 1634, 1337, 1160 | 2.65(dd, J=9.3, 13.1Hz, 1H), 2.82(dd, J=5.8, 13.1Hz, 1H), 3.86(dt, J=5.8, 9.3Hz, 1H), 7.72(A$_2$B$_2$q, J=8.1Hz, 2H), 8.19(A$_2$B$_2$q, J=8.1Hz, 2H), 8.49(d, J=9.3Hz, 1H), 8.88(s, 1H), 10.69(s, 1H) |

TABLE 38

(Ia)

$$R^{18}SO_2NH-\overset{R^1}{\underset{*}{C}}H-COOH$$

| Example No. | R[1] | R[18] |
|---|---|---|
| 210 | 1H-indol-3-yl-CH$_2$— | 2-phenyl-5-(4-phenyl)tetrazole |
| 211 | 1H-indol-3-yl-CH$_2$— | 2-phenyl-5-(4-phenyl)tetrazole |

| Example No. | * | mp (decomp.) (° C.) | IR (ν cm$^{-1}$) (KBr) | $^1$H-NMR(δ ppm) d$_6$-DMSO |
|---|---|---|---|---|
| 210 | R | — | — | — |
| 211 | R | 215–216 | 2400–3700br, 3422, 3337, 1733, 1698, 1347, 1170 | 2.75(dd, J=9.3, 13.7Hz, 1H), 2.99 (dd, J=5.3, 13.7Hz, 1H), 3.96(dt, J= 5.3, 9.3Hz, 1H), 8.53(d, J=9.3Hz, 1H) |

TABLE 39

(Ia)

$$R^{18}SO_2NH-\overset{R^1}{\underset{*}{C}}H-COOH$$

| Example No. | R[1] | R[18] |
|---|---|---|
| 212 | 1-methyl-1H-indol-3-yl-CH$_2$— | 2-phenyl-5-(4-phenyl)tetrazole |
| 213 | 5-fluoro-1H-indol-3-yl-CH$_2$— | 2-phenyl-5-(4-phenyl)tetrazole |
| 214 | (CH$_3$)$_2$CHCH$_2$— | 2-phenyl-5-(4-phenyl)tetrazole |
| 215 | (CH$_3$)$_2$CH— | 2-phenyl-5-(4-phenyl)tetrazole |

TABLE 39-continued (Ia)

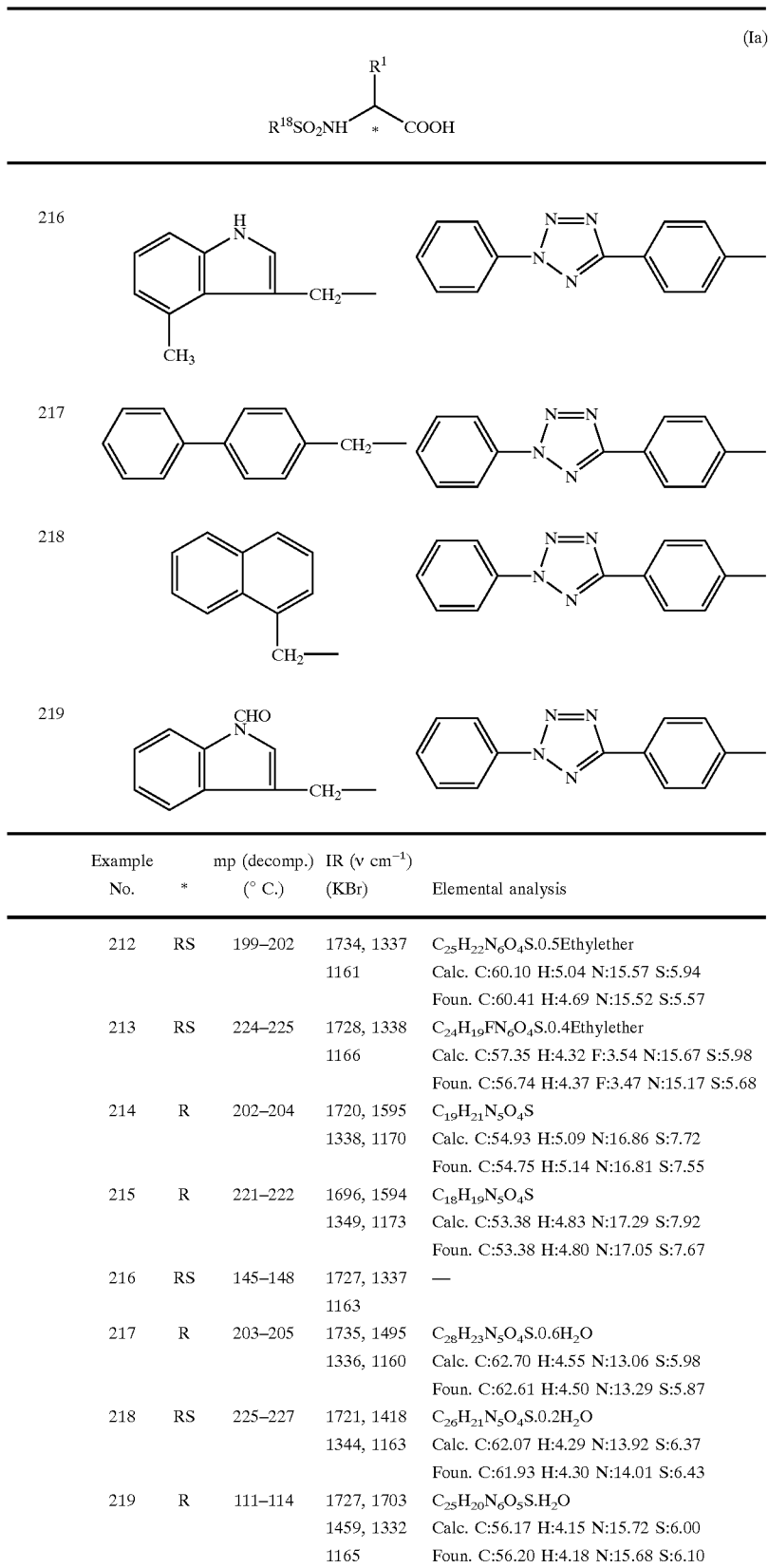

| Example No. | * | mp (decomp.) (° C.) | IR (ν cm$^{-1}$) (KBr) | Elemental analysis |
|---|---|---|---|---|
| 212 | RS | 199–202 | 1734, 1337 1161 | $C_{25}H_{22}N_6O_4S \cdot 0.5$Ethylether<br>Calc. C:60.10 H:5.04 N:15.57 S:5.94<br>Foun. C:60.41 H:4.69 N:15.52 S:5.57 |
| 213 | RS | 224–225 | 1728, 1338 1166 | $C_{24}H_{19}FN_6O_4S \cdot 0.4$Ethylether<br>Calc. C:57.35 H:4.32 F:3.54 N:15.67 S:5.98<br>Foun. C:56.74 H:4.37 F:3.47 N:15.17 S:5.68 |
| 214 | R | 202–204 | 1720, 1595 1338, 1170 | $C_{19}H_{21}N_5O_4S$<br>Calc. C:54.93 H:5.09 N:16.86 S:7.72<br>Foun. C:54.75 H:5.14 N:16.81 S:7.55 |
| 215 | R | 221–222 | 1696, 1594 1349, 1173 | $C_{18}H_{19}N_5O_4S$<br>Calc. C:53.38 H:4.83 N:17.29 S:7.92<br>Foun. C:53.38 H:4.80 N:17.05 S:7.67 |
| 216 | RS | 145–148 | 1727, 1337 1163 | — |
| 217 | R | 203–205 | 1735, 1495 1336, 1160 | $C_{28}H_{23}N_5O_4S \cdot 0.6H_2O$<br>Calc. C:62.70 H:4.55 N:13.06 S:5.98<br>Foun. C:62.61 H:4.50 N:13.29 S:5.87 |
| 218 | RS | 225–227 | 1721, 1418 1344, 1163 | $C_{26}H_{21}N_5O_4S \cdot 0.2H_2O$<br>Calc. C:62.07 H:4.29 N:13.92 S:6.37<br>Foun. C:61.93 H:4.30 N:14.01 S:6.43 |
| 219 | R | 111–114 | 1727, 1703 1459, 1332 1165 | $C_{25}H_{20}N_6O_5S \cdot H_2O$<br>Calc. C:56.17 H:4.15 N:15.72 S:6.00<br>Foun. C:56.20 H:4.18 N:15.68 S:6.10 |

TABLE 40

(Ia)

R¹⁸SO₂NH—*CH(R¹)—COOH

| Example No. | R¹ | R¹⁸ |
|---|---|---|
| 220 | (1H-indol-3-yl)-CH₂— | 4-methoxyphenyl-N(tetrazole)-N—C₆H₄—(4-methyl) |
| 221 | CH₃CH₂(CH₃)CH— | phenyl-N(tetrazole)-N—C₆H₄—(4-methyl) |
| 222 | CH₃CH₂(CH₃)CH— | 4-methoxyphenyl-N(tetrazole)-N—C₆H₄—(4-methyl) |
| 223 | (CH₃)₂CH— | 4-hydroxyphenyl-N(tetrazole)-N—C₆H₄—(4-methyl) |
| 224 | (CH₃)₂CH— | 4-methoxyphenyl-N(tetrazole)-N—C₆H₄—(4-methyl) |
| 225 | (CH₃)₂CH— | 4-bromophenyl-N(tetrazole)-N—C₆H₄—(4-methyl) |
| 226 | (CH₃)₃C— | 4-methoxyphenyl-N(tetrazole)-N—C₆H₄—(4-methyl) |
| 227 | (1H-indol-3-yl)-CH₂— | 4-fluorophenyl-N(tetrazole)-N—C₆H₄—(4-methyl) |

| Example No. | * | mp (decomp.) (° C.) | IR (ν cm⁻¹) (KBr) | Elemental analysis |
|---|---|---|---|---|
| 220 | R | 195–196 | 1749, 1719 1331, 1165 | $C_{25}H_{22}N_6O_5S$<br>Calc. C:57.91 H:4.28 N:16.21 S:6.18<br>Foun. C:57.77 H:4.29 N:16.01 S:6.37 |
| 221 | R | 205–207 | 1730, 1693 1349, 1173 | $C_{19}H_{21}N_5O_4S$<br>Calc. C:54.93 H:5.09 N:16.86 S:7.72<br>Foun. C:54.71 H:5.09 N:16.70 S:7.56 |
| 222 | R | 204–207 | 1729, 1693 1337, 1170 | $C_{20}H_{23}N_5O_5S \cdot 0.4H_2O$<br>Calc. C:53.06 H:5.30 N:15.47 S:7.08<br>Foun. C:53.13 H:5.13 N:15.12 S:7.14 |
| 223 | R | 190 decomp. | 1718, 1601 1385, 1162 | — |
| 224 | R | 195–197 | 1719, 1304 1162 | $C_{20}H_{23}N_5O_5S \cdot 0.4H_2O$<br>Calc. C:53.06 H:5.30 N:15.47 S:7.08<br>Foun. C:53.13 H:5.13 N:15.12 S:7.14 |
| 225 | R | 227–228 | 1696, 1348 1171 | $C_{18}H_{18}BrN_5O_4S \cdot 0.8H_2O$<br>Calc. C:43.70 H:3.99 Br:16.15 N:14.16 S:6.48<br>Foun. C:43.93 H:3.85 Br:15.92 N:13.87 S:6.47 |
| 226 | R | 204–207 | 1698, 1344 1168 | — |

TABLE 40-continued $$R^{18}SO_2NH-\overset{R^1}{\underset{*}{C}H}-COOH \quad (Ia)$$

| | | | | |
|---|---|---|---|---|
| 227 | R | 203–205 | 1757, 1738 1331, 1163 | — |

TABLE 41

$$R^{18}SO_2NH-\overset{R^1}{\underset{*}{C}H}-COOH \quad (Ia)$$

| Example No. | $R^1$ | $R^{18}$ |
|---|---|---|
| 228 | phenyl-CH$_2$— | Br-phenyl-(tetrazole)-phenyl- |
| 229 | phenyl-CH$_2$— | F$_3$C-phenyl-(tetrazole)-phenyl- |
| 230 | phenyl-CH$_2$— | O$_2$N-phenyl-(tetrazole)-phenyl- |
| 231 | phenyl-CH$_2$— | F-phenyl-(tetrazole)-phenyl- |
| 232 | phenyl-CH$_2$— | Cl-phenyl-(tetrazole)-phenyl- |
| 233 | phenyl-CH$_2$— | H$_3$C-phenyl-(tetrazole)-phenyl- |
| 234 | phenyl-CH$_2$— | H$_3$CO-phenyl-(tetrazole)-phenyl- |
| 235 | phenyl-CH$_2$— | NC-phenyl-(tetrazole)-phenyl- |

| Example No. | * | mp (decomp.) (° C.) | IR (ν cm$^{-1}$) (KBr) | Elemental analysis |
|---|---|---|---|---|
| 228 | R | 197–199 | 1744, 1325 1154 | — |
| 229 | R | 197–198 | 1738, 1707 1328, 1169 | $C_{23}H_{18}F_3N_5O_4S$ Calc. C:53.38 H:3.51 F:11.01 N:13.53 S:6.20 Foun. C:53.11 H:3.55 F:10.89 N:13.66 S:6.31 |

TABLE 41-continued $$\text{R}^{18}\text{SO}_2\text{NH}-\overset{\text{R}^1}{\underset{*}{\text{C}}}\text{H}-\text{COOH} \quad (\text{Ia})$$

| | | | | |
|---|---|---|---|---|
| 230 | R | 190–191 | 1730, 1597 | $C_{22}H_{18}N_6O_6S\cdot0.4H_2O$ |
| | | | 1345, 1161 | Calc. C:52.67 H:3.78 N:16.73 S:6.39 |
| | | | | Foun. C:52.73 H:3.92 N:16.53 S:6.55 |
| 231 | R | 205–207 | 1730, 1509 | $C_{22}H_{18}FN_5O_4S\cdot0.2H_2O$ |
| | | | 1236, 1165 | Calc. C:56.09 H:3.94 F:4.03 N:14.87 S:6.81 |
| | | | | Foun. C:56.10 H:4.09 F:4.12 N:14.84 S:7.08 |
| 232 | R | 204–206 | 1730, 1493 | $C_{22}H_{18}ClN_5O_4S\cdot0.6H_2O$ |
| | | | 1346, 1164 | Calc. C:53.41 H:3.91 Cl:7.17 N:14.16 S:6.48 |
| | | | | Foun. C:53.33 H:3.90 Cl:7.22 N:14.19 S:6.68 |
| 233 | R | 226–227 | 1732, 1697 | $C_{23}H_{21}N_5O_4S\cdot1.2H_2O$ |
| | | | 1509, 1373 | Calc. C:56.94 H:4.86 N:14.44 S:6.61 |
| | | | 1345, 1170 | Foun. C:56.88 H:4.49 N:14.31 S:6.72 |
| 234 | R | 214–216 | 1732, 1697 | $C_{23}H_{21}N_5O_5S\cdot1.7H_2O$ |
| | | | 1345, 1168 | Calc. C:54.15 H:4.82 N:13.73 S:6.29 |
| | | | | Foun. C:54.05 H:4.35 N:13.60 S:6.77 |
| 235 | R | 190–192 | 1731, 1605 | $C_{23}H_{18}N_6O_4S\cdot0.8H_2O$ |
| | | | 1336, 1160 | Calc. C:56.50 H:4.04 N:17.19 S:6.56 |
| | | | | Foun. C:56.52 H:4.16 N:17.00 S:8.52 |

TABLE 42

$$\text{R}^{18}\text{SO}_2\text{NH}-\overset{\text{R}^1}{\underset{*}{\text{C}}}\text{H}-\text{COOH} \quad (\text{Ia})$$

| Example No. | R¹ | R¹⁸ |
|---|---|---|
| 236 | benzyl (Ph-CH₂–) | 4-(5-(4-tert-butylphenyl)tetrazol-2-yl)phenyl |
| 237 | benzyl (Ph-CH₂–) | 4-(5-(4-cyclohexylphenyl)tetrazol-2-yl)phenyl |
| 238 | benzyl (Ph-CH₂–) | 4-(5-(4-phenoxyphenyl)tetrazol-2-yl)phenyl |
| 239 | benzyl (Ph-CH₂–) | 4-(5-(4-hydroxyphenyl)tetrazol-2-yl)phenyl |
| 240 | (1H-indol-3-yl)methyl | 4-(5-(4-bromophenyl)tetrazol-2-yl)phenyl |
| 241 | (1H-indol-3-yl)methyl | 4-(5-(4-methylphenyl)tetrazol-2-yl)phenyl |

TABLE 42-continued (Ia)

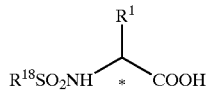

| 242 | (CH$_3$)$_2$CH— | 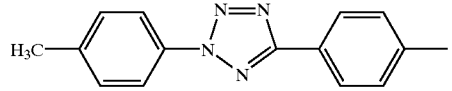 |
| 243 | (CH$_3$)$_2$CH— | 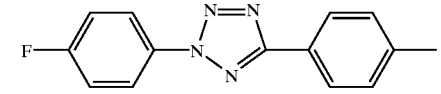 |

| Example No. | * | mp (decomp.) (° C.) | IR (ν cm$^{-1}$) (KBr) | Elemental analysis |
|---|---|---|---|---|
| 236 | R | 224–226 | 1738, 1328 1314, 1149 | C$_{26}$H$_{27}$N$_5$O$_4$S<br>Calc. C:61.77 H:5.38 N:13.85 S:6.34<br>Foun. C:61.59 H:5.45 N:13.89 S:6.27 |
| 237 | R | 225–227 | 1739, 1512 1329, 1178 | C$_{28}$H$_{29}$N$_5$O$_4$S.0.3H$_2$O<br>Calc. C:62.62 H:5.56 N:13.04 S:5.97<br>Foun. C:62.46 H:5.52 N:13.43 S:6.28 |
| 238 | R | 182–184 | 1587, 1506 1242, 1159 | — |
| 239 | R | 226–228 | 1713, 1514 1341, 1159 | — |
| 240 | R | 205–207 | 1744, 1716 1490, 1327 1159 | C$_{24}$H$_{19}$BrN$_6$O$_4$S.1.7H$_2$O<br>Calc. C:48.20 H:3.78 Br:13.36 N:14.05 S:5.36<br>Foun. C:48.27 H:3.75 Br:13.16 N:14.11 S:5.38 |
| 241 | R | 199–201 | 1718, 1685 1334, 1170 | C$_{25}$H$_{22}$N$_6$O$_4$S.0.8H$_2$O<br>Calc. C:58.49 H:4.56 N:16.37 S:6.25<br>Foun. C:58.52 H:4.69 N:16.71 S:5.90 |
| 242 | R | 206–207 | 1716, 1346 1165 | C$_{19}$H$_{21}$N$_5$O$_4$S.0.8H$_2$O<br>Calc. C:53.09 H:5.30 N:16.29 S:7.46<br>Foun. C:53.20 H:5.14 N:16.06 S:7.70 |
| 243 | R | 208–209 | 1746, 1726 1715, 1334 1159 | C$_{18}$H$_{18}$FN$_5$O$_4$S.0.2H$_2$O<br>Calc. C:51.11 H:4.38 F:4.49 N:16.55 S:7.58<br>Foun. C:50.90 H:4.37 F:4.89 N:16.28 S:7.46 |

TABLE 43

(Ia)

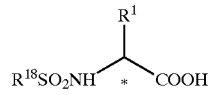

| Example No. | R$^1$ | R$^{18}$ |
|---|---|---|
| 244 | (CH$_3$)$_2$CH— | 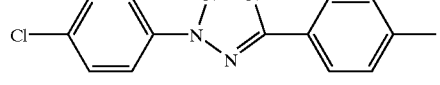 |
| 245 | (CH$_3$)$_2$CH— | 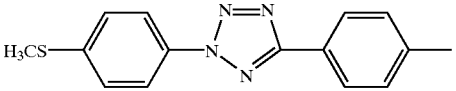 |
| 246 | 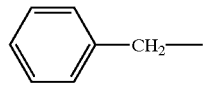 | 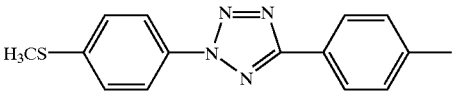 |

TABLE 43-continued
(Ia)
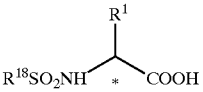
| 247 | 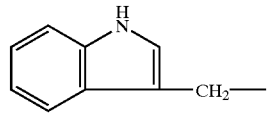 | 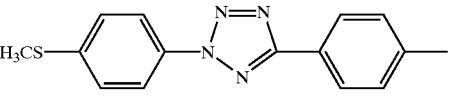 |
| --- | --- | --- |
| 248 | 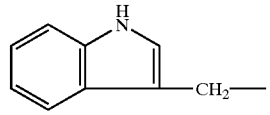 | 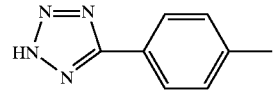 |
| 249 | 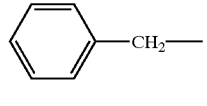 | 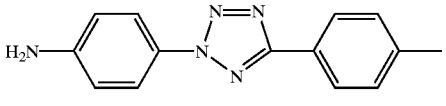 |
| 250 | 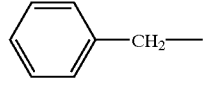 | 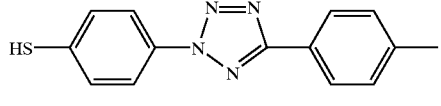 |
| 251 | 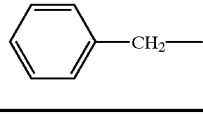 | 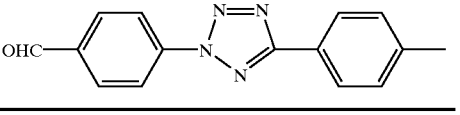 |
| Example No. | * | mp (decomp.) (° C.) | IR (ν cm$^{-1}$) (KBr) | Elemental analysis |
| --- | --- | --- | --- | --- |
| 244 | R | 223–225 | 1696, 1348 1171 | — |
| 245 | R | 194–195 | 1720, 1343 1166 | $C_{19}H_{21}N_5O_4S_2 \cdot 1.1H_2O$ Calc. C:48.83 H:5.00 N:14.99 S:13.72 Foun. C:49.13 H:5.25 N:14.55 S:13.34 |
| 246 | R | 222–224 | 1753, 1497 1325, 1165 | $C_{23}H_{21}N_5O_4S_2 \cdot 0.2H_2O$ Calc. C:55.34 H:4.32 N:14.03 S:12.85 Foun. C:55.37 H:4.35 N:14.00 S:12.86 |
| 247 | R | 213–216 | 1718, 1677 1495, 1333 1170 | $C_{25}H_{22}N_6O_4S_2 \cdot 1.1H_2O$ Calc. C:54.16 H:4.40 N:15.16 S:11.57 Foun. C:54.20 H:4.66 N:15.09 S:11.62 |
| 248 | R | >220 | 1698, 1430 1327, 1163 | $C_{18}H_{16}N_6O_4S \cdot 0.4H_2O$ Calc. C:51.52 H:4.04 N:20.03 S:7.64 Foun. C:51.34 H:3.96 N:19.76 S:8.02 |
| 249 | R | — | — | — |
| 250 | R | — | — | — |
| 251 | R | — | — | — |

Example 252–266

The compounds which were shown in Tables 44 to 45 were synthesized in a manner similar to those described in Example 157.

TABLE 44

(I)

R¹⁸SO₂N(R¹⁹)—C*(R¹)(R²⁰)

| Example No. | R¹ | R¹⁸ | R¹⁹ |
|---|---|---|---|
| 252 | (CH₃)₂CH— | 4-phenoxyphenyl | —CH₃ |
| 253 | (CH₃)₂CH— | 4-phenoxyphenyl | —CH₃ |
| 254 | (CH₃)₂CH— | 4-phenoxyphenyl | —CH₂-phenyl |
| 255 | (CH₃)₂CH— | 4-phenoxyphenyl | —(CH₂)₄NH₂ |
| 256 | (CH₃)₂CH— | 4-(2-phenyltetrazol-5-yl)phenyl | —CH₃ |
| 257 | (CH₃)₂CHCH₂— | 4-(2-phenyltetrazol-5-yl)phenyl | —CH₃ |
| 258 | benzyl-phenyl— | 4-(2-(4-benzylphenyl)tetrazol-5-yl)phenyl | —CH₂-phenyl |
| 259 | (CH₃)₂CH— | 5-(4-methylthiophenyl)thiophen-2-yl | —CH₃ |

| Example No. | R²⁰ | * | mp (decomp.) (° C.) | IR (ν cm⁻¹) (KBr) | ¹H-NMR(δ ppm) d₆-DMSO |
|---|---|---|---|---|---|
| 252 | —COOH | R | — | 1715, 1583 1340, 1151 | 0.96(d, J=6.6Hz, 3H) 1.01(d, 6.8Hz, 3H) 2.87(s, 3H) |

TABLE 44-continued
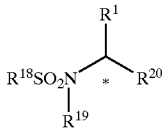
| 253 | —CONHOH | R | 110–111 | 3323, 1678 1328, 1150 | 4.17(d, J=10.4Hz, 1H) 0.71(d, J=6.6Hz, 3H) 0.88(d, 6.4Hz, 3H) 2.88(s, 3H) |
| --- | --- | --- | --- | --- | --- |
| 254 | —CONHOH | R | 148–150 | 3344, 1684 1323, 1149 | 3.48(d, J=10.8Hz, 1H) 0.55(d, J=6.8Hz, 3H) 0.82(d, 6.6Hz, 3H) 3.74(s, 3H) |
| 255 | —COOH | R | — | 3700–2200br 1681, 1319 1212 | 0.91(d, J=5.6Hz, 6H) 1.52–1.69(m, 4H) 3.84(d, J=10.4Hz, 1H) |
| 256 | —COOH | R | 206–207 | 3300–2400br 1711, 1336 1185 | 0.95(d, J=6.6Hz, 3H) 0.97(d, 6.8Hz, 3H) 2.89(s, 3H) 4.20(d, J=10.6Hz, 1H) |
| 257 | —COOH | R | 132–132.5 | 3300–2400br 1719, 1340 1153 | 0.92(d, J=6.6Hz, 3H) 0.97(d, 6.6Hz, 3H) 2.84(s, 3H) 4.73(t, J=7.4Hz, 1H) |
| 258 | —COOH | R | — | 3640–2400br 1736, 1717 1694, 1346 1162 | 2.78(d.d, J=13.8, 7.2Hz, 1H) 3.14(d.d, J=14.8, 7.4Hz, 1H) 4.43(d, J=16.4Hz, 1H) 4.68(d, J=16.4Hz, 1H) |
| 259 | —COOH | R | 141–144 | 3284br, 1745 1714, 1323 1131 | 0.96(d, J=6.4Hz, 3H) 0.97(d, J=6.4Hz, 3H) 2.52(s, 3H), 2.93(s, 3H) |

TABLE 45

$$R^{18}SO_2N\overset{R^1}{\underset{R^{19}}{\overset{|}{C}H}}\overset{*}{-}R^{20} \quad (I)$$

| Example No. | R¹ | R¹⁸ | R¹⁹ | R²⁰ | * | mp (decomp.) (°C.) | IR(ν cm⁻¹) (KBr) | ¹H-NMR(δ ppm) d₆-DMSO |
|---|---|---|---|---|---|---|---|---|
| 260 | (CH₃)₂CH— | H₃CS—⌬—⌬(S-methyl) | —CH₂—⌬ | —COOH | R | — | 3600–2400br 1718, 1344 1151 | 0.72(d, J=6.4Hz, 3H)0.85(d, J=6.4Hz, 3H)2.47(s, 3), 4.15(d, J=10.2Hz, 1H)4.51(d, J=15.5 Hz, 1H)4.73(d, J=15.5Hz, 1H) |
| 261 | —CH₂—⌬ H₃CS—⌬ | H₃CS—⌬—C(O)NH—⌬(Me) | —CH₃ | —COOH | R | — | 3600–2400br 1719, 1655 1592, 1320 1154 | 2.54(s, 3H), 2.78(s, 3H) 2.85(d.d, J=14.0, 9.4Hz, 1H) 3.16(d.d, J=14.0, 6.0Hz, 1H) 4.76(d.d, J=10.0, 5.8Hz, 1H) |
| 262 | —CH₂—⌬ H₃CS—⌬ | H₃CS—⌬—C(O)NH—⌬(Me) | —CH₂—⌬ | —COOH | R | — | — | — |
| 263 | —CH₂—⌬ H₃CO—⌬ | H₃CO—⌬—C≡C—⌬(Me) (thiophene) | —(CH₂)₄NH₂ | —COOH | R | — | — | — |
| 264 | —CH₂—⌬ H₃CO—⌬ | H₃CO—⌬—C≡C—⌬(Me) | —CH₃ | —COOH | R | — | — | — |
| 265 | —CH₂—⌬ H₃CO—⌬ | H₃CO—⌬—C≡C—⌬(Me) | —CH₂—⌬ | —COOH | R | — | — | — |
| 266 | —CH₂—⌬ H₃CO—⌬ | H₃CO—⌬—C≡C—⌬(Me) | —(CH₂)₄NH₂ | —COOH | R | — | — | — |

Example 267

The compounds which were shown in Tables 46 were synthesized in a manner similar to those described in Example 92.

TABLE 46

$$R^{18}\text{-SO}_2\text{HN}-\overset{R^1}{\underset{*}{\text{C}}}-R^{20} \quad (I)$$

| Example No. | $R^1$ | $R^{18}$ | $R^{20}$ | * | mp (decomp.) (° C.) | IR(ν cm$^{-1}$) (KBr) | $^1$H-NMR(δ ppm) $d_6$-DMSO |
|---|---|---|---|---|---|---|---|
| 267 | Ph-CH$_2$- | -C$_6$H$_4$-C≡C-C$_6$H$_4$- | —CONHOH | R | 156–158 | 3700–2400br, 3267, 2217, 1671, 1321, 1161 | 2.62(dd, J=8.4, 13.5Hz, 1H), 2.80 (dd, J=6.0, 13.5Hz, 1H), 3.82 (ddd, J=6.0, 8.4, 8.7Hz, 1H), 8.38 (d, J=8.7Hz, 1H) |
| 267 | Ph-CH$_2$- | -C$_6$H$_4$-C≡C-C$_6$H$_4$- | —COOH | R | 176–178 | 2200–3700br, 3430, 3292, 1728, 1324, 1162 | 2.73(dd, J=9.3, 13.6Hz, 1H), 2.96 (dd, J=5.4, 13.5Hz, 1H), 3.92 (dt, J=5.4, 9.3Hz, 1H), 8.42(d, J=9.3Hz, 1H) |

Test examples on the compounds of the present invention are described below. The test compounds are the ones described in the Examples and Tables. Test example (1) Isolation and Purification of MMP-9 (92 kDa, Gelatinase B)

Type IV collagenase (MMP-9) was purified according to the methods descrived in the following literature. Scott M. Wilhelm et al., J. Biol. Chem., 264, 17213–17221, (1989), SV40-transformed Human Lung Fibroblasts Secrete a 92-kDa Type IV Collagenase Which Is Identical to That Secreted by Normal Human Macrophages; Yasunori Okada et al., J. Biol. Chem., 267, 21712–21719, (1992), Matrix Metalloproteinase 9 (92-kDa Gelatinase/Type IV Collagenase) from HT 1080 Human Fibrosarcoma Cells; Robin V. Ward et al., Biochem. J., (1991) 278, 179–187, The purification of tissue inhibitor of metalloproteinase-2 from its 72 kDa progelatinase complex.

MMP-9 is secreted from human fibrosarcoma cell line ATCC HT 1080, into its culture medium when it is stimulated with 12-tetradecanoylphorbol-13-acetate (TPA). The production of MMP-9 in this culture was verified by the gelatin zymography as described in the following literature (Hidekazu Tanaka et al., (1993) Biochem. Biophys. Res. Commun., 190, 732–740, Molecular cloning and manifestation of mouse 105-kDa gelatinase cDNA). The condition medium of the stimulated HT 1080 was concentrated and was purified with gelatin-Sepharose 4B, concanavalin A-sepharose, and Sephacryl S-200. The purified pro-MMP-9 (92 kDa, gelatinase B) thus obtained gave a single positive band in the gelatin zymography. Subsequently, activated MMP-9 was obtained by treating the pro-MMP-9 with trypsin.

(2) Assay Methods of Type IV Collagenase Inhibitors

Collagenase assay was performed using the activated MMP-9 described above and the substrate supplied in the type IV collagenase activity kit (YAGAI, inc.), according to the manufacturer's protocol. The following 4 assays are performed per compound (inhibitor).

(A) substrate (type IV collagenase), enzyme (MMP-9), inhibitor (B) substrate (type IV collagenase), inhibitor (C) substrate (type IV collagenase), enzyme (MMP-9)

(D) substrate (type IV collagenase)

According to the manufacturer's protocol, fluorescent intensity was measured and percent inhibition was determined by the following equation.

$$\text{Inhibition (\%)} = \{1-(A-B)/(C-D)\} \times 100$$

IC$_{50}$ is a concentration at which the percent inhibition reaches 50%. The results are shown in Tables 47 to 54.

TABLE 47

| Example No. | Compound No. | IC$_{50}$ (μM) | Compound No. | IC$_{50}$ (μM) |
|---|---|---|---|---|
| 1  | 1a-1-1  | 0.24  | 1b-1-1  | 0.030 |
| 2  | 1a-1-2  | 2.6   | 1b-1-2  | 0.04 |
| 3  | 1a-1-3  | 0.18  | 1b-1-3  | 0.005 |
| 4  | 1a-1-4  | 2.25  |         |        |
| 5  | 1a-1-5  | 0.81  | 1b-1-5  | 0.041 |
| 6  | 1a-1-6  | 0.68  | 1b-1-6  | 0.034 |
| 7  |         |       | 1b-1-7  | 0.028 |
| 8  | 1a-1-8  | 2.0   | 1b-1-8  | 2.0 |
| 9  |         |       | 1b-1-9  | 0.41 |
| 10 |         |       | 1b-1-10 | 2.1 |
| 11 |         |       | 1b-1-11 | 1.7 |
| 12 |         |       | 1b-1-12 | 0.085 |
| 13 |         |       | 1b-1-13 | 0.38 |
| 14 | 1a-1-14 | 3.7   | 1b-1-14 | 0.11 |
| 15 |         |       | 1b-1-15 | 0.027 |
| 16 | 1a-1-16 | 0.520 | 1b-1-16 | 0.0108 |
| 17 | 1a-1-17 | 0.205 | 1b-1-17 | 0.0203 |
| 18 | 1a-1-18 | 0.500 | 1b-1-18 | 0.0282 |
| 20 |         |       | 1b-1-20 | 0.134 |
| 21 | 1a-1-21 | 4.65  | 1b-1-21 | 0.0041 |
| 23 |         |       | 1b-1-23 | 0.073 |
| 24 |         |       | 1b-1-24 | 0.2 |
| 26 |         |       | 1b-1-26 | 1.3 |

TABLE 47-continued

| Example No. | Compound No. | IC$_{50}$ ($\mu$M) | Compound No. | IC$_{50}$ ($\mu$M) |
|---|---|---|---|---|
| 27 | | | 1b-1-27 | 3.0 |
| 30 | 1a-1-30 | 1.16 | 1b-1-30 | 0.213 |
| 31 | | | 1b-1-31 | 0.0129 |

TABLE 48

| Example No. | Compound No. | IC$_{50}$ ($\mu$M) | Compound No. | IC$_{50}$ ($\mu$M) |
|---|---|---|---|---|
| 33 | 1a-1-33 | 0.24 | 1b-1-33 | 0.005 |
| 35 | 1a-1-35 | 2.6 | 1b-1-35 | 0.0216 |
| 38 | 1a-1-38 | 0.018 | | |
| 40 | 1a-1-40 | 0.076 | | |
| 41 | 1a-1-41 | 0.312 | | |
| 42 | 1a-1-42 | 0.0123 | | |
| 43 | 1a-1-43 | 0.625 | | |
| 44 | 1a-1-44 | 1.910 | | |
| 45 | 1a-1-45 | 0.040 | | |
| 46 | 1a-1-46 | 1.12 | | |
| 47 | 1a-1-47 | 0.389 | | |
| 48 | 1a-1-48 | 1.15 | | |
| 49 | 1a-1-49 | 0.249 | | |
| 50 | 1a-1-50 | 0.553 | | |
| 51 | 1a-1-51 | 0.110 | | |
| 52 | 1a-1-52 | 0.329 | | |
| 53 | 1a-1-53 | 1.8 | | |
| 54 | 1a-1-54 | 0.075 | | |
| 55 | 1a-1-55 | 0.0398 | | |
| 60 | 1a-1-60 | 1.31 | 1b-1-60 | 0.0012 |
| 61 | 1a-1-61 | 0.247 | 1b-1-61 | 0.247 |
| 62 | | | 1b-1-62 | 3.50 |
| 63 | 1a-1-63 | 1.05 | 1b-1-63 | 0.00039 |
| 64 | 1a-1-64 | 1.90 | 1b-1-64 | 0.0037 |
| 65 | 1a-1-65 | 0.291 | 1b-1-65 | 0.0035 |

TABLE 49

| Example No. | Compound No. | IC$_{50}$ ($\mu$M) | Compound No. | IC$_{50}$ ($\mu$M) |
|---|---|---|---|---|
| 67 | 1a-1-67 | | 1b-1-67 | 0.0061 |
| 68 | 1a-1-68 | 0.231 | | |
| 80 | 1a-1-80 | 1.91 | | |
| 83 | 1a-1-83 | 1.77 | | |
| 85 | 1a-1-85 | 1.2 | 1b-1-85 | 0.013 |
| 86 | 1a-1-86 | 0.35 | 1b-1-86 | 0.0053 |
| 87 | | | 1b-1-87 | 0.940 |
| 93 | 1a-2-2 | 0.237 | | |
| 94 | 1a-2-3 | 0.0109 | | |
| 95 | 1a-2-4 | 0.0759 | | |
| 96 | 1a-2-5 | 0.123 | | |
| 97 | 1a-2-6 | 0.088 | | |
| 98 | 1a-2-7 | 0.0699 | | |
| 100 | 1a-2-9 | 0.0577 | | |
| 101 | 1a-2-10 | 0.023 | | |
| 102 | 1a-2-11 | 0.0475 | | |
| 103 | 1a-2-12 | 0.0981 | | |
| 104 | 1a-2-13 | 3.28 | | |
| 105 | 1a-2-14 | 2.98 | | |
| 106 | 1a-2-15 | 0.133 | | |
| 107 | 1a-2-16 | 0.325 | | |
| 109 | 1a-2-18 | 1.19 | | |
| 110 | 1a-2-19 | 0.203 | | |
| 111 | 1a-2-20 | 3.41 | | |
| 112 | 1a-2-21 | 3.74 | | |
| 114 | 1a-2-23 | 0.929 | | |

TABLE 50

| Example No. | Compound No. | IC$_{50}$ ($\mu$M) |
|---|---|---|
| 115 | 1a-2-24 | 0.161 |
| 117 | 1a-2-26 | 1.19 |
| 118 | 1a-2-27 | 0.088 |
| 119 | 1a-2-28 | 1.11 |
| 120 | 1a-2-29 | 1.53 |
| 121 | 1a-2-30 | 0.0736 |
| 122 | 1a-2-31 | 0.224 |
| 123 | 1a-2-32 | 0.0234 |
| 124 | 1a-2-33 | 0.0218 |
| 125 | 1a-2-34 | 0.0144 |
| 126 | 1a-2-35 | 0.156 |
| 127 | 1a-2-36 | 0.0243 |
| 128 | 1a-2-37 | 0.0922 |
| 129 | 1a-2-38 | 0.222 |
| 160 | 1a-3-2 | 0.040 |
| 161 | 1a-3-3 | 0.0108 |
| 162 | 1a-3-4 | 0.873 |
| 163 | 1a-3-5 | 0.0126 |
| 164 | 1a-3-6 | 0.0965 |
| 165 | 1a-3-7 | 0.230 |
| 166 | 1a-3-8 | 1.28 |
| 167 | 1a-3-9 | 0.014 |
| 168 | 1a-3-10 | 0.0083 |
| 169 | 1a-3-11 | 0.244 |
| 170 | 1a-3-12 | 2.03 |
| 171 | 1a-3-13 | 0.0395 |

TABLE 51

| Example No. | Compound No. | IC$_{50}$ ($\mu$M) |
|---|---|---|
| 177 | 1a-4-2 | 0.684 |
| 178 | 1a-4-3 | 0.0252 |
| 179 | 1a-4-4 | 2.36 |
| 180 | 1a-4-5 | 0.045 |
| 181 | 1a-4-6 | 0.0539 |
| 182 | 1a-4-7 | 0.0059 |
| 183 | 1a-4-8 | 0.0027 |
| 184 | 1a-4-9 | 0.00325 |
| 185 | 1a-4-10 | 0.0422 |
| 186 | 1a-4-11 | 0.0982 |
| 187 | 1a-4-12 | 0.177 |
| 188 | 1a-4-13 | 0.843 |
| 189 | 1a-4-14 | 0.0375 |
| 190 | 1a-4-15 | 0.0597 |
| 191 | 1a-4-16 | 0.0095 |
| 192 | 1a-4-17 | 0.324 |
| 193 | 1a-4-18 | 0.722 |
| 195 | 1a-4-20 | 1.1 |
| 196 | 1a-4-21 | 0.0573 |
| 197 | 1a-4-22 | 0.0161 |
| 198 | 1a-4-23 | 0.493 |
| 199 | 1a-4-24 | 2.06 |
| 200 | 1a-4-25 | 0.173 |
| 201 | 1a-4-26 | 0.252 |
| 202 | 1a-4-27 | 0.0114 |
| 203 | 1a-4-28 | 0.173 |

TABLE 52

| Example No. | Compound No. | IC$_{50}$ ($\mu$M) | Compound No. | IC$_{50}$ ($\mu$M) |
|---|---|---|---|---|
| 204 | 1a-4-29 | 3.95 | | |
| 207 | 1a-4-30 | 4.44 | | |
| 210 | 1a-5-2 | 0.024 | | |
| 211 | 1a-5-3 | 0.210 | 1b-211 | 0.00565 |
| 212 | 1a-5-4 | 0.393 | | |
| 213 | 1a-5-5 | 0.128 | | |
| 214 | 1a-5-6 | 0.832 | | |
| 215 | 1a-5-7 | 0.110 | | |
| 216 | 1a-5-8 | 0.107 | | |
| 218 | 1a-5-10 | 0.744 | | |

TABLE 52-continued

| Example No. | Compound No. | IC$_{50}$ ($\mu$M) | Compound No. | IC$_{50}$ ($\mu$M) |
|---|---|---|---|---|
| 219 | 1a-5-11 | 0.574 | | |
| 220 | 1a-5-12 | 0.0167 | | |
| 221 | 1a-5-13 | 0.316 | | |
| 222 | 1a-5-14 | 0.078 | | |
| 223 | 1a-5-15 | 0.349 | | |
| 224 | 1a-1-16 | 0.0101 | | |
| 225 | 1a-5-17 | 0.0122 | | |
| 226 | 1a-5-18 | 0.166 | | |
| 227 | 1a-5-19 | 0.0198 | | |
| 228 | 1a-5-20 | 0.106 | | |
| 229 | 1a-5-21 | 0.215 | | |
| 230 | 1a-5-22 | 0.281 | | |
| 231 | 1a-5-23 | 0.197 | | |
| 232 | 1a-5-24 | 0.144 | | |
| 233 | 1a-5-25 | 0.0864 | | |
| 234 | 1a-5-26 | 0.153 | | |

TABLE 53

| Example No. | Compound No. | IC$_{50}$ ($\mu$M) | Compound No. | IC$_{50}$ ($\mu$M) |
|---|---|---|---|---|
| 235 | 1a-5-27 | 0.265 | | |
| 236 | 1a-5-28 | 0.304 | | |
| 237 | 1a-5-29 | 1.32 | | |
| 238 | 1a-5-30 | 2.85 | | |
| 239 | 1a-5-31 | 0.243 | | |
| 240 | 1a-5-32 | 0.0041 | | |
| 241 | 1a-5-33 | 0.0131 | | |
| 242 | 1a-5-34 | 0.0239 | | |
| 243 | 1a-5-35 | 0.0529 | | |
| 244 | 1a-5-36 | 0.0165 | | |
| 245 | 1a-5-37 | 0.0059 | | |
| 246 | 1a-5-38 | 0.0108 | | |
| 247 | 1a-5-39 | 0.0035 | | |
| 267 | 1a-2-66 | 1.5 | 1b-2-66 | 0.011 |

TABLE 54

| Example No. | Compound No. | IC$_{50}$ ($\mu$M) |
|---|---|---|
| 252 | 1-252 | 0.24 |
| 253 | 1-253 | 0.000039 |
| 254 | 1-254 | 0.00063 |
| 255 | 1-255 | 0.529 |
| 256 | 1-256 | 0.601 |
| 257 | 1-257 | 0.776 |
| 258 | 1-258 | 0.908 |
| 259 | 1-259 | 0.130 |
| 260 | 1-260 | 0.159 |
| 261 | 1-260 | 0.182 |

The compound of the present invention showed strong activity for inhibiting type IV collagenase.

INDUSTRIAL APPLICABILITY

It is considered that the compound of the present invention is useful to prevent or treat osteoarthritis, rheumatoid arthritis, corneal ulceration, periodontal disease, metastasis and invasion of tumor, advanced virus infection (e.g., HIV), arteriosclerosis obliterans, arteriosclerotic aneurysm, atherosclerosis, restenosis, sepsis, septic shock, coronary thrombosis, aberrant angiogenesis, scleritis, multiple sclerosis, open angle glaucoma, retinopathies, proliferative retinopathy, neovascular glaucoma, pterygium, keratitis, epidermolysis bullosa, psoriasis, diabetes, nephritis, neurodegenerative disease, gingivitis, tumor growth, tumor angiogenesis, ocular tumor, angiofibroma, hemangioma, fever, hemorrhage, coagulation, cachexia, anorexia, acute infection, shock, autoimmune disease, malaria, Crohn disease, meningitis, and gastric ulcer, because the compound of the present invention has strong inhibitory activity against metalloproteinase, especially MMP.

What is claimed is:

1. A composition for inhibiting metalloproteinase which comprises a compound of formula I:

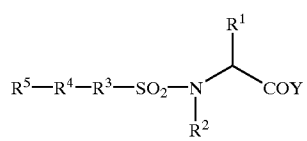

I wherein R$^1$ is optionally substituted heteroarylalkyl;

R$^2$ is hydrogen atom or optionally substituted lower alkyl;

R$^3$ is optionally substituted arylene;

R$^4$ is a bond, —(CH$_2$)m—, —CH═CH— or —C≡C—;

R$^5$ is optionally substituted aryl;

Y is —NHOH or —OH;

and m is 1 or 2;

provided R$^2$ is hydrogen atom when Y is —NHOH, with the proviso that R$^5$ and R$^3$ together do not form a biphenyl group, and its optically active substance, pharmaceutically acceptable salt, or hydrate thereof.

2. A composition for inhibiting metalloproteinase which comprises a compound of formula I:

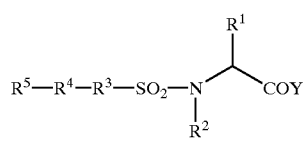

I wherein R$^1$ is optionally substituted heteroarylalkyl;

R$^2$ is hydrogen atom or optionally substituted lower alkyl;

R$^3$ is optionally substituted arylene;

R$^4$ is a bond, —(CH$_2$)m—, —CH═CH— or —C≡C—;

R$^5$ is optionally substituted aryl;

Y is —NHOH or —OH;

and m is 1 or 2;

provided R$^2$ is hydrogen atom when Y is —NHOH,

R$^5$ is aryl substituted by lower alkyl or optionally substituted aryl when R$^4$ is a bond, with the proviso that R$^5$ and R$^3$ together do not form a biphenyl group, and its optically active substance, pharmaceutically acceptable salt, or hydrate thereof.

3. A compound of the formula I:

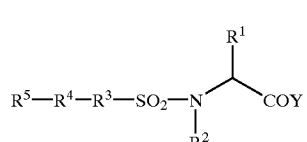

I wherein R$^1$ is optionally substituted heteroarylalkyl;

R$^2$ is hydrogen atom or optionally substituted lower alkyl;

R$^3$ is optionally substituted arylene;

$R^4$ is a bond, —(CH$_2$)m—, —CH=CH— or —C≡C—;
$R^5$ is optionally substituted aryl;
Y is —NHOH or —OH;
and m is 1 or 2;
provided $R^2$ is hydrogen atom when Y is —NHOH,
$R^5$ is aryl substituted with lower alkyl or optionally substituted aryl when $R^4$ is a bond,
and $R^3$ is not 1,2-phenylene,
and its optically active substance, pharmaceutically acceptable salt, or hydrate thereof.

4. A compound of formula II:

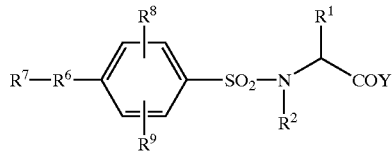

wherein $R^6$ is —CH=CH— or —C≡C—;
$R^7$ is optionally substituted aryl;
$R^8$ and $R^9$ are each independently hydrogen atom, lower alkoxy, or nitro;
$R^1$ is optionally substituted heteroarylalkyl;[,]
$R^2$ is hydrogen atom or optionally substituted lower alkyl;
Y is —NHOH or —OH; and
its optically active substance, pharmaceutically acceptable salt, or hydrate thereof.

5. A compound of formula III:

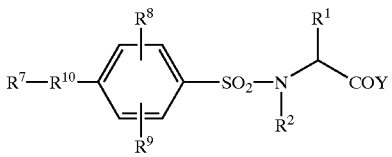

wherein $R^{10}$ is —(CH$_2$)m—;
m is 1 or 2;
$R^1$ is optionally substituted heteroarylalkyl;
$R^2$ is hydrogen atom or optionally substituted lower alkyl;
$R^7$ is optionally substituted aryl;
$R^8$ and $R^9$ are each independently hydrogen atom, lower alkoxy, or nitro;
Y is —NHOH or —OH; and
its optically active substance, pharmaceutically acceptable salt, or hydrate thereof.

6. A compound of formula V:

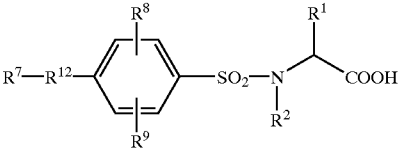

wherein $R^{12}$ is —CH=CH— or —C≡C—;
$R^1$ is optionally substituted heteroarylalkyl;
$R^1$ is hydrogen atom or optionally substituted lower alkyl;
$R^7$ is optionally substituted aryl;

$R^8$ and $R^9$ are each independently hydrogen atom, lower alkoxy or nitro; and
its optically active substance, pharmaceutically acceptable salt, or hydrate thereof.

7. A compound of formula X:

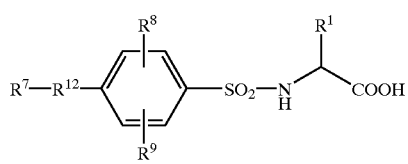

wherein $R^{12}$ is —CH=CH— or —C≡C—;
$R^1$ is optionally substituted heteroarylalkyl;
$R^7$ is optionally substituted aryl;
$R^8$ and $R^9$ are each independently hydrogen atom, lower alkoxy or nitro; and
its optically active substance, pharmaceutically acceptable salt, or hydrate thereof.

8. The compound of claim 3, wherein $R^1$ is (indole-3-yl) methyl.

9. The compound of claim 3, wherein $R^5$ is phenyl optionally substituted with one or more substituents selected from the group consisting of alkoxy, alkylthio, and alkyl.

10. The compound of claim 3, wherein a configuration of asymmetric carbon atoms bonding with $R^1$ is R configuration.

11. A pharmaceutical composition comprising a compound of claim 3.

12. A pharmaceutical composition comprising a compound of claim 8.

13. A pharmaceutical composition comprising a compound of claim 9.

14. A pharmaceutical composition comprising a compound of claim 10.

15. A method of inhibiting the activity of a metalloproteinase, comprising administering to a subject in need thereof an effective amount of a compound of formula I:

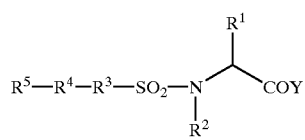

wherein $R^1$ is optionally substituted heteroarylalkyl;
$R^1$ is hydrogen atom or optionally substituted lower alkyl;
$R^3$ is optionally substituted arylene;
$R^4$ is a bond, —(CH$_2$)m—, —CH=CH— or —C≡C—;
$R^5$ is optionally substituted aryl;
Y is —NHOH or —OH;
and m is 1 or 2;
provided $R^2$ is hydrogen atom when Y is —NHOH,
with the proviso that $R^5$ and $R^3$ together do not form a biphenyl group, and
its optically active substance, pharmaceutically acceptable salt, or hydrate thereof.

16. A method of inhibiting the activity of a type-IV collagenase, comprising administering to a subject in need thereof an effective amount of a compound of formula I:

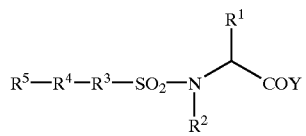

wherein $R^1$ is or optionally substituted heteroarylalkyl;
$R^2$ is hydrogen atom or optionally substituted lower alkyl;
$R^3$ is optionally substituted arylene;
$R^4$ is a bond, —(CH$_2$)m—, —CH=CH— or —C≡C—;
$R^5$ is optionally substituted aryl;
Y is —NHOH or —OH;
and m is 1 or 2;
provided $R^2$ is hydrogen atom when Y is —NHOH, with the proviso that $R^5$ and $R^3$ together do not form a biphenyl group, and
its optically active substance, pharmaceutically acceptable salt, or hydrate thereof.

17. The compound of claim 4, wherein $R^7$ is phenyl optionally substituted with one or more substituents selected from the group consisting of alkoxy, alkylthio, and alkyl.

18. The compound according to claim 3, wherein $R^1$ is optionally substituted heteroarylalkyl; $R^2$ is hydrogen or optionally substituted lower alkyl; $R^3$ is optionally substituted arylene; $R^4$ is —CH$_2$)m—, —CH=CH— or —C≡C—; $R^5$ is optionally substituted aryl; and m is 1 or 2, its optically active substance, a pharmaceutically acceptable salt thereof, or a hydrate thereof.

* * * * *